(12) United States Patent
Carter et al.

(10) Patent No.: US 9,065,553 B2
(45) Date of Patent: Jun. 23, 2015

(54) ACOUSTIC MODEM FOR FLUID MONITORING IN MEDICAL AND INDUSTRIAL APPLICATIONS

(75) Inventors: Stephen S. Carter, Rancho Santa Fe, CA (US); Vito R. Bica, Poway, CA (US); Jin Guo, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 613 days.

(21) Appl. No.: 13/230,323

(22) Filed: Sep. 12, 2011

(65) Prior Publication Data

US 2013/0064044 A1    Mar. 14, 2013

(51) Int. Cl.
*G10K 11/00* (2006.01)
*H04B 11/00* (2006.01)
*G06F 19/00* (2011.01)

(52) U.S. Cl.
CPC ............ *H04B 11/00* (2013.01); *G06F 19/3418* (2013.01)

(58) Field of Classification Search
CPC .......... G08B 25/00; G08B 3/10; G08C 23/02; H03K 17/94
USPC .................... 340/10.1, 572.1, 1.1, 10.3, 10.4; 367/197, 183
See application file for complete search history.

(56) References Cited

U.S. PATENT DOCUMENTS

| | | | |
|---|---|---|---|
| 5,853,005 A | 12/1998 | Scanlon | |
| 7,423,931 B2 | 9/2008 | Martin, II et al. | |
| 7,614,302 B2 * | 11/2009 | DiFoggio et al. | 73/597 |
| 7,933,780 B2 * | 4/2011 | De La Huerga | 705/2 |
| 7,982,612 B2 * | 7/2011 | Braun | 340/572.1 |
| 8,075,514 B2 * | 12/2011 | Butterfield et al. | 604/65 |
| 8,171,798 B2 * | 5/2012 | Van Tuyl et al. | 73/597 |
| 8,341,669 B2 * | 12/2012 | Lau et al. | 725/39 |
| 2004/0051368 A1 | 3/2004 | Caputo et al. | |
| 2004/0193453 A1 * | 9/2004 | Butterfield et al. | 705/2 |
| 2006/0065713 A1 * | 3/2006 | Kingery | 235/380 |
| 2009/0112178 A1 | 4/2009 | Behzadi | |
| 2010/0001838 A1 * | 1/2010 | Miodownik et al. | 340/10.1 |
| 2010/0305499 A1 * | 12/2010 | Matsiev et al. | 604/67 |
| 2011/0247416 A1 * | 10/2011 | Cooper et al. | 73/587 |
| 2013/0208497 A1 * | 8/2013 | Provost et al. | 362/555 |

* cited by examiner

*Primary Examiner* — Eric M Blount
(74) *Attorney, Agent, or Firm* — Shyam K. Parekh

(57) ABSTRACT

The various embodiments provide systems, devices, and methods which include an acoustic tag configured to transmit an acoustic signal through a contact medium that may be received by an acoustic modem, with the acoustic signal configured to transmit information. By modulating sound traveling through an acoustic connection between the fluid container and a pump, meter or valve, information such as an identifier of the fluid or container may be transmitted without risk of confusion with other fluid containers in the vicinity. In a medical embodiment, IV fluid and the IV drip tube provide a fluid and plastic acoustic connection to an IV pumping or metering device and an IV bag through which sound may be transmitted. The transmission of identification information through this physical connection may insure that the pumping or metering device only communicates with the IV bag coupled to the pump. Acoustic tags may be active or passive.

64 Claims, 40 Drawing Sheets

ACOUSTIC MODEM FOR FLUID MONITORING IN MEDICAL AND INDUSTRIAL APPLICATIONS

FIELD

The present application relates to methods and mechanisms for communicating information related to fluid containers via acoustics.

BACKGROUND

Item identification is important in a wide range of industries, from manufacturing to food service. One specific industry where the identification of items is of life and death importance is health care. The proper identification of pills, fluids, drugs, equipment, and even the patients themselves is critical to providing effective and safe care and treatment. Systems which can reduce human error, especially human error in administering intravenous ("IV") drugs and other IV substances, are helpful to prevent mistakes and reduce the requirement for health care supervision.

Bar codes have been used to identify medicines, foods, patients, equipment, etc. While bar codes systems can be effective, such systems require operators to scan the appropriate bar code, and thus require extra labor and are still subject to human error. Another previous solution to the identification of health care items has been to use radio frequency identification ("RFID") technology in hospital settings. RFID tags are now included in many medical systems, food trays, medication containers, patient wrist bands, etc. One proposed solution to the problem of verifying/controlling the administering of IV's is to add an RFID tag to IV fluid bags and an RFID transceiver to IV fluid pumps used to meter fluids to the patient. In such a system, the IV fluid pump can identify the fluid inside an IV fluid bag by wirelessly reading the bags RFID tag. If the identifier received from IV bag RFID does not match an expected value, the fluid pump automatically can sound an alarm and suspend or block administration of the fluid to the patient.

Using RFID technology in the close quarters of a hospital room can lead to confusion when many items in the room are equipped with RFID tags. Multiple patients may be in the room and patients may be receiving multiple IV fluids from multiple IV bags. Also, IV bags not currently in use may also be present in the room for storage or in trash receptacles. In such a crowded environment an RFID reader may be unable to uniquely identify the wireless signals emitted by the RFID tag on an IV bag coupled to the IV fluid pump. This presents the potential for error that could jeopardize patient safety.

SUMMARY

The various embodiments provide systems, devices, and methods that enable a fluid pump, meter, or other dispenser to identify a fluid container using an acoustic modem to transmit identifying communication through a fluidic path between the container and the pump, meter, or dispenser. By providing a direct contact transmission of information, identifier information can be exchanged between the container and the pump, meter, or dispenser without confusion with other containers that may be in the immediate vicinity.

The various embodiments provide a method for receiving information from a fluid container in fluidic communication via a fluid conduit with an interrogator or reader which may be associated with a fluid pump, meter, or dispenser. The method may include transmitting from the fluid container an acoustic signal that passes through the fluid conduit to the interrogator or reader where the signal is received for monitoring or controlling an operation. In an example embodiment, the fluid container may be an IV bag, the interrogator or reader may be associated with an IV fluid pump, and the operating condition set in response to the receive acoustic signal may include initiating or suspending pumping of the fluid and setting an alarm condition.

Embodiments include systems in which a fluid container (e.g., an IV bag) includes an acoustic emitter and a fluid pump, meter, or dispenser (e.g., an IV pump) includes an acoustic modem configured to receive and process acoustic signals and a processor configured to act on signals from the acoustic modem. The fluid container and the fluid pump, meter, or dispenser are connected via a fluid conduit, such as a tube, pipe or channel in a manner that enables sound to be conducted. This provides an acoustic path via the conduit or the fluid itself through which may be communicated acoustic signals encoding information regarding the fluid container or fluid within the container to the fluid pump, meter, or dispenser.

In various embodiments of such system, the acoustic emitter may be an active emitter or a passive emitter. In an embodiment, an active acoustic emitter may include a receiver for receiving a query signal, a sound emitter configured to emit sound into the fluid or fluid conduit, and a processing circuit coupled to the receiver and sound emitter that is configure to recognize a receive query signal and, in response, cause the sound emitter to emit an acoustic signal encoding information. The query signal may be any type of signal that can be received by the acoustic emitter, including radio frequency, light, and acoustic signals. In another embodiment, an active acoustic emitter may include a sound emitter configured to emit an acoustic signal encoding information, and a power source that is configured to provide electrical power to the sound emitter in response to an activation event, such as connection to a fluid conduit, connection to a pump, meter, or dispenser, initiation of fluid flow, shaking or deformation. In an embodiment, a passive acoustic emitter may include an acoustic harmonic oscillator, such as a tuned echo chamber or vibrator, configured to emit sound into the fluid at a particular frequency when exposed to sound of a broad range of frequencies or another frequency. Embodiment acoustic emitters may be coupled to the fluid container in a variety of configurations, including, for example, on an exterior surface, embedded within a surface of the container, on an interior surface, and suspended within the contained fluid.

In various embodiments the acoustic modem associated with the system pump, meter, or dispenser may include a sound receiver (e.g., a microphone or hydrophone) and a processor coupled to the sound receiver configured to recognize information encoded within received acoustic signals and to take an action based on the recognized information. In an embodiment, the acoustic modem may also include a sound emitter coupled to the processor and configured to emit an acoustic query signal into the fluid conduit for transmission to the fluid container. The acoustic modem may be configured as an integral component of the pump, meter, or dispenser, or as a separate component that is electronically coupled to the pump, meter, or dispenser.

In a medical application embodiment, the fluid container may be an IV fluid bag, the fluid conduit may be the tube connected to the IV fluid bag, and the pump, meter, or dispenser may be an IV pump or IV meter. In an embodiment, the acoustic modem may be included within the IV pump or IV meter, and a processor of the acoustic modem and/or of the IV pump or IV meter may be configured to recognize or process an acoustic signal emitted by the acoustic emitter within the IV fluid bag that is conducted through fluid within the tube and/or the tube itself to obtain the encoded information, and to commence or suspend IV fluid flow based upon the encoded information.

The various embodiments may also be implemented in a variety of industrial (i.e., non-medical) applications. For example, the embodiments may be implemented within a beverage dispenser in which the fluid container may be a beverage syrup bag (or tank or canister), the fluid conduit may be the tube connected to the beverage syrup bag, and the pump, meter or dispenser may be the beverage dispenser which mixes syrup with carbonated water. In this example embodiment, the acoustic modem may be included within the beverage dispenser, and a processor of the acoustic modem and/or of the beverage dispenser may be configured to recognize or process an acoustic signal emitted by the acoustic emitter within the beverage syrup bag that is conducted through fluid within the tube and/or the tube itself to obtain the encoded information, and to commence or suspend beverage fluid flow based upon the encoded information.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Figure 1:
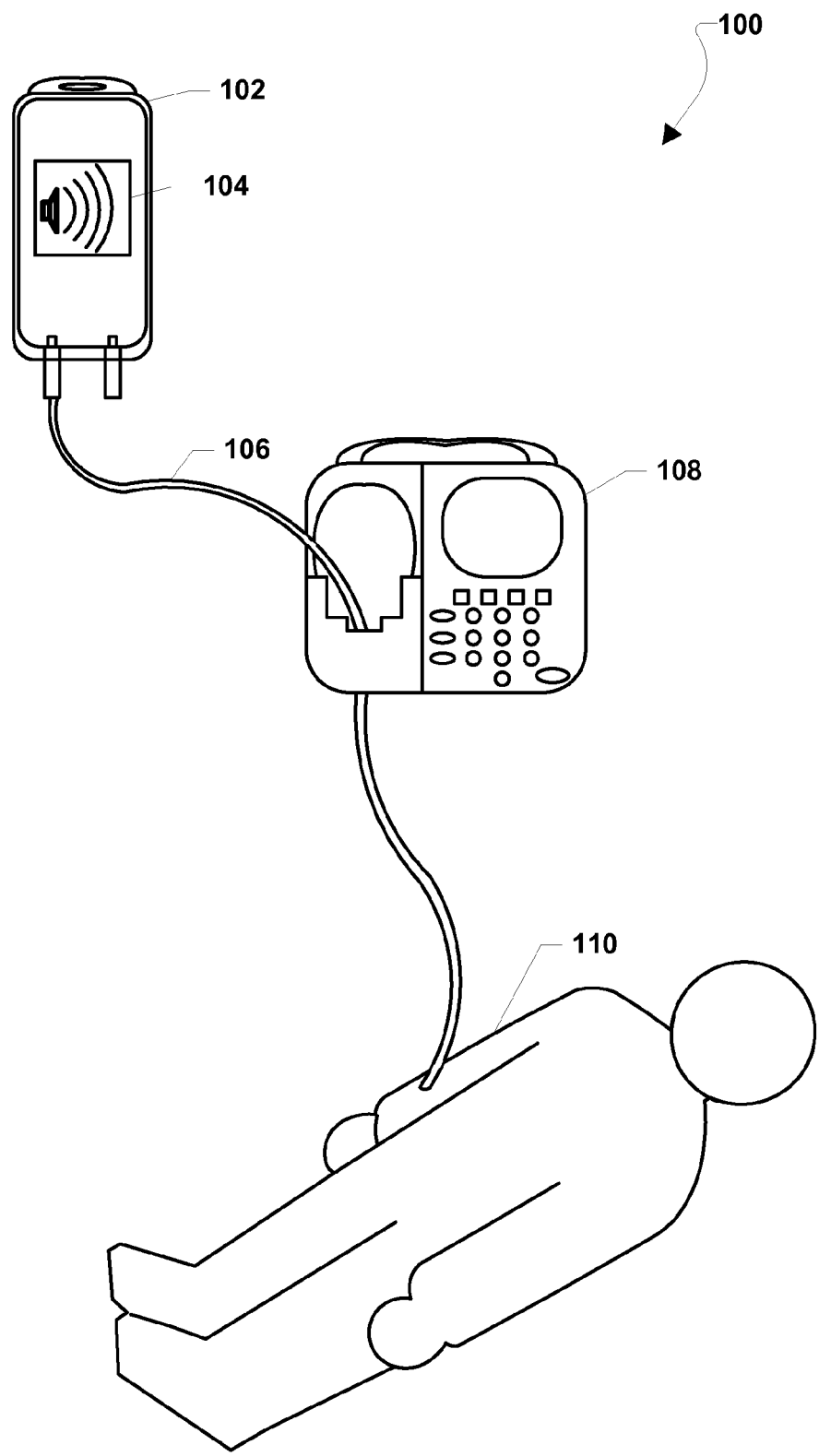
FIG. 1 is an illustration of a fluid communication system suitable for use in an IV fluid embodiment.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

The various embodiments are described herein using the example of a medical application in which a main acoustic tag is included on or within an IV bag and the acoustic modem is included within an IV pump or IV meter. This example is useful for describing the various components and functionality of the embodiment devices, systems and methods. However, the embodiments and the scope of the claims are not limited to such a configuration unless specifically recited. Describing the embodiments in terms of other potential applications would be unnecessary and repetitive. Thus, the term "IV bag" is used herein to refer generally to any form of fluid container to which the embodiments could be applied, and is not intended to limit the scope of the claims unless specifically recited. Similarly, the terms "pump" and "IV pump" are used herein to refer generally to any form of fluid dispenser to which the embodiments could be applied, and is not intended to limit the scope of the claims unless specifically recited. In particular, the term "IV bag" is not intended to limit the scope of the claims to a particular fluid or form of administration, and thus may encompass intravenous, subcutaneous, arterial, epidural, or other types of administration in medical applications.

Similarly, the term "IV pump" is used herein to refer generally to any and all fluid pumps or fluid metering devices for controlling, pumping or measuring a flow of a fluid. As an example, in medical applications "IV pumps" may be infusion pumps, syringe pumps, large volume pumps, or small volume pumps.

The various embodiments provide systems, devices, and methods to enable a device pumping, metering or otherwise controlling flow of a fluid to reliably identify the fluid or source of a fluid by using acoustic signals which flow through the fluid. The fluid provides a direct contact medium for communicating identifying information, thereby avoiding problems associated with RFID and other electromagnetic signaling technologies.

Item identification and verification is important in a wide range of industries, from manufacturing to food service. One specific industry where the identification of items is of life and death importance is health care. The proper identification of pills, fluids, drugs, equipment, and even the patients themselves is critical to providing effective and safe care. Systems which can reduce human error, especially human error in administering intravenous ("IV") drugs and other IV substances, could prevent administering the improper fluid by accident.

One previous solution to the identification of health care items has been to use radio frequency identification ("RFID") technology in hospital settings. One proposed solution to the problem of verifying/controlling the administering of IV's has been to add an RFID tag to IV fluid bags, and an RFID transceiver to the IV fluid pump used to meter fluids to the patient. In such a system, the IV fluid pump could identify the fluid inside the IV fluid bag based on the information received via wireless signals from the RFID tag, and can control the administration of the fluid to the patient automatically without a nurse needing to input information about the fluid. This solution would reduce the workload on nurses and reduce the chance for human error since the fluid pump is able to verify the identity of the IV fluid autonomously.

A drawback to using RFID technology in the close quarters of a hospital room is that many items in the room may need to be identified or may be equipped with RFIDs. Patients may be receiving multiple IV fluids from multiple IV bags, and multiple patients may be sharing a single hospital room. In a crowded environment it can be difficult for an RFID transceiver to distinguish signals received from several RFID tags, such as to distinguish an RFID tag on an IV bag connected to an IV pump from tags on other IV bags within the same room. As an example, an IV pump in use in a room with two patients might not be able to distinguish which fluid bag is associated with which patient because the RFID transceiver on the IV pump would be receiving signals from RFID tags on both patients' IV bags, as well as any IV bags that might be stored in the room or discarded in trash receptacles. This potential association error presents a problem for both patient safety and reduces the ability for further automation of hospital workflow, thereby limiting the use of RFID technology in this application.

The various embodiments solve the association problem by using an acoustic modem to transmit identifying communication that travels as an acoustic signal through a contact medium to allow for contact transmission of information. Using the example of an IV bag and pump embodiment, the IV fluid and the IV drip tube may provide a fluid and plastic acoustic connection between a pumping or metering device and the IV bag through which sound may be transmitted. By modulating sound traveling through this acoustic connection between the pump and the IV bag, information may be transmitted between an acoustic emitter on the bag and an acoustic receiver on the pump. The transmission of identification information through this physical acoustic connection may ensure that the pumping or metering device only communicates with the IV bag actually coupled to the pump.

The various embodiments may use sound traveling through the fluid and a fluid conduit, such as an IV tube, that forms an acoustic link between an acoustic modem on the pump and the IV bag to transmit information. An acoustic signal may be applied to the fluid within the IV bag via an acoustic modem that is part of an acoustic tag. In an embodiment an active acoustic tag on or within the IV bag may transmit an acoustic signal into the fluid. Such an acoustic signal may be conducted through the fluid and down the tube to an acoustic transducer on the pumping or metering device. The pumping or metering device may receive the information in the acoustic signal to determine the type of fluid being administered.

In another embodiment, the acoustic tag on the fluid container may be passive. In such an embodiment, an acoustic transducer on the pumping device may send an acoustic signal through the fluid to the acoustic tag which returns an echo or retransmitted acoustic signal with a recognizable pattern or frequency. A passive acoustic tag may function using one of two mechanisms. In a first mechanism, the tag may be configured with a structure which creates a unique echo, such as reflecting certain frequencies or harmonics of an incident sound (e.g., may be generated by an acoustic modem on the pump) while absorbing other frequencies. This unique echo signal may then be reflected back to the transducer on the pump through the acoustic connection provided by the fluid and fluid conduit. The transducer on the pump may receive the unique echo and recognized the reflected frequencies to determine an identity of the fluid being administered. In a second mechanism, the acoustic tag may be configured with circuitry that uses energy within the incident sound to generate power that is used to power an acoustic emitter which may emit a signal encoding identity information. Power may be harvested from incident sound by using a piezoelectric crystal coupled to an inductor or a diode/capacitor element. In such a circuit, the power generated when the piezoelectric crystal is deformed by incident sound waves may accumulate in the inductor or diode/capacitor element until it is sufficient to power a circuit that applies a modulating signal to the same or a different piezoelectric transducer to generate a sound on which information (e.g., an ID number) is modulated.

In an exemplary embodiment, an acoustic transceiver may be attached to an IV pump and the IV bag may be configured with an acoustic tag. The acoustic tag may be part of a label affixed to the bag, or may be built into the IV bag itself. The acoustic tag may include a power source connected to a modulator or processor circuit coupled to a piezoelectric crystal (or other sound emitting structure). When powered, the acoustic tag may transmit a recognizable acoustic signal into the IV fluid. When the IV bag is attached to an IV pump, the encoded acoustic signal may travel from the IV bag through the fluid contained within the IV line to the IV pump. A transducer on the IV pump may receive the acoustic signal in the fluid, and translate the signal into digital information that a processor may use to determine the type of fluid being pumped, as well as other information, such as lot number, supplier, its expiration date, etc. Based on the information included within the acoustic signal, the IV pump may take appropriate actions automatically, such as adjusting the pumping rate to match a proper dosage of the fluid, or terminating or preventing fluid flow and sounding an alarm when an incorrect, expired or recalled fluid is indicated in the information encoded within the received acoustic signal.

FIG. 1 illustrates components of a system 100 for delivering IV fluid according to the various embodiments. An IV bag 102 may contain a fluid. As an example, the fluid may be a saline solution or a drug intended to be administered to a patient 110. The IV bag 102 may be connected to a fluid line 106 which is configured to allow fluid to flow from the IV bag 102 to the patient 110. The fluid line 106 may pass through an IV pump 108. The IV pump 108 may be configured to control the flow of the fluid from the IV bag 102 through the fluid line 106 to the patient 110. An acoustic tag 104 may be present at the IV bag 102. An acoustic tag 104 may be an active tag (i.e., contains its own power source) or a passive tag (i.e., contains no power source) as described in more detail below. In an embodiment, communications between the acoustic tag 104 and the IV bag occur via the fluid line 106. By transmitting sound waves through the fluid, the acoustic tag 104 and the IV pump 108 may share information without the risk of confusion because the sound travels through the physical acoustic connection between the tag and pump formed by the fluid and fluid line 106.

Figure 2:
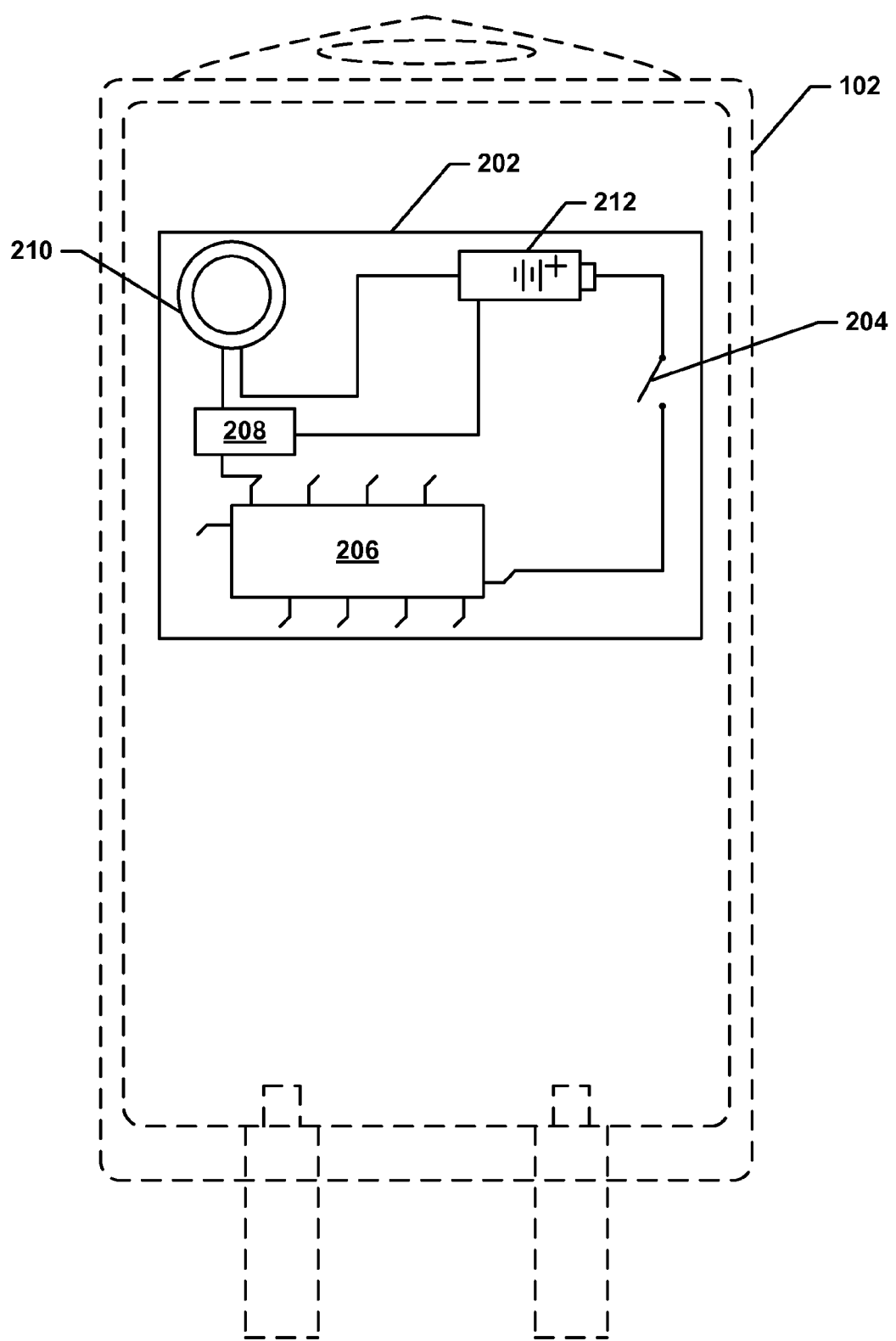
FIG. 2 is a component block diagram of an acoustic tag according to a first embodiment.

FIG. 2 illustrates a first embodiment of an active acoustic tag 202 which may be used with an IV bag 102. As described in more detail below with reference to FIGS. 9-12, the active acoustic tag 202 may be coupled to the IV bag 102 on an external surface, within a portion of the container wall, on an interior surface or within the fluid itself.

In the embodiment illustrated in FIG. 2, the active acoustic tag 202 includes an activation switch 204 which may be coupled to a battery 212. When closed, the activation switch 204 may complete an electrical circuit that applies power from the battery 212 in order to activate the active acoustic tag 202. This activation switch 204 may be closed by a number of different types of actuations. As an example, the activation switch 204 may be closed by pulling a tab on the switch, by squeezing or otherwise manipulating the IV bag 102, or by some other physical manipulation of the IV bag 102. The activation switch 204 may be used to prevent connecting to the acoustic tag 202 to the battery when the IV bag 102 is in storage, thereby ensuring that battery power is available when the IV bag is used. In an alternative embodiment (not shown), the activation switch 204 may not be included, in which case the active acoustic tag 202 may be permanently coupled to the battery 212. By using low power electronics, such embodiment may enable a long battery life commensurate with the shelf life of the IV fluid. This alternative embodiment may be preferred to eliminate the potential user error of failing to activate the active acoustic tag 202 at the time of use.

The active acoustic tag 202 may also include an integrated circuit (IC) chip 206 that provides processor or logic functionality for controlling the acoustic emissions of the tag. The IC chip 206 may be a custom circuit that is configured to generate signals to cause the active acoustic tag 202 to emit encoded acoustic signals as described herein. The IC 206 chip may be configured to generate signals encoding a particular set of information (e.g., an identifier), or may include a memory on which may be stored an identifier of the IV bag, as well as other information such as lot number, fluid type, expiration date, etc. alternatively, the acoustic tag 202 may include a separate memory chip (not shown) coupled to the IC chip 206. Either configuration of memory is referred to herein simply as the memory within the acoustic tag 202. The IC chip may be coupled to an electric pulse generator 208, which may be coupled to a piezoelectric transducer 210. The battery 212 may be coupled to the IC chip 206, pulse generator 208, and piezoelectric transducer 210.

In operation, the embodiment illustrated in FIG. 2, may function as follows. When the activation switch 204 is closed, battery power is provided to the IC chip 206. The IC chip 206 may be configured to generate an electric signal that modulates or otherwise encodes identifying information, such as an identifier of the IV bag as well as other information that may be stored within the memory of the IC chip. The electric signal generated by the IC chip 206 may be applied to the pulse generator 208 causing it to output electrical pulses to the piezoelectric transducer 210 causing the piezoelectric transducer 210 to change shape rapidly, thereby generating sound waves. The piezoelectric transducer 210 may include or be coupled to structures that ensure the generated sound is acoustically coupled to the IV bag 102 structure and/or to the fluid within the IV bag 102. In this manner the active acoustic tag 202 is configured to transmit acoustic signals encoding information, such as identifier codes, which may be stored in the memory of the tag.

Figure 3:
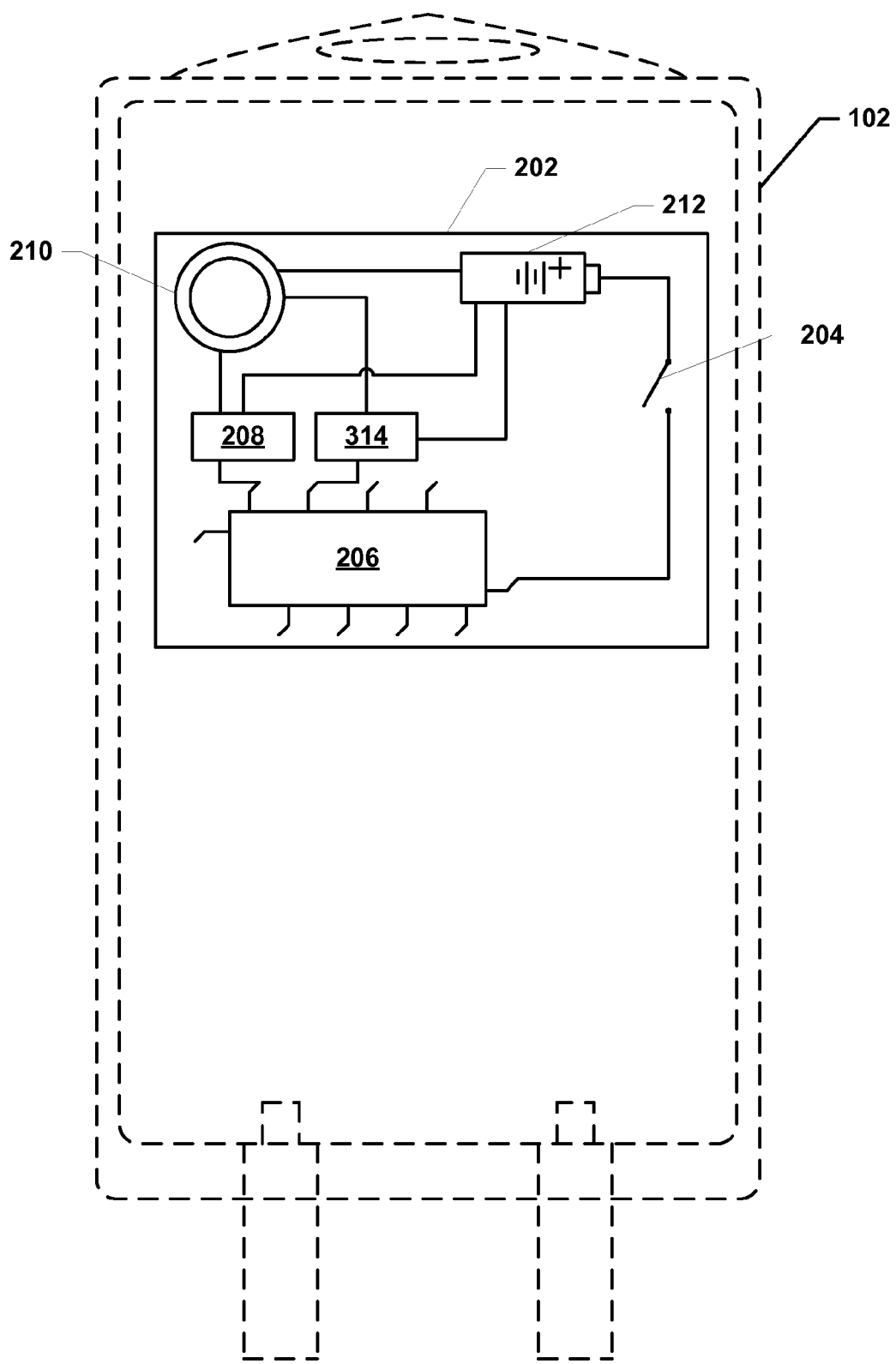
FIG. 3 is a component block diagram of acoustic tag according to an embodiment.

FIG. 3 illustrates a second embodiment of an active tag 202 that is similar to that illustrated in FIG. 2 with the addition of an signal modifying circuit 314 coupled to the piezoelectric transducer 210, the IC chip 206, and battery 212. The signal modifying circuit may be an amplifier, a receiver, an analog to digital converter, a digital signal processor (DSP), or a combination of such circuit elements. The addition of the signal modifying circuit 314 may enable the active tag 202 to both transmit and receive acoustic signals.

In the embodiment illustrated in FIG. 3, the piezoelectric transducer 210 may also be configured to generate electrical signals in response to acoustic waves within the fluid. As is well known, piezoelectric crystals will generate electrical signals when they are deformed such as via incident sound, as well as the form when electrical signals are applied to the crystal, thereby generating sound. The embodiment illustrated in FIG. 3 takes advantage of this characteristic by using the piezoelectric transducer 210 to both send and receive sound signals. Acoustic waves from the fluid, including sound waves propagated from the fluid through the IV bag 102 structure, passing through the piezoelectric transducer 210 cause it to generate electrical pulses which are received by the signal modifying circuit 314. The signal modifying circuit 314 amplifies and/or converts these electrical signals into a form that can be processed by a controller and provides modified signals to the IC chip 206. In an embodiment, the signal modifying circuit 314 may include an analog-to-digital converter circuit or a DSP which transforms the analog signals received from the piezoelectric transducer 210 into a digital form that the IC chip 206 may process. Alternatively, the IC chip 206 may include an analog-to-digital converter circuit and/or DSP within the chip itself. The IC chip 206 may be configured with executable instructions or circuit logic to process the signals received from the signal modifying circuit 314 to determine whether they include a query signal transmitted from an acoustic modem. This may involve performing a signal recognition algorithm to recognize a particular code, symbol or pattern expected from an acoustic modem. An IV bag or similar fluid container is expected to be a noisy environment, thus algorithm for recognizing a particular code, symbol or pattern may employ statistical methods. When the expected code, symbol or pattern is recognized within the received signal, the IC chip may send signals to the pulse generator 208 encoding information stored in memory of the acoustic tag 202 in a manner similar to that described above with reference to FIG. 2. In this manner, the acoustic tag 202 responds to a query signal transmitted by an acoustic modem by transmitting an acoustic signal encoding the identity information. Thus, the embodiment illustrated in FIG. 3 functions similar to an RFID except that the query and response signals are transmitted acoustically. The ability to recognize acoustic query signals enables the active acoustic tag 202 to wait for an activation signal before transmitting acoustic signals into the fluid. Since the acoustic tag 202 generates acoustic signals only in response to recognizing acoustic query signals, the switch 204 may be eliminated from this embodiment without risk of depleting the battery 212.

Figure 4:
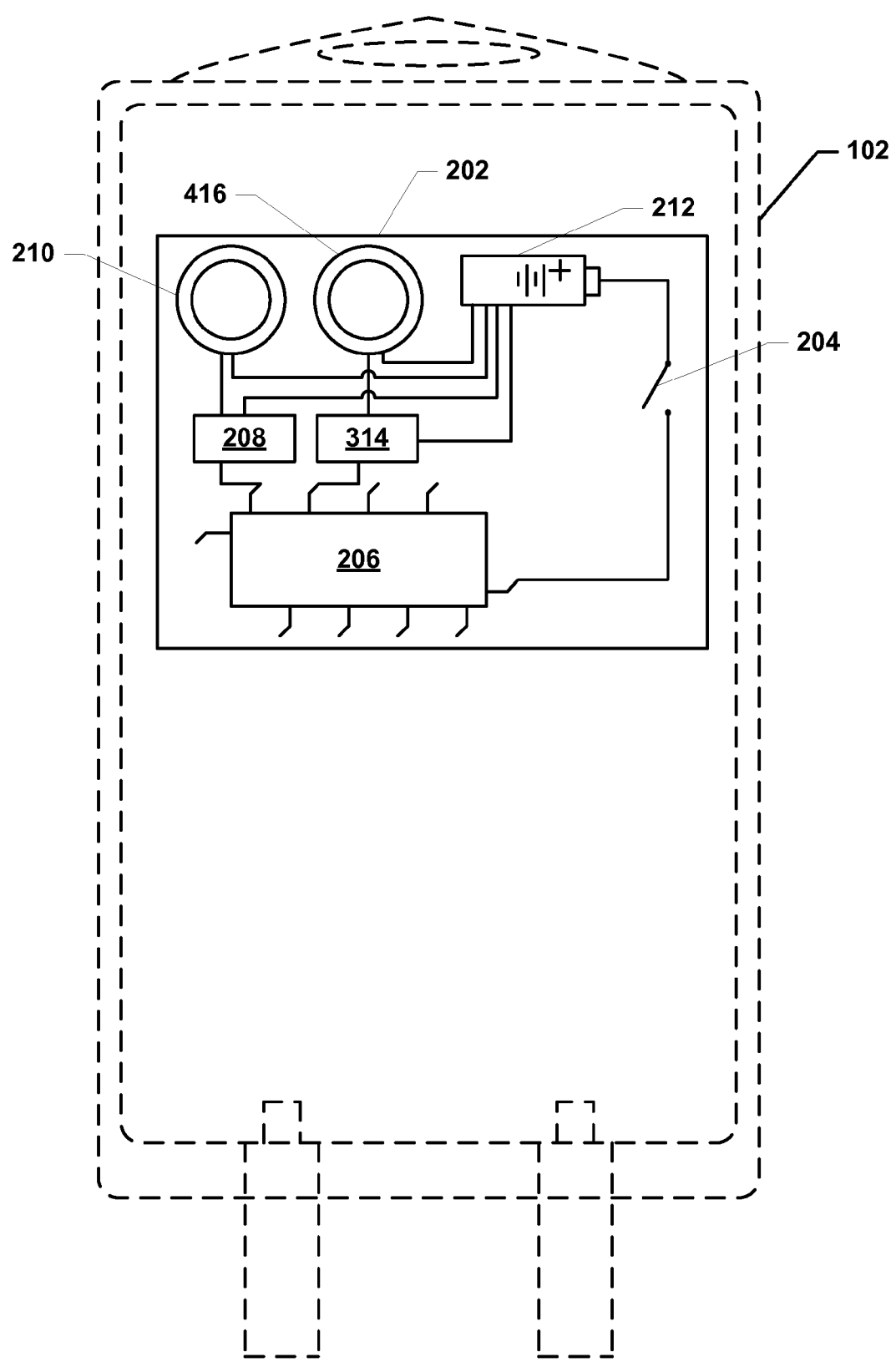
FIG. 4 is a component block diagram of an acoustic tag according to a second embodiment.

FIG. 4 illustrates a third embodiment of an active acoustic tag 202 that is similar to that illustrated in FIG. 3 with the addition of a second piezoelectric transducer 416. In this embodiment, the second piezoelectric transducer 416 is used to receive acoustic query signals, while the first piezoelectric transducer 210 is used to emit encoded acoustic signals. Thus, in this embodiment the second piezoelectric transducer 416 is coupled to the signal modifying circuit 314 and the battery 212, and the first piezoelectric transducer 210 is not coupled to the signal modifying circuit 314. The addition of a second piezoelectric transducer 416 may enable simultaneous transmission and receipt of acoustic signals by the active acoustic tag 202. This embodiment may also simplify the operation and/or fabrication of the active acoustic tag 202 by dedicating the first piezoelectric transducer 210 to transmitting acoustic signals and the second piezoelectric transducer 416 to receiving acoustic signals. In operation, the active acoustic tag 202 illustrated in FIG. 4 may function similar to the active acoustic tag 202 embodiment described above with reference to FIG. 3 except that two piezoelectric transducers (212, 416) are used. Like the embodiment described above with reference to FIG. 3, since the acoustic tag 202 generates acoustic signals only in response to recognizing acoustic query signals, the switch 204 may be eliminated from this embodiment without risk of depleting the battery 212.

Figure 5:
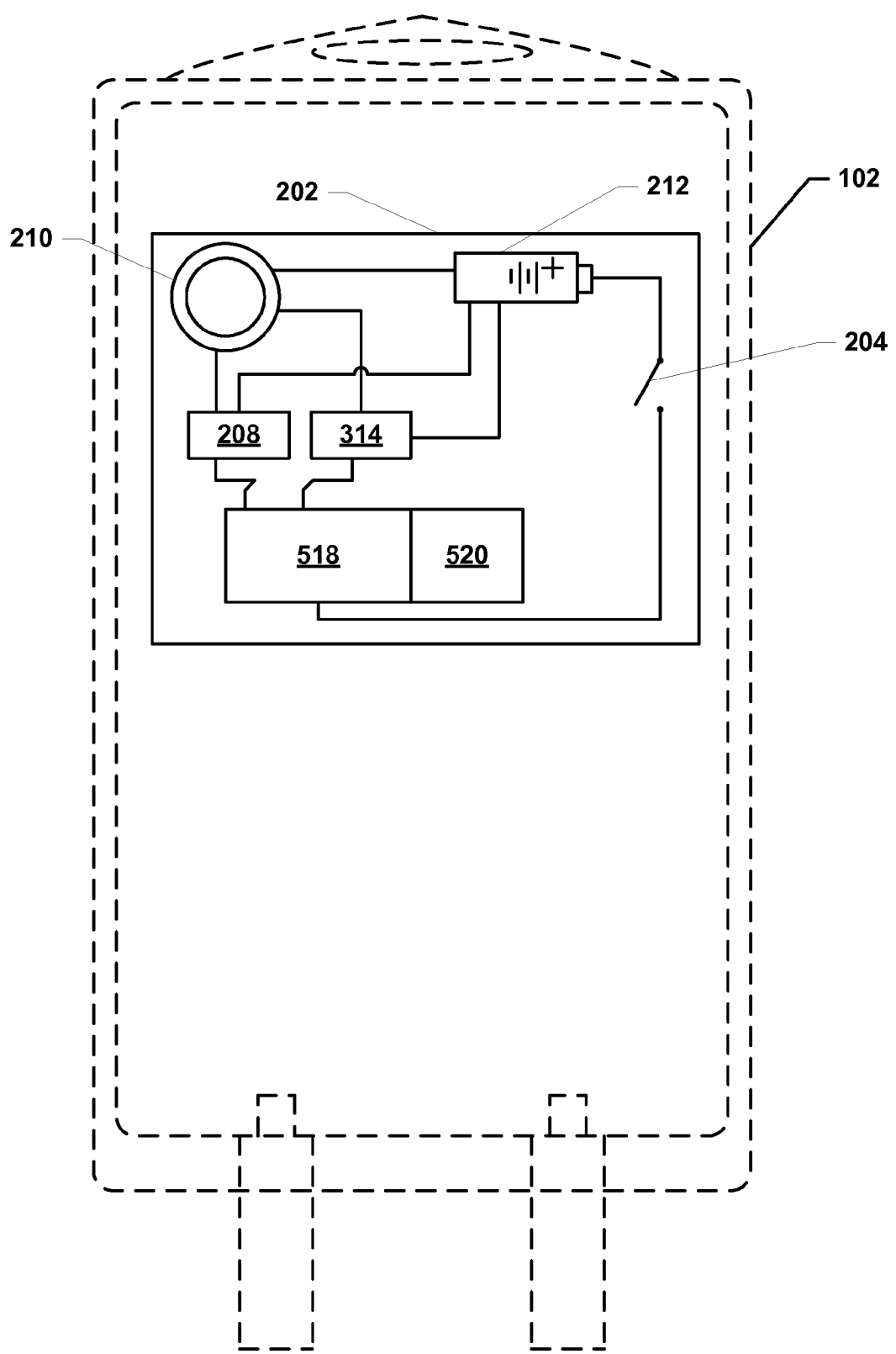
FIG. 5 is a component block diagram of an acoustic tag according to a third embodiment.

FIG. 5 illustrates a fourth embodiment of an active acoustic tag 202 that is similar to the embodiments described above with the exception that the IC chip 206 is replaced with a programmable processor or controller 518 and a memory 520. The addition of the programmable control 518 and the memory 520 allows the active acoustic tag 202 to perform logic operations to both transmit acoustic signals encoding specific information stored in the memory 520, and to compare acoustic signals received to signal characteristics stored in the memory 520 in order to recognize particular predefined acoustic modem signals. The nature of information that may be stored in the active memory 520 is further discussed below with reference to FIG. 23.

In operation, the acoustic tag 202 embodiment illustrated in FIG. 5 may function as follows. Acoustic waves from the fluid, or waves propagated from the fluid through the IV bag 102 structure, passing through the piezoelectric transducer 210 cause it to generate electrical signals which are modified (e.g., amplified and/or converted to digital format) by the signal modifying circuit 314 and passed to the programmable controller 518. As described above, either the signal modifying circuit 314 or the programmable controller 518 may include an analog-to-digital converter circuit and/or DSP to convert the received electrical signals into digital format that may be processed by the programmable controller. The programmable controller 518 may compare the characteristics of the received signals to signal characteristics stored in the memory 520 to determine if there is a match. If the programmable controller 518 determines that a received signal matches a signals stored in memory, the processor may execute a function that is correlated to that stored signal pattern.

This embodiment enables a variety of different activation signals to be correlated to a variety of different operations. For example, the acoustic tag 202 may be configured to provide only an identifier in response to a first type of acoustic query signal, and provide a complete listing of the fluid stock number, expiration date and serial number in response to a second type of acoustic query signal. Further, the acoustic query signal of particular types of pumps or meters may be programmed into the memory 520, enabling the acoustic tag 202 to respond differently to different types of devices. Since the memory 520 is programmable, the activation signals and corresponding responses may be configured at the time the tags are applied to a product. When the programmable controller 518 determines that the received signal is an activation signal or an acoustic query signal, the controller may output signals to the pulse generator 208 encoding information also stored in the memory 520 to cause the pulse generator 208 to drive the piezoelectric transducer 210 to produce acoustic signals encoding the information.

The embodiment illustrated in FIG. 5 also enables the programmable controller 518 to perform other types of operations in response to acoustic signals. For example, the programmable controller 518 may be configured with executable instructions to recognize a particular type of acoustic signal to place the tag in a programming mode in which data may be acoustically transmitted to the tag with the programmable controller 518 configured to store the data in memory 520. In this manner, the acoustic tag 202 may be applied to an IV bag during manufacturing of the bag, and programmed with serial number (or other identifier numbers), lot numbers, fluid information, expiration dates, etc. at the time the bag is filled with the fluid. As an example of another operation, the programmable controller 518 may be configured to recognize and inventory query signal, which would enable IV bags (or other types of fluid containers) to be inventoried by a contact transducer reader device.

Like the embodiment described above with reference to FIG. 3, since the acoustic tag 202 generates acoustic signals only in response to recognizing acoustic query signals, the switch 204 may be eliminated from this embodiment without risk of depleting the battery 212.

Figure 6:
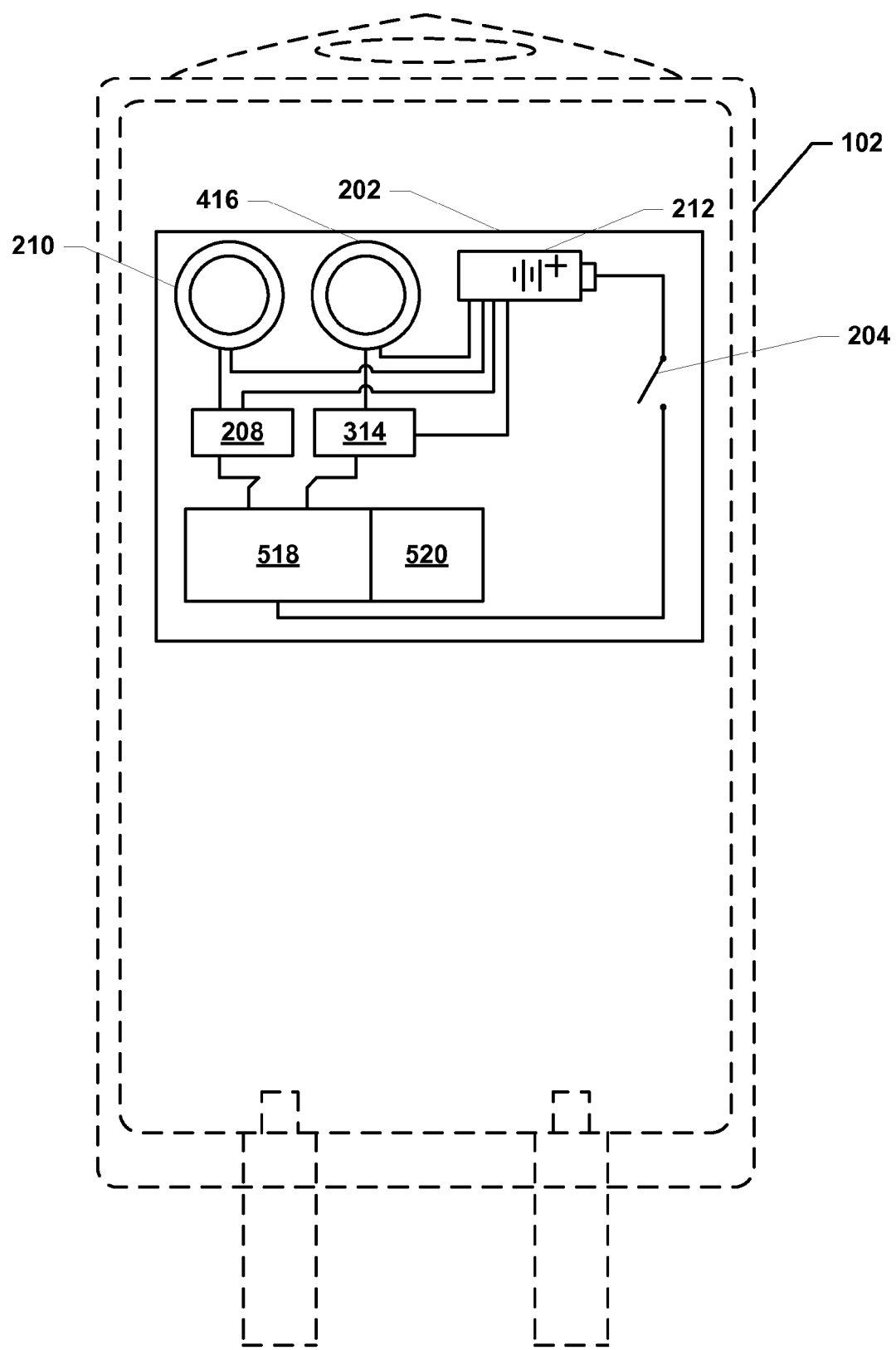
FIG. 6 is a component block diagram of an acoustic tag according to a fourth embodiment.

FIG. 6 illustrates a fifth embodiment of an active acoustic tag 202 that is similar to that illustrated in FIG. 5, with the addition of a second piezoelectric transducer 416 similar to the embodiment described above with reference to FIG. 4. As described above for the embodiment illustrated in FIG. 4, the second piezoelectric transducer 416 may be coupled to the signal modifying circuit 314 and the battery 212, and the first piezoelectric transducer 210 may not be coupled to the signal modifying circuit 314. In operation, the active acoustic tag 202 illustrated in FIG. 6 may function similar to the active acoustic tag 202 embodiment illustrated in FIG. 5, except two piezoelectric transducers (212, 416) are used.

Figure 7A:
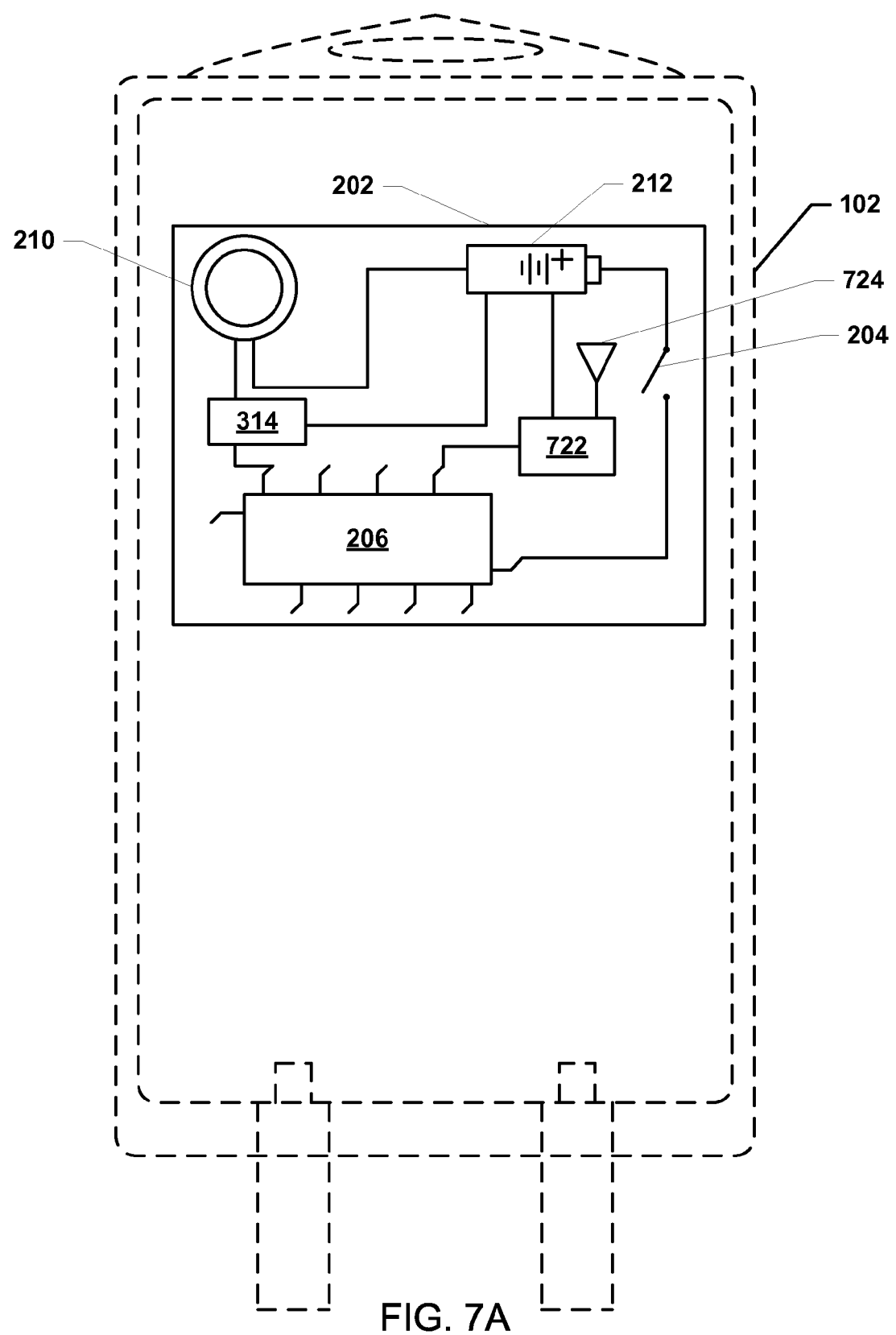
FIG. 7A is a component block diagram of an acoustic tag according to a fifth embodiment.

FIGS. 7A and B illustrates sixth and seventh embodiments of an active acoustic tag 202 which are similar to those described above the addition of an RF transmitter 722 and antenna 724. The presence of the RF transmitter 722 may allow the active acoustic tag 202 to be acoustically activated but subsequently send an RF transmission. Thus, in this embodiment the acoustic tag may also function similar to a conventional RFID tag, except that the query signal is transmitted via a content medium to ensure that the reader receives a reply only from a fluid container physically coupled to the acoustic modem associated with the pump, meter, or dispenser. This communication medium configuration eliminates the potential for confusion caused by too many RFID devices being present, since only the one physically connected to the reader will transmit RF signals.

Illustrated in FIG. 7A illustrates a sixth embodiment of an active acoustic tag 202 in which an RF transmitter 722 is coupled to the IC chip 206 and the battery 212. The RF transmitter 722 may also be coupled to an antenna 724 which may enable the active acoustic tag 202 to transmit RF signals. As an example, the RF transmitter may be an RFID transmitter, or a Bluetooth transceiver.

In operation, the embodiment acoustic tag 202 illustrated in FIG. 7A may receive and recognize an acoustic signal in a manner similar to that of the second embodiment discussed above with reference to FIG. 3. When the IC chip 206 recognizes the received acoustic signal as an activation or query signal, it may send a signal encoding information to the RF transmitter 722 which transmit an RF signal via the antenna 724. The information may be encoded into the RF signal using any well known RF transmission techniques, including those of RFID transmitters.

Figure 7B:
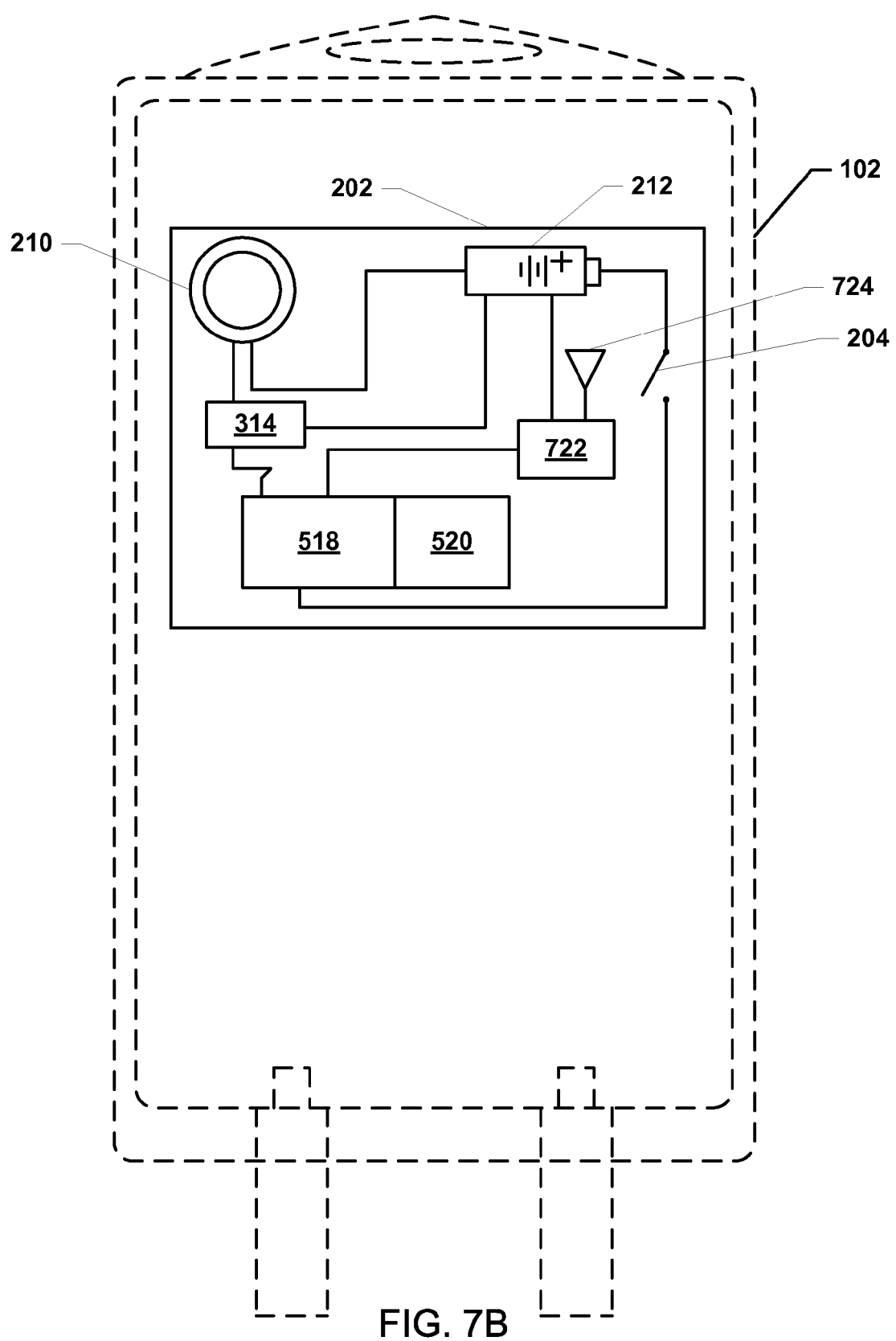
FIG. 7B is a component block diagram of an acoustic tag according to a sixth embodiment.

FIG. 7B illustrates a seventh embodiment of an active acoustic tag 202 that is similar to that illustrated in FIG. 7A, except that the IC chip 206 is replaced with a programmable controller 518 and memory 520 similar to the fourth embodiment described above with reference to FIG. 5. In operation, the active acoustic tag 202 embodiment illustrated in FIG. 7A may receive and recognize an acoustic signal as discussed above with reference to FIG. 5. When the programmable controller 518 recognizes a particular acoustic signal, such as by comparing the signal to signal characteristics resident in the memory 520, the programmable controller 518 may send signals to the RF transmitter 722 encoding information stored in the memory 520. Alternatively, the programmable controller 518 may send an activation signal to the RF transmitter 722 indicating an address in memory 520 containing information that should be transmitted. In response to such control signals, the RF transmitter 722 may generate RF signals that are transmitted via the antenna 724. The particular RF transmissions that are generated may depend upon the particular acoustic activation signal that is received, depending upon signal characteristics stored in memory 520.

Figure 8A:
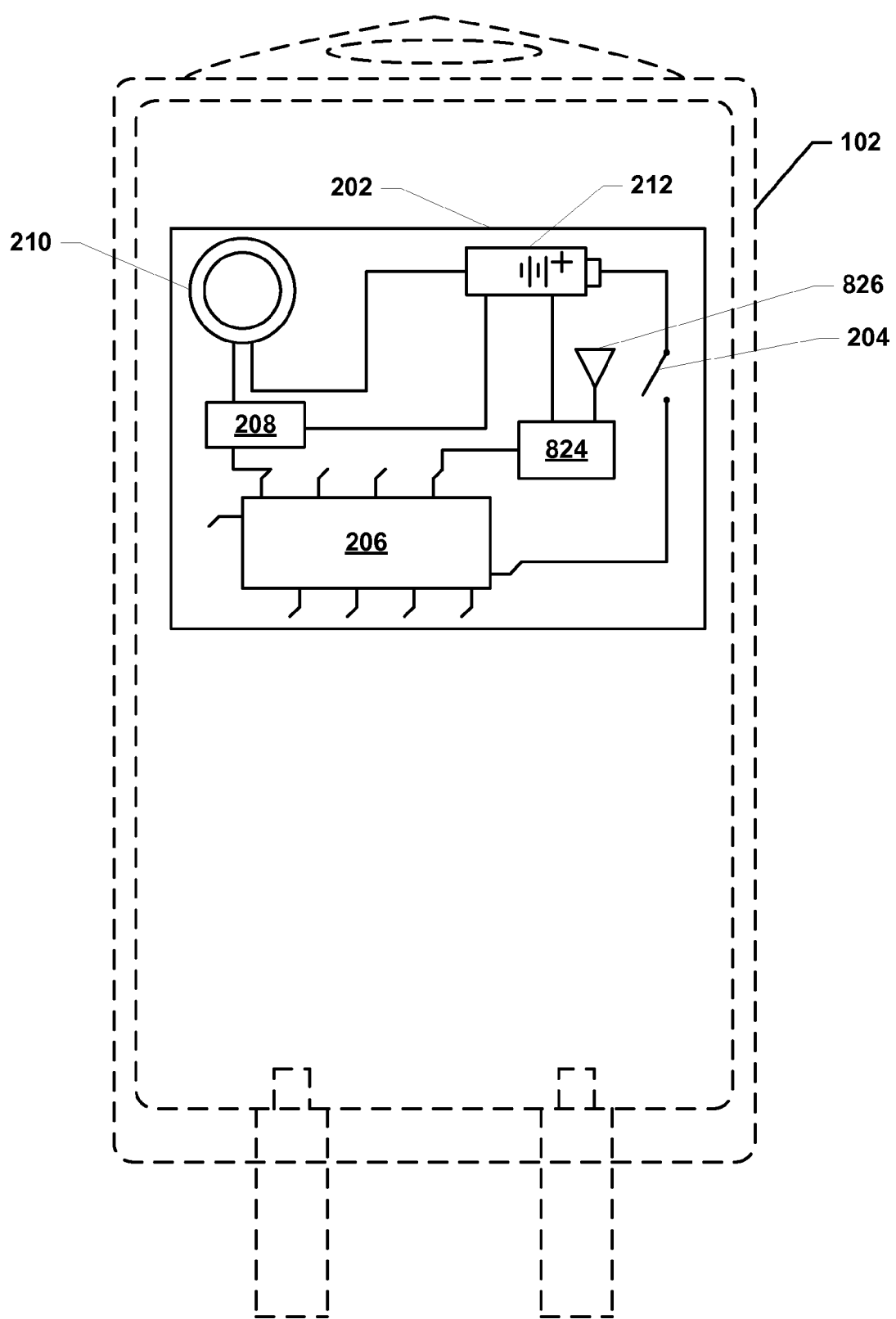
FIG. 8A is a component block diagram of an acoustic tag according to a seventh embodiment.

The query signal may be any type of signal that can be received by the acoustic emitter, including radio frequency, light (e.g., infrared signal which may be used with an infrared data link such as an IrDA link) and acoustic signals. FIGS. 8A and B illustrates eighth and ninth embodiments of an active acoustic tag 202 that includes an RF receiver 824 and antenna 826. The presence of the RF receiver 824 may allow the active acoustic tag 202 to be activated via an RF transmission while the response is in the form of an acoustic signal. Thus, in this embodiment the acoustic tag may function similar to a conventional RFID tag, except that the response signal is transmitted via a content medium to ensure that the reader receives a reply only from a fluid container physically coupled to the acoustic modem associated with the pump, meter, or dispenser. This communication medium configuration eliminates the potential for confusion caused by too many RFID devices being present since acoustic signals will only be received from the acoustic tag physically connected to the reader.

The eighth embodiment illustrated in FIG. 8A includes an RF receiver 824 coupled to the IC chip 206 and the battery 212. The RF receiver 824 may also be coupled to an antenna 826 which is configured to enable the active acoustic tag 202 to receive RF signals. As an example, the RF receiver may be an RFID or Bluetooth receiver.

In operation, the active acoustic tag 202 illustrated in FIG. 8A may receive an RF query signal via the antenna 826 and RF receiver 824. A received RF signal is processed by the RF receiver 824 which may send a signal or information encoded within the received RF signal to the IC chip 206. In response, the IC chip 206 may cause the generation of an acoustic signal similar to the first embodiment described above with reference to FIG. 2.

Figure 8B:
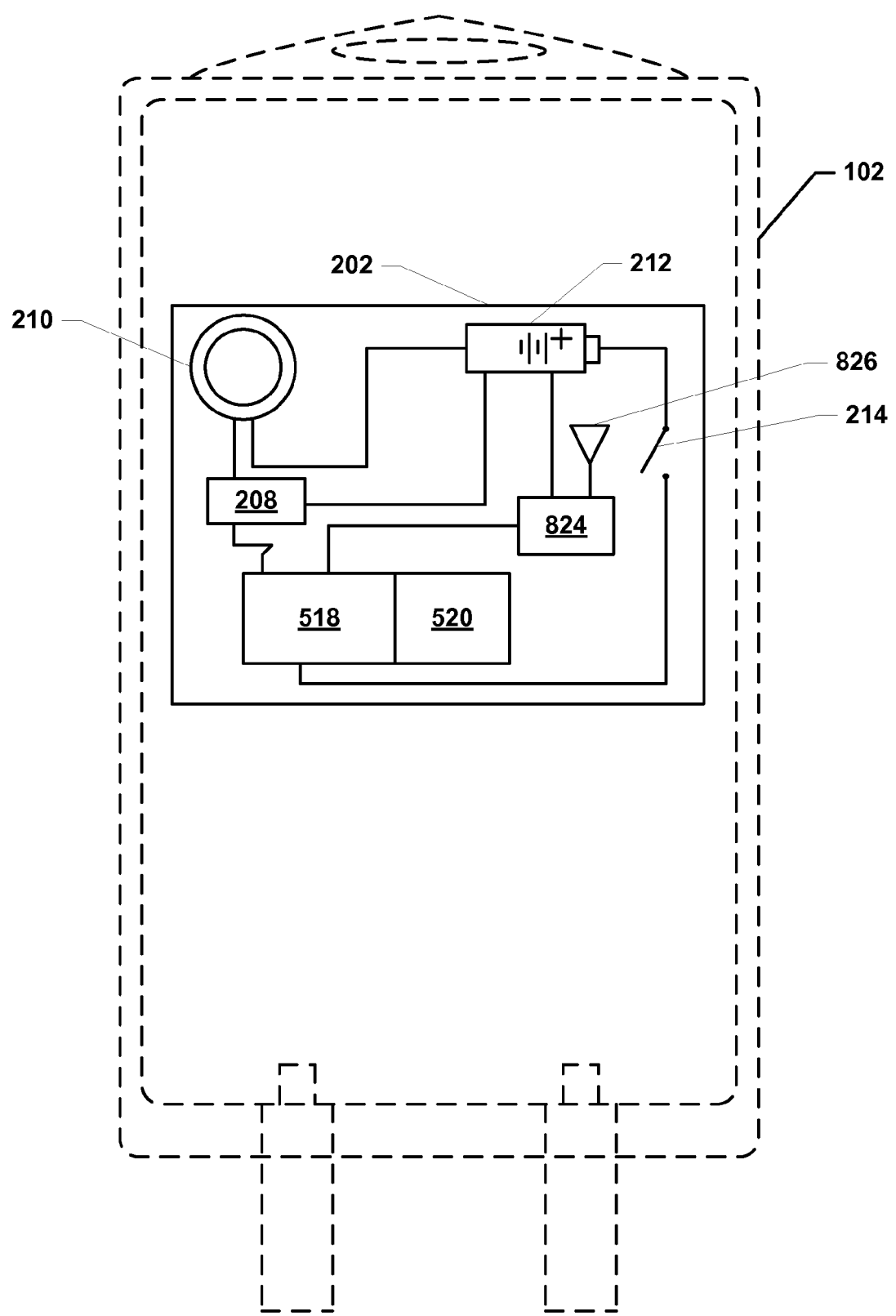
FIG. 8B is a component block diagram of an acoustic tag according to an eighth embodiment.

FIG. 8B illustrates a ninth embodiment of an active acoustic tag 202 that is similar to the eighth embodiment illustrated in FIG. 8A, except that it includes a programmable controller 518 and memory 520 similar to the fourth embodiment described above with reference to FIG. 5. In operation, the embodiment illustrated in FIG. 8A may receive an RF signal via the antenna 826 and RF receiver 824. A received RF signal is processed by the RF receiver 824 which may send a signal or information encoded within the received RF signal to the programmable controller 518. In response, the programmable controller 518 may cause the generation of an acoustic signal similar to the fourth embodiment described above with reference to FIG. 5.

A tenth embodiment of an active acoustic tag 202 includes components similar to those illustrated in FIGS. 7A through 8B, with the exception that the RF transmitter 722 and receiver 824 are replaced with a transceiver (i.e., a circuit that can both transmit and receive). This embodiment essentially combines an RFID transceiver with an acoustic tag 202, to provide an identifier tag that can function either acoustically or via RF signals with activation being achieved via either acoustic or RF signals. This embodiment may enable the tag to be programmed with identifier and other information via RF signals, while the tag functions in conjunction with a pump, meter, or dispenser via acoustic signals as described above.

FIGS. 9-12 illustrate alternative configurations for placing an acoustic tag on or within a fluid container. FIGS. 9-12 also illustrate acoustic wave propagations to and from acoustic tags.

Figure 9:
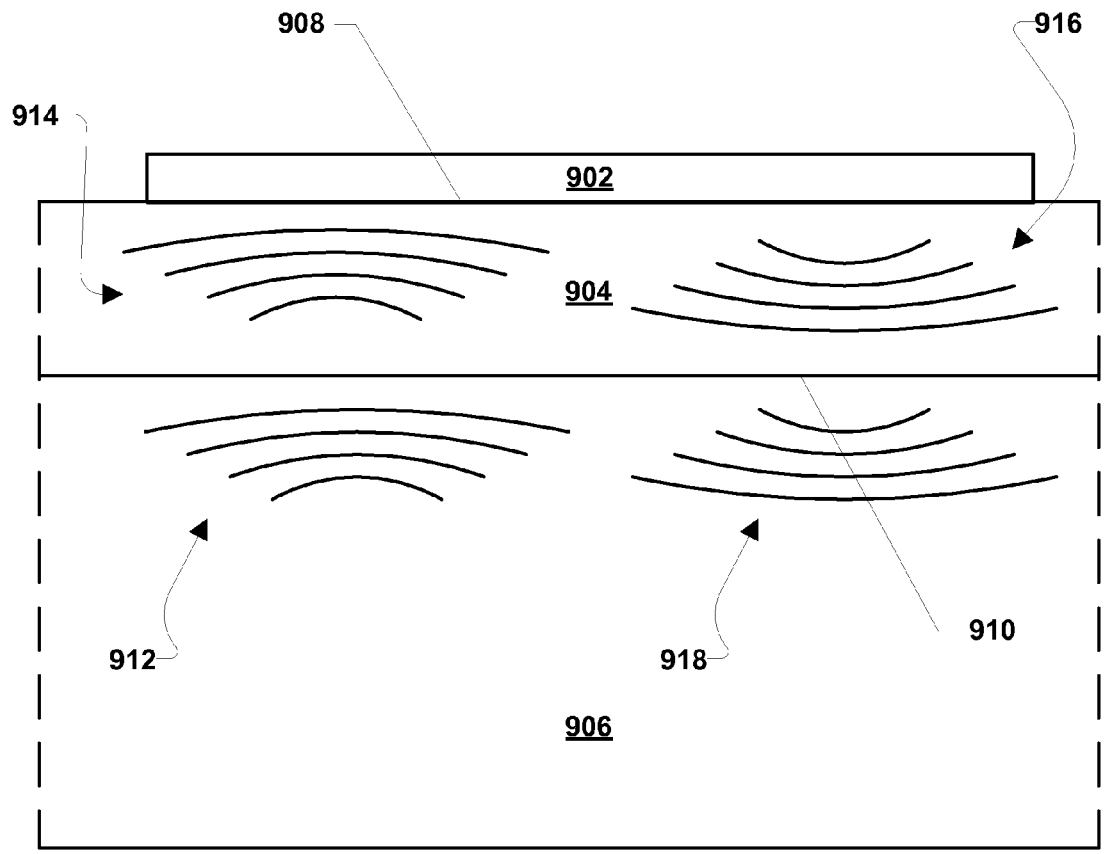
FIG. 9 illustrates a first embodiment configuration of an acoustic tag positioned on an exterior surface of a fluid container including acoustic wave propagation.

FIG. 9 illustrates an embodiment in which an acoustic transmitter/receiver 902 is coupled to the outside surface 908 of a fluid containing structure 904. The fluid containing structure 904 may be a fluid container or a fluid conduit. Acoustic waves 912 within the fluid 906 incident upon the fluid side (i.e., inside) surface 910 of the fluid containing structure 904 pass through (acoustic waves 914) the fluid containing structure 904 to interact with the acoustic transmitter/receiver 902. Acoustic waves 916 generated by the acoustic transmitter/receiver 902 pass through the fluid containing structure 904 and into the fluid 906 (acoustic waves 918).

Figure 10:
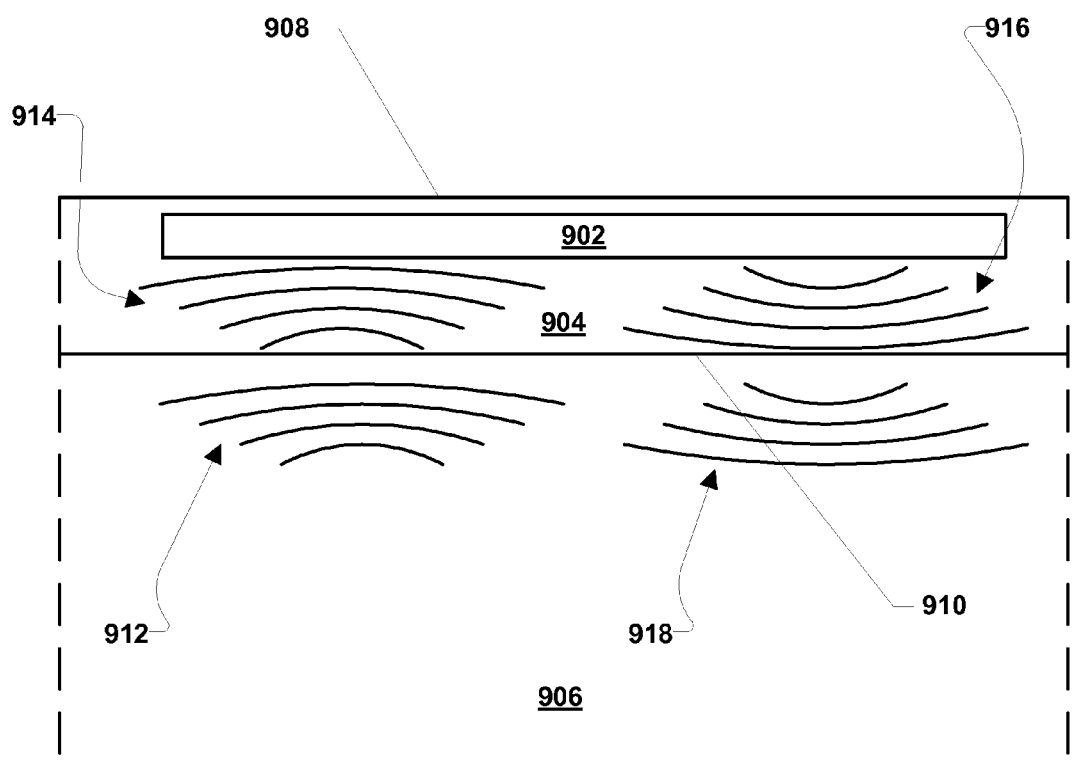
FIG. 10 illustrates a second embodiment configuration of an acoustic tag positioned within a structure of a fluid container including acoustic wave propagation.

FIG. 10 illustrates an embodiment in which the acoustic transmitter/receiver 902 is embedded within the fluid containing structure 904. Embedding the acoustic transmitter/receiver 902 within the fluid containing structure 904 may improve the acoustic coupling of the acoustic transmitter/receiver 902 to/with acoustic waves 914 and 916 traveling through the structure 904 because the acoustic waves 914 and 916 do not have to cross the outside surface 908 of the fluid containing structure 904.

Figure 11:
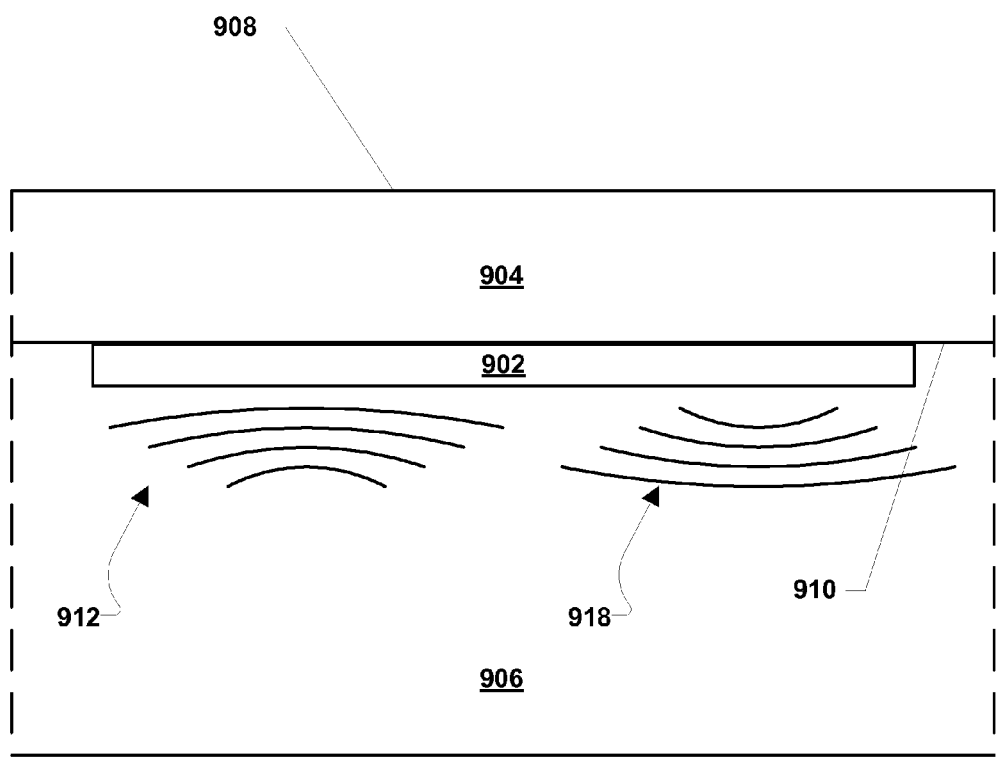
FIG. 11 illustrates a third embodiment configuration of an acoustic tag positioned on an interior surface of a fluid container including acoustic wave propagation.
Figure 12:
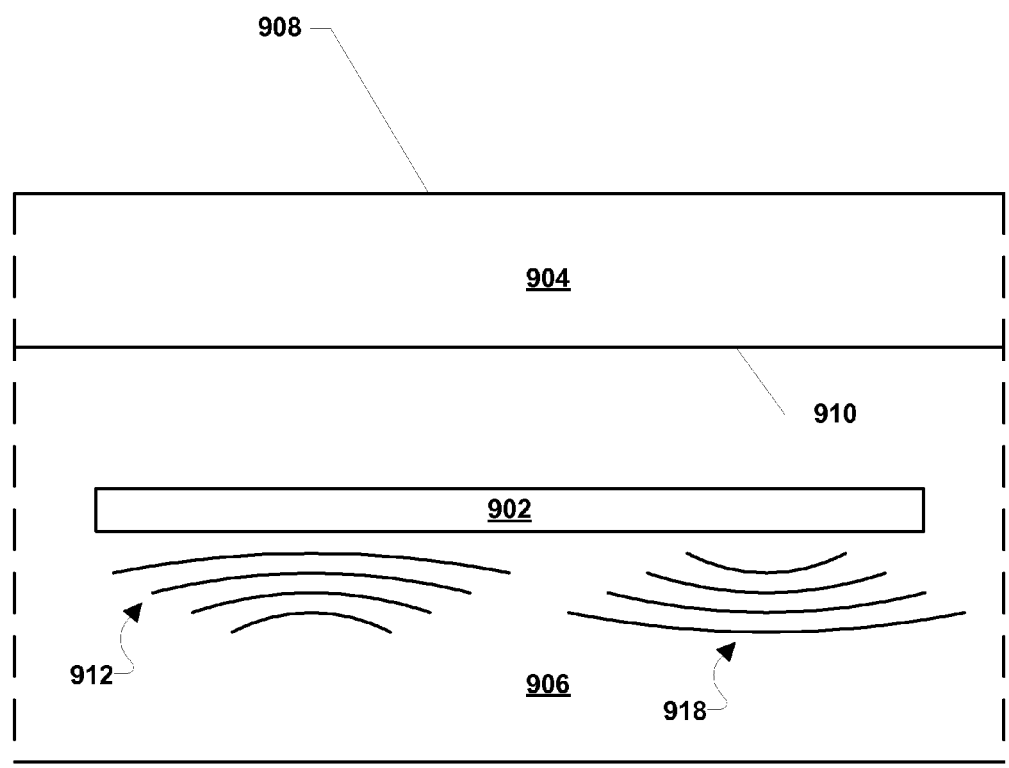
FIG. 12 illustrates a fourth embodiment configuration of an acoustic tag positioned in the fluid within a fluid container including acoustic wave propagation.

FIG. 11 illustrates an embodiment in which the acoustic transmitter/receiver 902 is positioned on inside surface 910 of the fluid containing structure 904. FIG. 12 illustrates an embodiment in which the acoustic transmitter/receiver 902 may be free floating and or suspended within the fluid 906. In the embodiments illustrated in FIGS. 11 and 12, sound does not have to travel through the fluid containing structure 904 to interact with the acoustic transmitter/receiver 902. Positioning the acoustic transmitter/receiver 902 within the fluid 906 allows the acoustic waves 912 within the fluid to directly interact with the acoustic transmitter/receiver 902, and allows the acoustic transmitter/receiver to generate acoustic waves 918 directly in the fluid. Thus, positioning the acoustic transmitter/receiver 902 within the fluid 906 may improve acoustic coupling between the acoustic transmitter/receiver 902 and the fluid, since sound does not need to transit the container structure 904.

FIGS. 13-17 illustrate various embodiments of an acoustic modem 1316 which may be suitable for communicating with both active and passive acoustic tags. In an embodiment, an acoustic modem 1316 may be a standalone device that may be coupled to a pump, meter or valve. In another embodiment, an acoustic modem may be a module coupled to or implemented within another device, such as a pump, meter or valve. In another embodiment, the hardware elements of an acoustic modem 1316 may comprise elements of another device. The acoustic modem 1316 may be suitable for operation with any number of fluid mediums and fluid applications. However, for ease of description, FIGS. 13-17 are described below with reference to an IV pump embodiment in which the acoustic modem 1316 is in acoustic communication with a fluid line 1312 containing a fluid 1314 dispensed from an IV bag.

Figure 13:
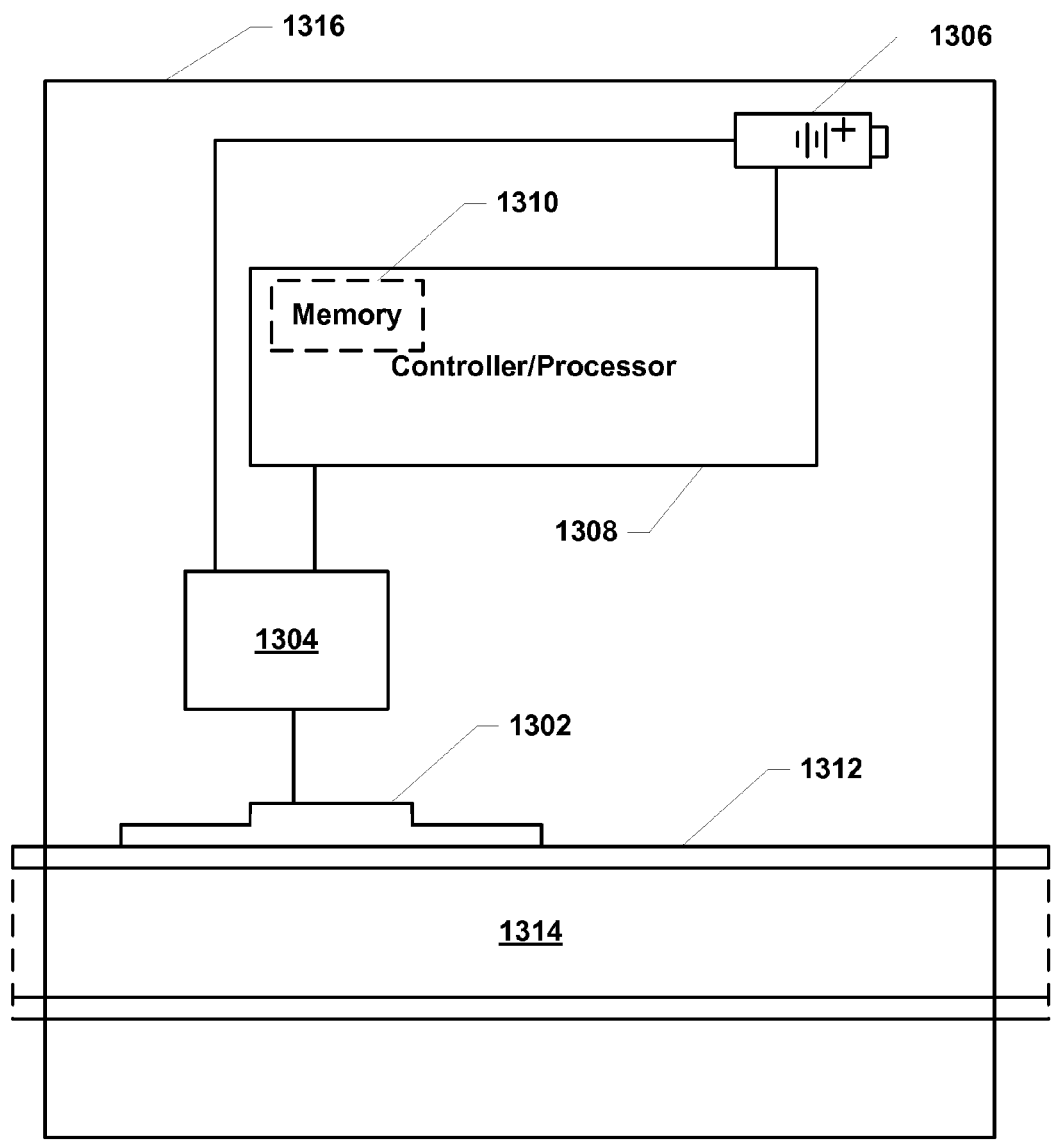
FIG. 13 is a component block diagram of an acoustic modem unit according to a first embodiment.

FIG. 13 illustrates a first embodiment of an acoustic modem 1316 that includes a piezoelectric transducer 1302 which may be placed in contact with or otherwise coupled to a fluid line 1312 through which sound is to be transmitted and/or received. The piezoelectric transducer 1302 may be coupled to an signal modifying circuit 1304 which is coupled to a controller 1308 and a power source 1306. The controller 1310 may be coupled to the power source 1306 and may include a memory 1310.

In operation, the embodiment of an acoustic modem 1316 illustrated in FIG. 13, may function as follows. An acoustic wave within the fluid 1314 may pass through the fluid line 1312 and into the piezoelectric transducer 1302. The piezoelectric transducer 1302 converts the mechanical vibrations into electrical signals which are modified (e.g., amplified and/or converted to digital format) by an signal modifying circuit 1304 and passed to the controller 1308. Either of the signal modifying circuit 1304 or the controller 1308 may include an analog-to-digital converter and/or DSP which converts the received electrical signals into digital format that can be processed by the controller 1308. The controller 1308 may compare the received signals to signal characteristics, identifiers, symbols or other information stored in the memory 1310 part of determining a proper response to the signals. For example, if the information encoded within received acoustic signals includes an identifier for either the fluid or the fluid container (e.g., a serial number or fluid code) the controller 1308 may determine whether the received identifier is what was expected or is acceptable. This operation may involve simple table lookup operation in which the controller uses the information encoded within the received signal to look up an appropriate action within a data or logic table stored in the memory 1310. Such a data or logic table, or other executable instructions, may be used by the controller 13 to identify an operation to be performed automatically in response to the received acoustic signals. In many next generation hospital concepts, the IV pump would not make such a decision by itself, but rather would forward the data to the hospital computers which would make the decision and transmit an activation or alarm command to the pump. For example, if an identifier included within the received acoustic signal matches an expected code or value, indicating that the appropriate fluid container has been connected to a fluid pump, meter, or dispenser, the determined operation may be to proceed with pumping or metering of the fluid. However, if the identifier included within the received acoustic signal does not match the expected code or value, the determined operation may be to suspend pumping or close the valve, and sound an alarm to alert an operator that an inappropriate fluid container has been connected. The embodiment illustrated in FIG. 13 is only able to receive acoustic signals, and is not configured to also generate acoustic signals.

Figure 14:
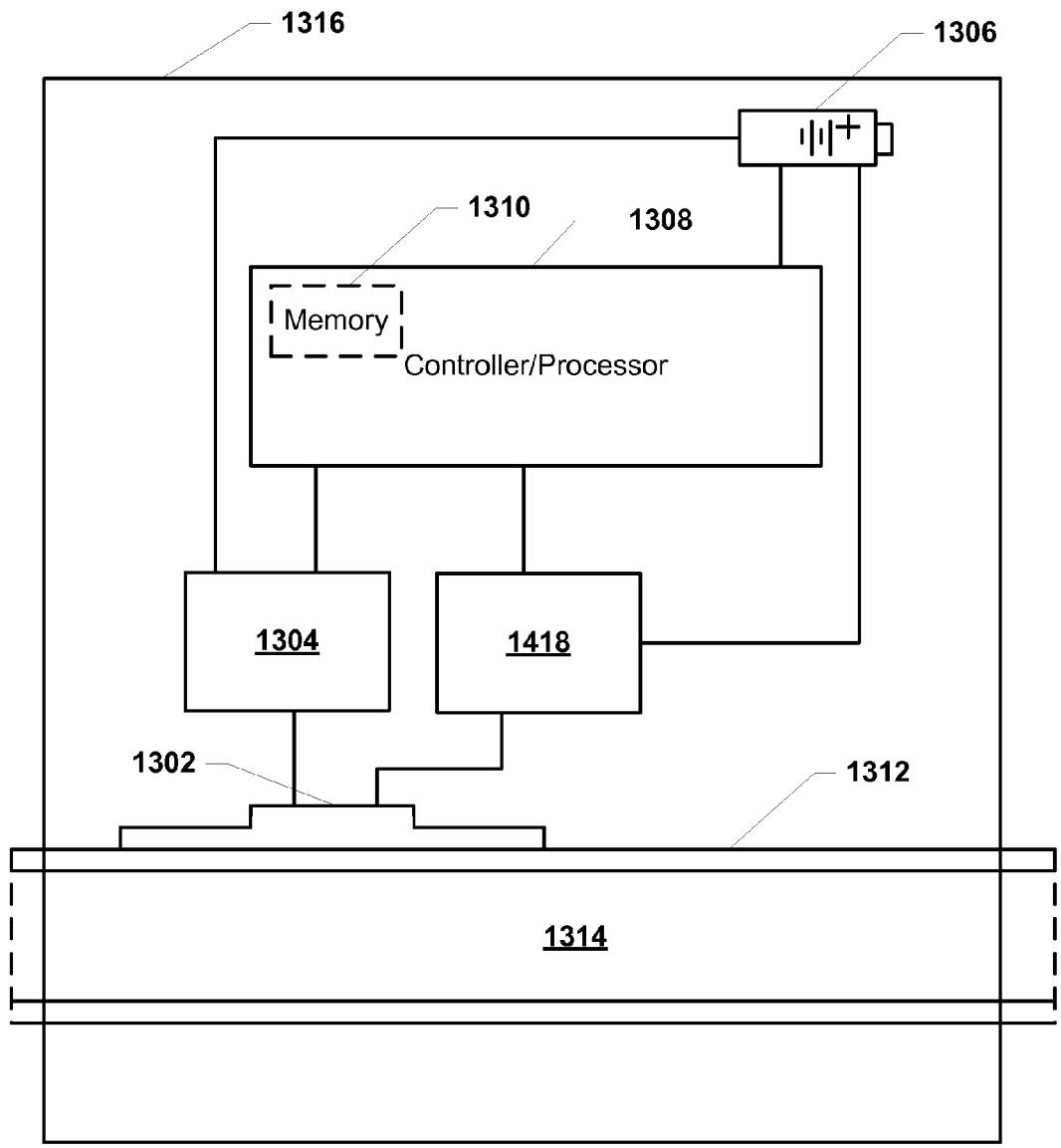
FIG. 14 is a component block diagram of an acoustic modem unit according to a second embodiment.

FIG. 14 illustrates a second embodiment of an acoustic modem 1316 that is similar to the first embodiment illustrated in FIG. 13, with the addition of a pulse generator 1418 which may be coupled to the controller 1308, power source 1306, and piezoelectric transducer 1302. The addition of the pulse generator 1418 enables the acoustic modem 1316 to transmit acoustic signals into the fluid line 1312 and fluid 1314. In operation, the controller 1308 may output signals to the pulse generator 1418 which generates electrical signals which cause the piezoelectric transducer 1302 to generate acoustic waves in the fluid line 1312 and fluid 1314. The signals provided by the controller 1308 may encode information, such as a query code, that a receiving acoustic tag 202 may interpret as an activation code. Alternatively, the acoustic signals generated by the piezoelectric transducer 1302 may be of a particular frequency or frequencies that a receiving acoustic tag 202 may recognize as an activation code.

Figure 15:
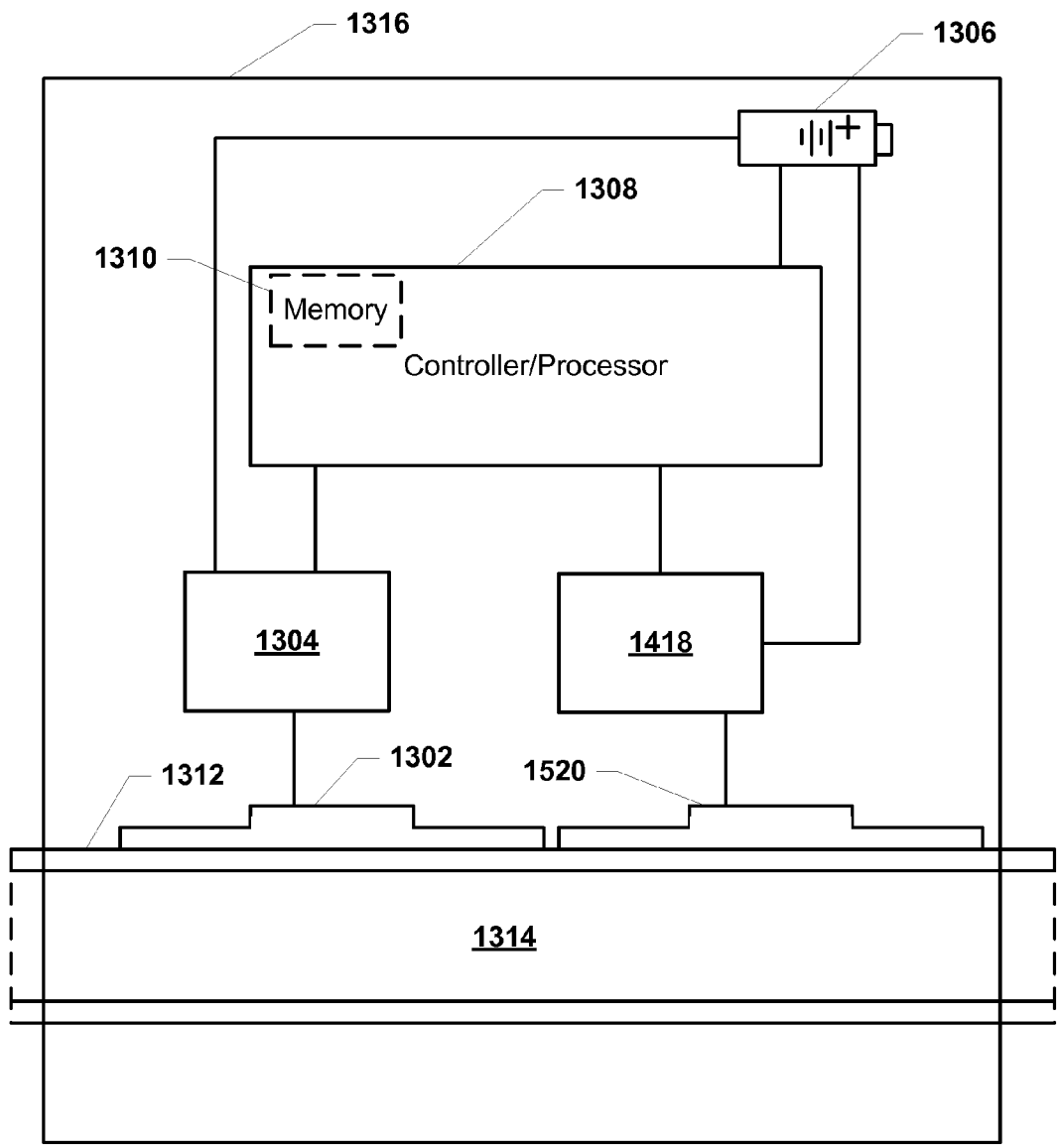
FIG. 15 is a component block diagram of an acoustic modem unit according to a third embodiment.

FIG. 15 illustrates a third embodiment of an acoustic modem 1316 that is similar to the second embodiment illustrated in FIG. 14, with the addition of a second piezoelectric transducer 1520 which may be coupled to the pulse generator 1418 and the fluid line 1312. In this embodiment, the pulse generator 1304 may not be coupled to the first piezoelectric transducer 1302. The inclusion of two piezoelectric transducers 1302 and 1520 allows one piezoelectric transducer to be dedicated to receiving acoustic signals, while the other piezoelectric electric transducer generates acoustic waves. This embodiment may enable simultaneous transmission and reception of acoustic signals.

Figure 16:
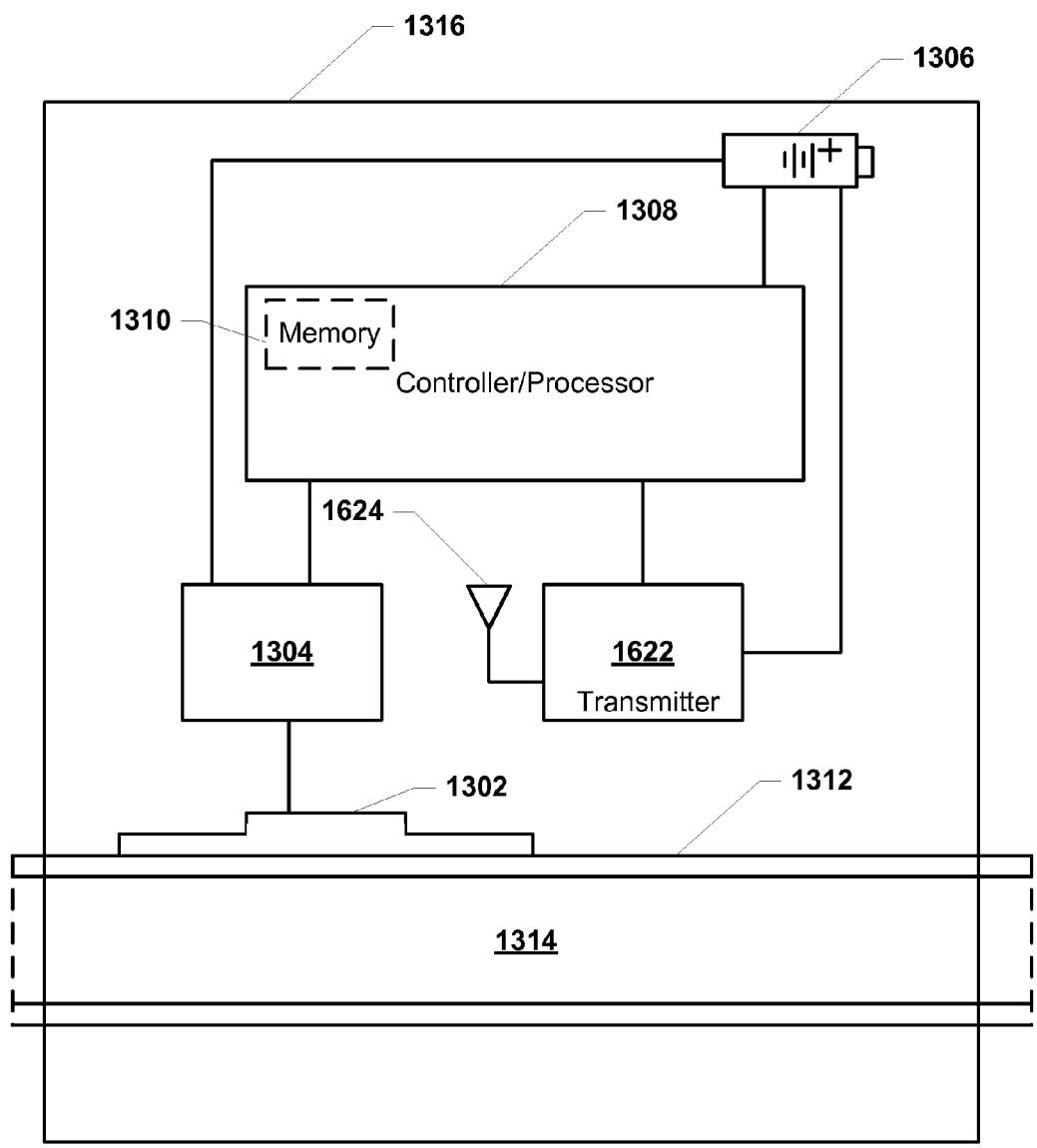
FIG. 16 is a component block diagram of an acoustic modem unit according to a fourth embodiment.

FIG. 16 illustrates a fourth embodiment of an acoustic modem 1316 that is similar to the first embodiment illustrated in FIG. 13, with the addition of an RF transmitter 1622 coupled to an antenna 1624, the controller 1308 and a power source 1306. The addition of the RF transmitter 1622 may enable the acoustic modem 1316 to transmit queries using radio frequencies. As an example the acoustic modem 1316 may use Bluetooth or RFID to query an IV bag providing fluid 1314 through the fluid line 1312. In this manner the RF query signal sent from the acoustic modem 1316 may trigger an acoustic tag to generate acoustic signals that are conducted through the fluid 1314 within the IV bag and the fluid line 1312 as described above. The acoustic modem 1316 may identify the fluid 1314 and take appropriate actions based on the received acoustic signals as described above.

Figure 17:
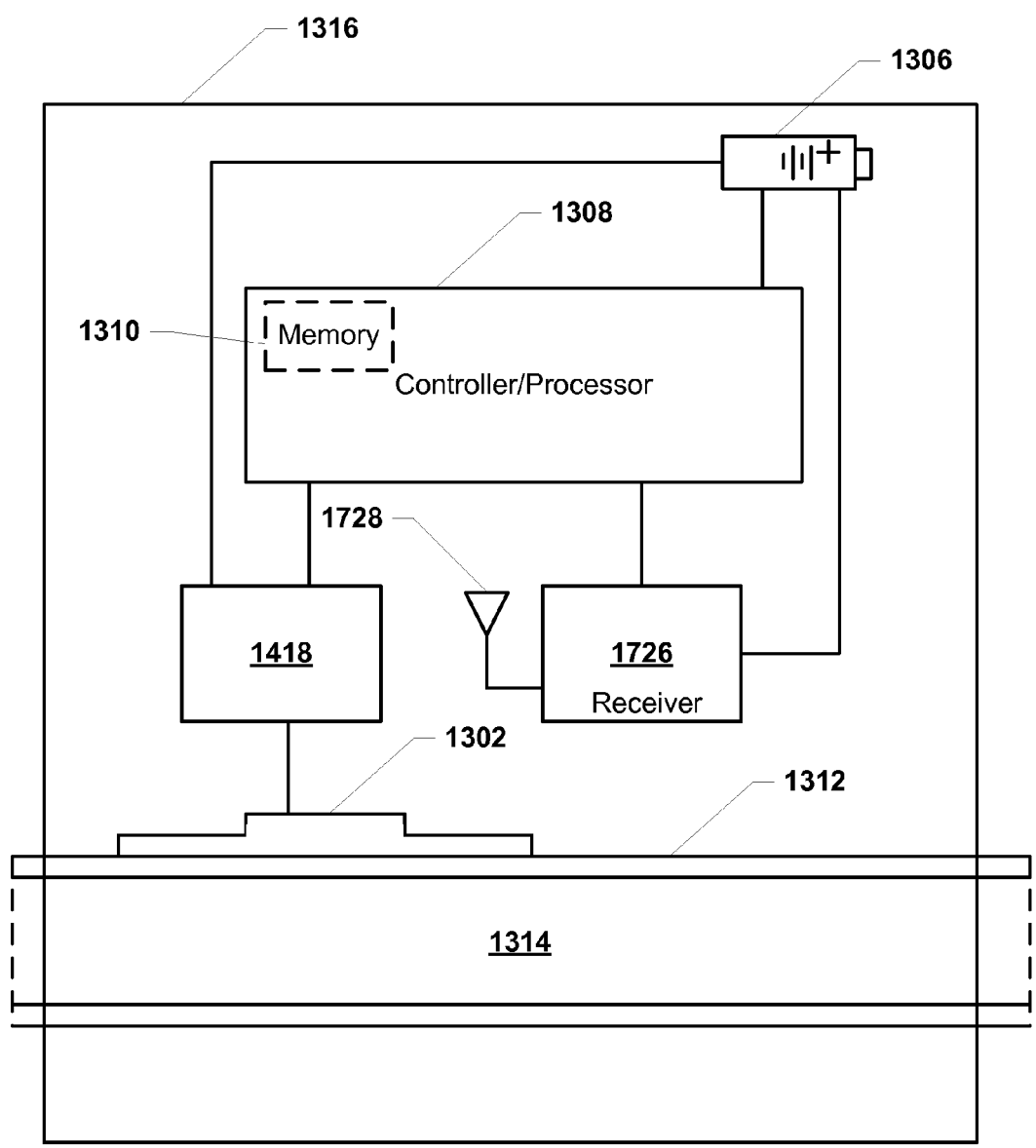
FIG. 17 is a component block diagram of an acoustic modem unit according to a fifth embodiment.

FIG. 17 illustrates a fifth embodiment of an acoustic modem 1316 that is similar to the second embodiment illustrated in FIG. 14, with the addition of an RF receiver 1726 coupled to an antenna 1728 and the controller 1308, and removal of the signal modifying circuit 1304. The addition of the RF receiver 1726 may allow the acoustic modem 1316 to receive RF signals from appropriately configured acoustic tags, such as the Bluetooth or RFID signals. In operation, the acoustic modem 1316 may transmit acoustic query signals into the fluid line 1312 and fluid 1314 coupled to an IV bag. As described above with reference to FIGS. 8A and 8B, an appropriately configured acoustic tag may recognize the acoustic query signal event and in response transmit an RF signal encoding identification information (and/or other information) which may be received by the antenna 1728 and RF receiver 1726. The received RF signals processed by the RF receiver 1726 may be passed to the controller 1308 which may use the information contained within the signals to take appropriate action.

Figure 18:
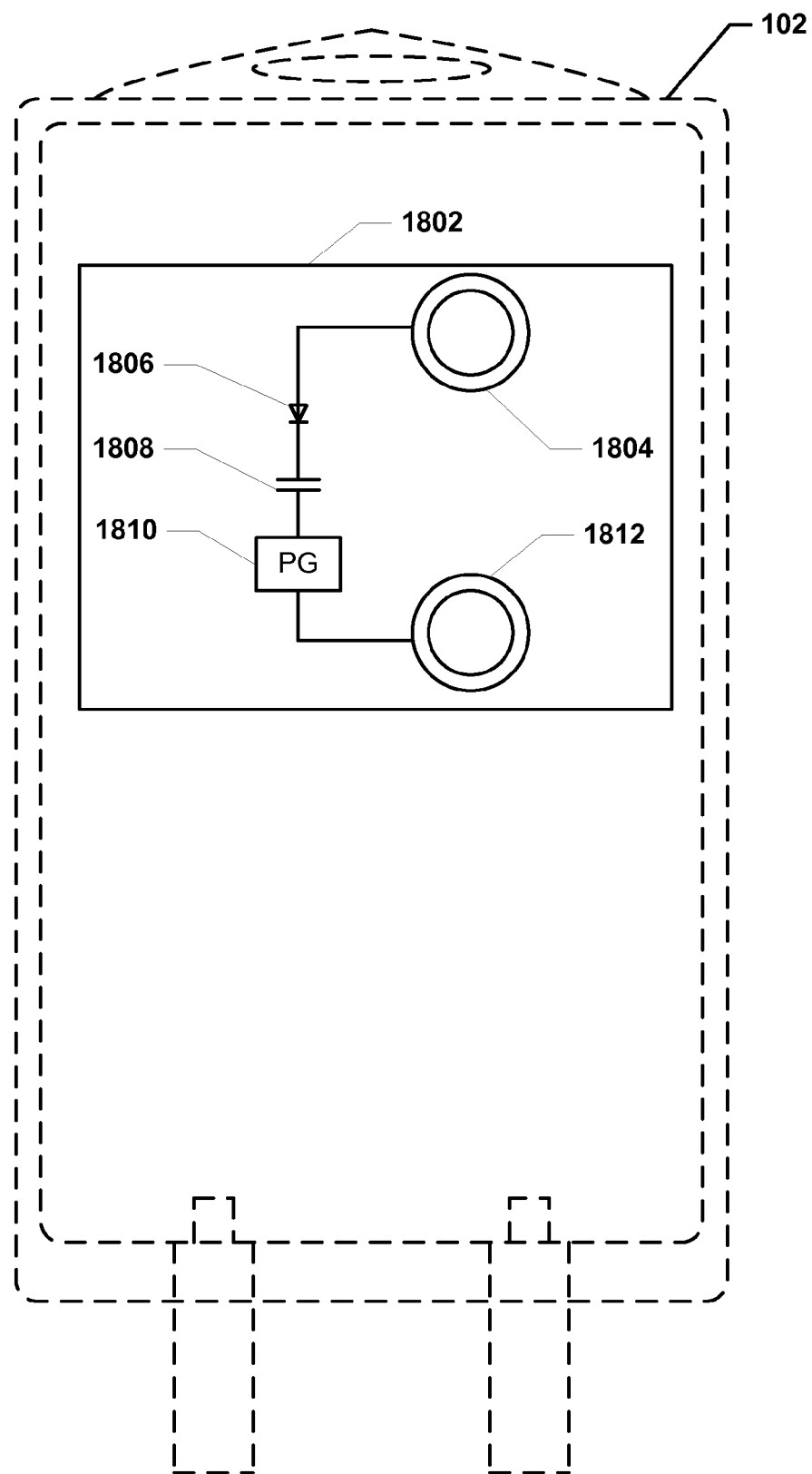
FIG. 18 is a component block diagram of a passive acoustic tag according to a first embodiment.
Figure 19:
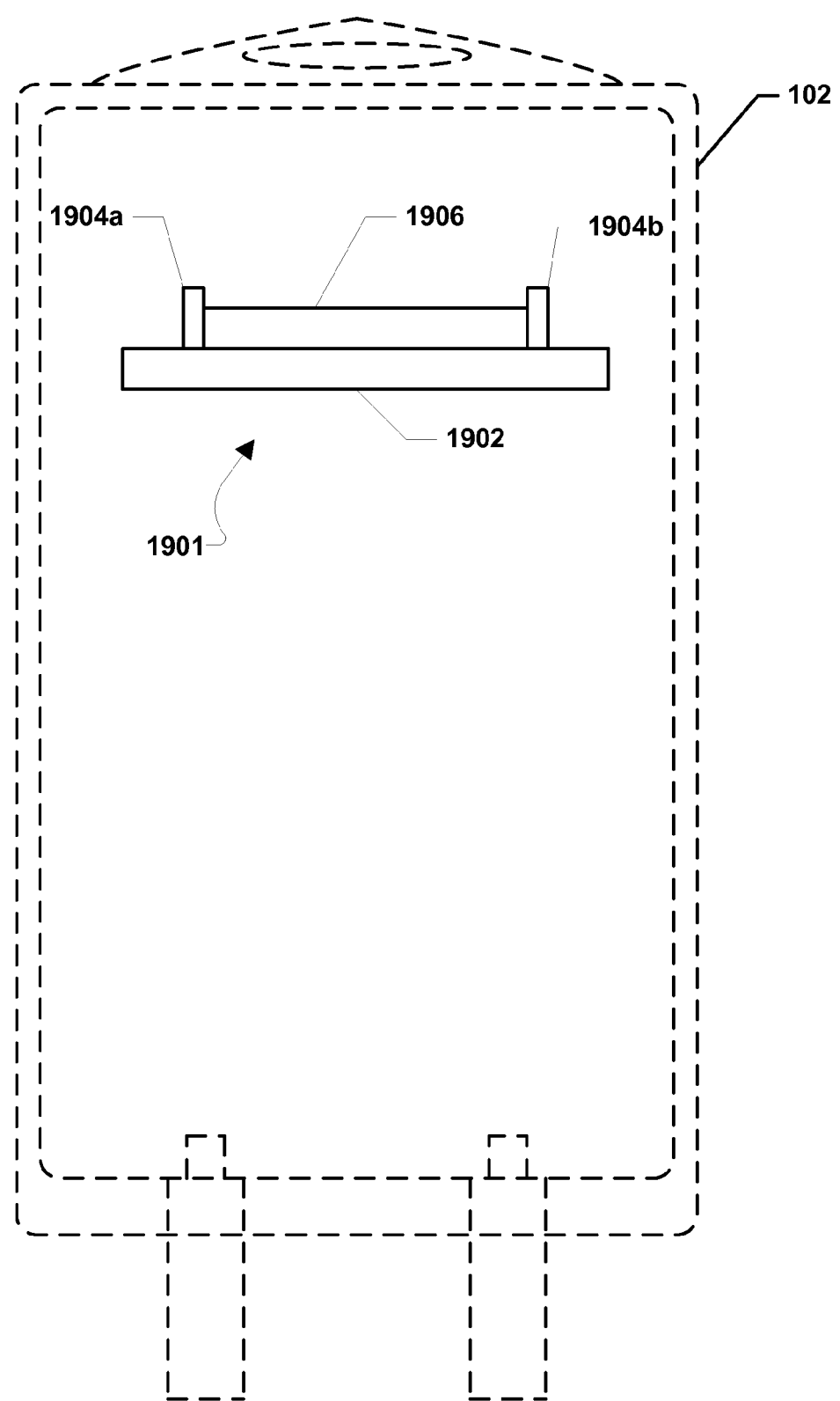
FIG. 19 is a component block diagram of a passive acoustic tag according to a second embodiment.
Figure 20:
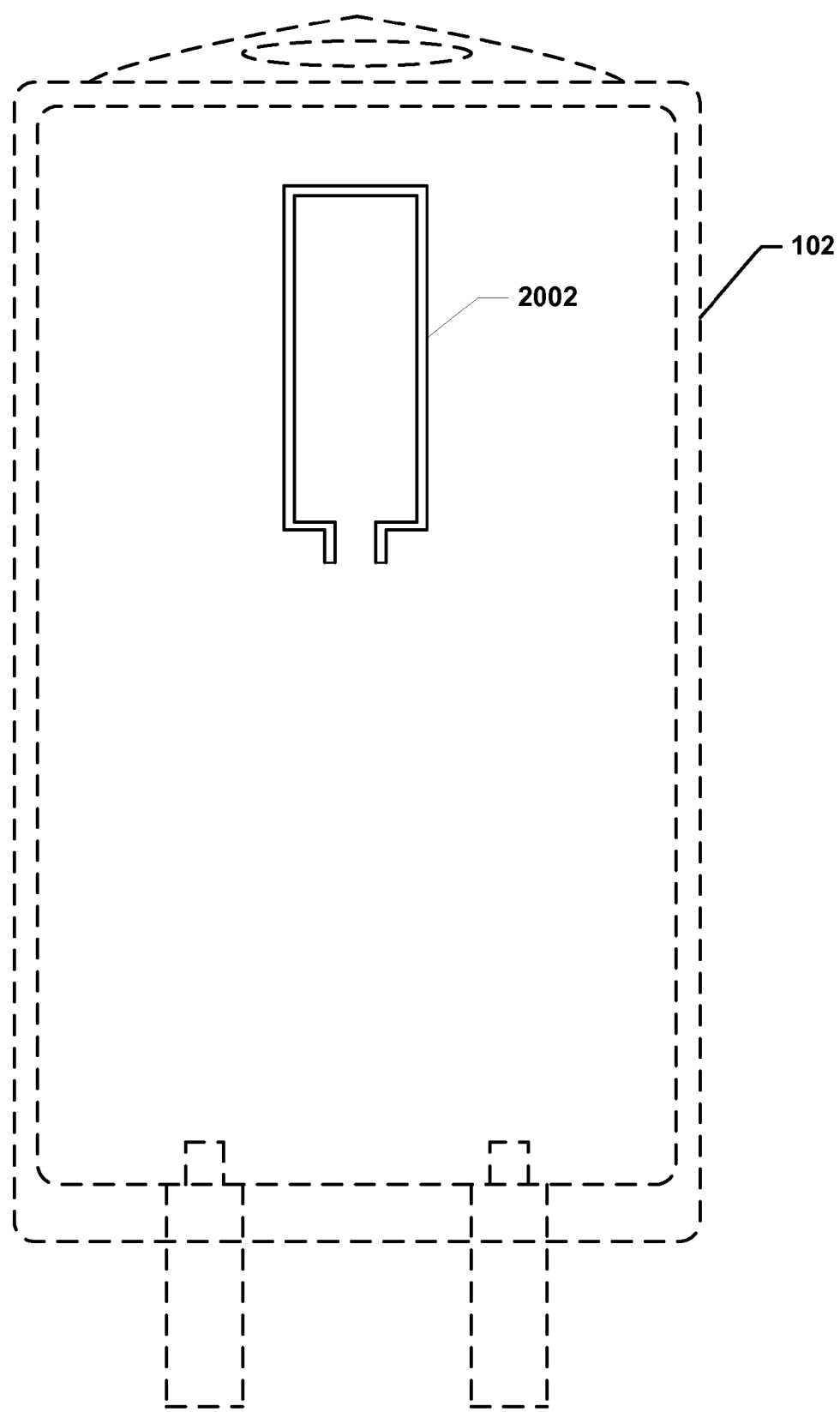
FIG. 20 is a component block diagram of a passive acoustic tag according to a third embodiment.

FIGS. 18-20 illustrate various embodiments of passive acoustic tags. The term passive acoustic tags refers to acoustic tags that have no power source, and thus require an incident acoustic signal in order to produce animated acoustic signals. Passive acoustic tags may be less expensive to manufacture and have extended storage life since they do not require a battery. Since they do not include a battery, passive acoustic tags may be better suited for certain fluid applications because the risk of contamination from battery leakage is eliminated. Also, passive tags which do not generate electrical current may be preferred in applications in which fluid is highly flammable or conductive.

FIG. 18 illustrates a first embodiment of a passive acoustic tag 1802 that harvests energy within a received acoustic signal to power an acoustic transmitter. The passive acoustic tag 1802 may include a first piezoelectric transducer 1804 that is coupled to an energy harvesting circuit. In an embodiment, the energy harvesting circuit may include a diode 1806 which is coupled to a capacitor 1808. In an alternative embodiment (not shown) the energy harvesting circuit may include an inductor. The energy harvesting circuit, such as the capacitor 1808 may be coupled to a pulse generator 1810 which is coupled to a second piezoelectric transducer 1812. In operation, energy in an acoustic signal incident on the first piezoelectric transducer 1804 may be harvested by storing electrical currents generated by the first piezoelectric transducer 1804 in response to received acoustic waves in an energy harvesting circuit, such as the diode 1806 and capacitor 1808 elements. Current pulses generated by the piezoelectric transducer 1804 will typically be alternating current, so the diode 1806 ensures only positive current flows to the capacitor 1808, thereby enabling the capacitor 1808 to be charged. The charge stored in the capacitor 1808 can be used by the pulse generator 1810 to generate pulses that are applied to the second piezoelectric transducer 1812, which cause the second piezoelectric transducer 1812 to produce acoustic signals in the fluid. In an embodiment, the pulse generator 1810 may include circuitry to generate pulses at a particular frequency or encoding information that can be recognized by an acoustic modem as described herein.

FIG. 19 illustrates a second embodiment of a passive acoustic tag 1901 that includes a simple acoustic oscillator, such as a base 1902 with two upright posts 1904a and 1904b a tensioned filament 1906 connected there between. The base 1902, upright posts 1904a and 1904b, and tensioned filament 1906 may be considered an acoustic reflective assembly. The tensioned filament 1906 may be configured in size and tension to resonate at a predetermined frequency. The passive acoustic tag 1901 may be placed within the fluid in a fluid container. In operation, when a fundamental frequency of the tensioned filament 1906 matches a frequency of harmonic of an acoustic wave in the fluid, the tensioned filament 1906 will resonate sympathetically, thereby creating acoustic waves in the fluid at the predetermined frequency. These sympathetic acoustic waves at the predetermined frequency may be recognized by an acoustic modem and used to identify the passive acoustic tag 1901 or the fluid container. Instead of a tensioned filament, the acoustic oscillator may be a solid structure, such as a tuning fork or bell that functions in a similar manner.

FIG. 20 illustrates an embodiment of a passive acoustic tag 2002 in the form of a cylinder open at one end and closed at another configured to operate like a Helmholtz resonator to remove or amplify a desired frequency. The acoustic tag 2002 may be considered an acoustic reflective assembly. In operation, a broad spectrum of acoustic frequencies may be transmitted into the fluid within a fluid container. The acoustic tag 2002 may be configured to remove a particular frequency. The particular frequency would be canceled and not reflected back from the fluid container. An acoustic modem monitoring the reflected frequencies received from the fluid container may recognize from the spectrum of the received acoustic signals that the particular frequency is present in a lower altitude than the other frequencies, and thereby identify the passive acoustic tag 1901 or the fluid container.

Figure 21:
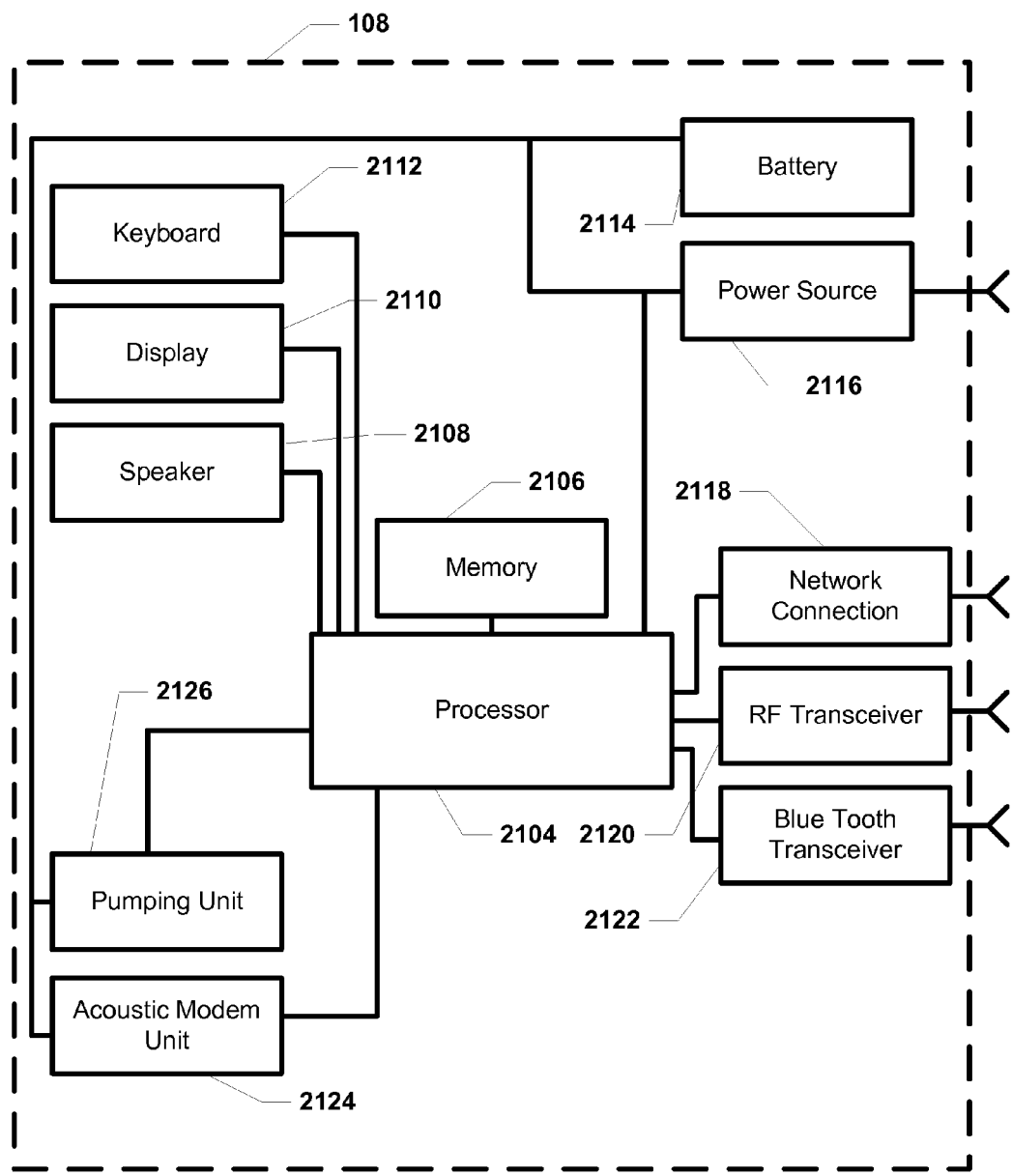
FIG. 21 is a component block diagram of a fluid pumping unit suitable for use in an embodiment.

FIG. 21 illustrates example components which may be within an embodiment IV pump 108. The IV pump 108 may include a pumping unit 2126 configured to pump fluid that is coupled to a processor 2104 and battery 2114. The processor 2104 may be configured to control the operation of the pumping unit 2126. An acoustic modem unit 2124 may be coupled to the processor 2104 and the battery 2114. The IV pump 108 may additionally contain a memory 2106 coupled to the processor 2104. The acoustic modem unit 2124 may be controlled by the processor 2104, and may communicate information obtained from received acoustic signals to the controller 2104. A keyboard 2112, display 2110, and speaker 2108 may be coupled to the processor 2104 and configured to provide input/output capabilities for the IV pump 108. The IV pump 108 may also include a network connection 2118 enabling the IV pump 108 to connect to a data network. The IV pump 108 may also include an RF transceiver 2120 and/or a Bluetooth transceiver 2122 configured to enable the IV pump 108 to wirelessly communicate with other devices. The IV pump 108 may include an input for an external power source 2116 allowing the IV pump 108 to operate via external power.

Figure 22:
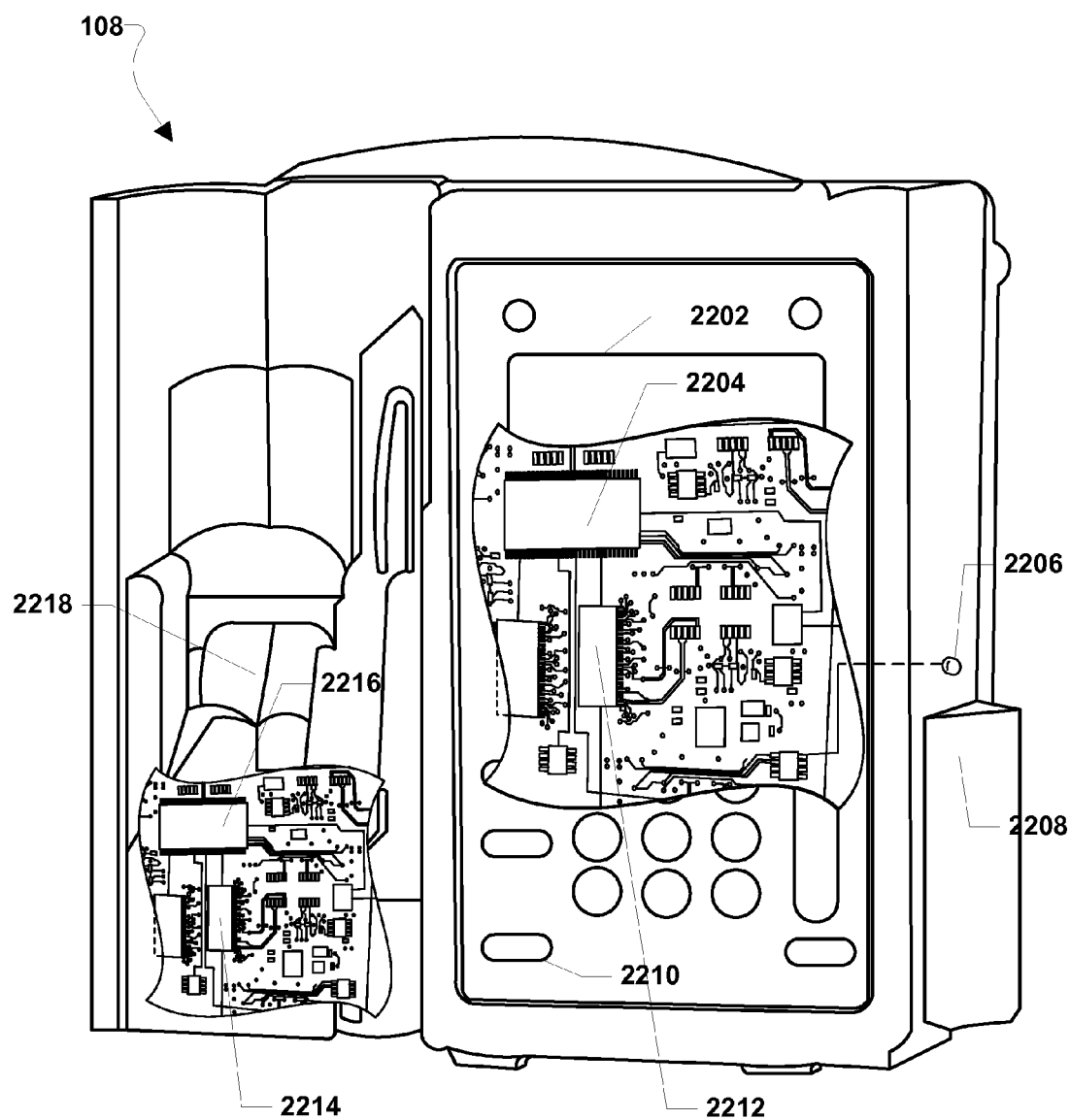
FIG. 22 is a cutaway perspective view of an IV fluid pumping unit embodiment.

FIG. 22 illustrates an embodiment IV pump 108 showing additional aspects and components. The IV pump 108 may include memory 2212 coupled to a processor 2204 is configured to control operations of the pump. The pumping unit 2218 of the IV pump 108 may include an acoustic modem which may include a processor 2216 coupled to a memory

2214. Fluid lines to be pumped may be coupled to the pumping unit 2218 and thereby to the acoustic modem. Additionally, the IV pump 108 may contain an on/off button 2210, a display 2202, a battery pack 2208, and a network connection 2206.

Figure 23:
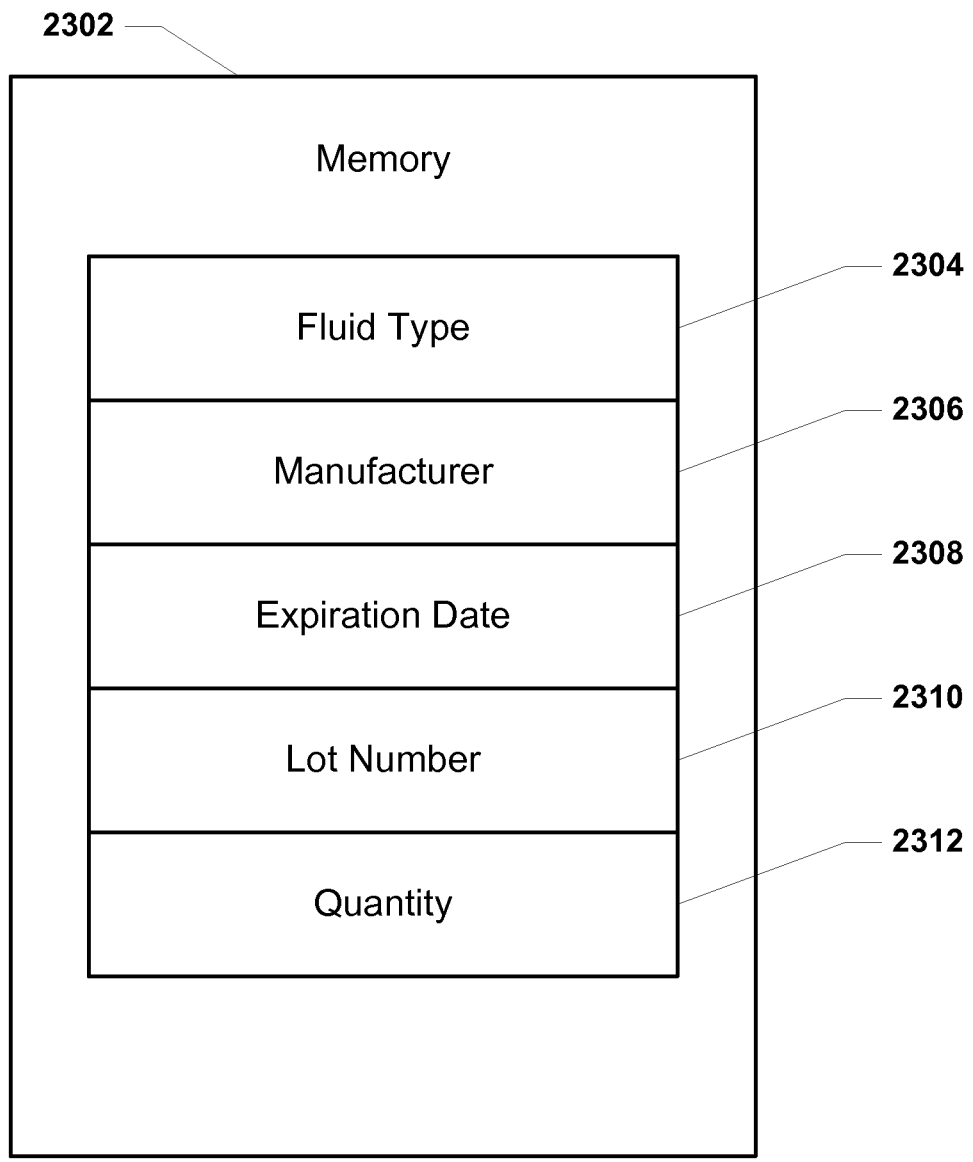
FIG. 23 is a data structure diagram of example elements of fluid information which may be stored in a memory of an acoustic tag.

FIG. 23 is a data structure diagram illustrating potential elements of fluid information which may be stored in a memory 2302 resident in an acoustic tag in the various embodiments. The memory 2302 may contain elements of information related to the fluid type 2304 stored in a fluid container, the manufacturer 2306 of the fluid, acoustic tag, and/or fluid container, the expiration date 2308 of the fluid, the lot number 2310 of the fluid container, and a quantity 2312 of fluid stored in the fluid container. In various embodiments, more or less information may be stored in the memory of an acoustic tag. All or part of the information available in the memory 2302 may be encoded by the acoustic tag in emitted acoustic signals.

Figure 24:
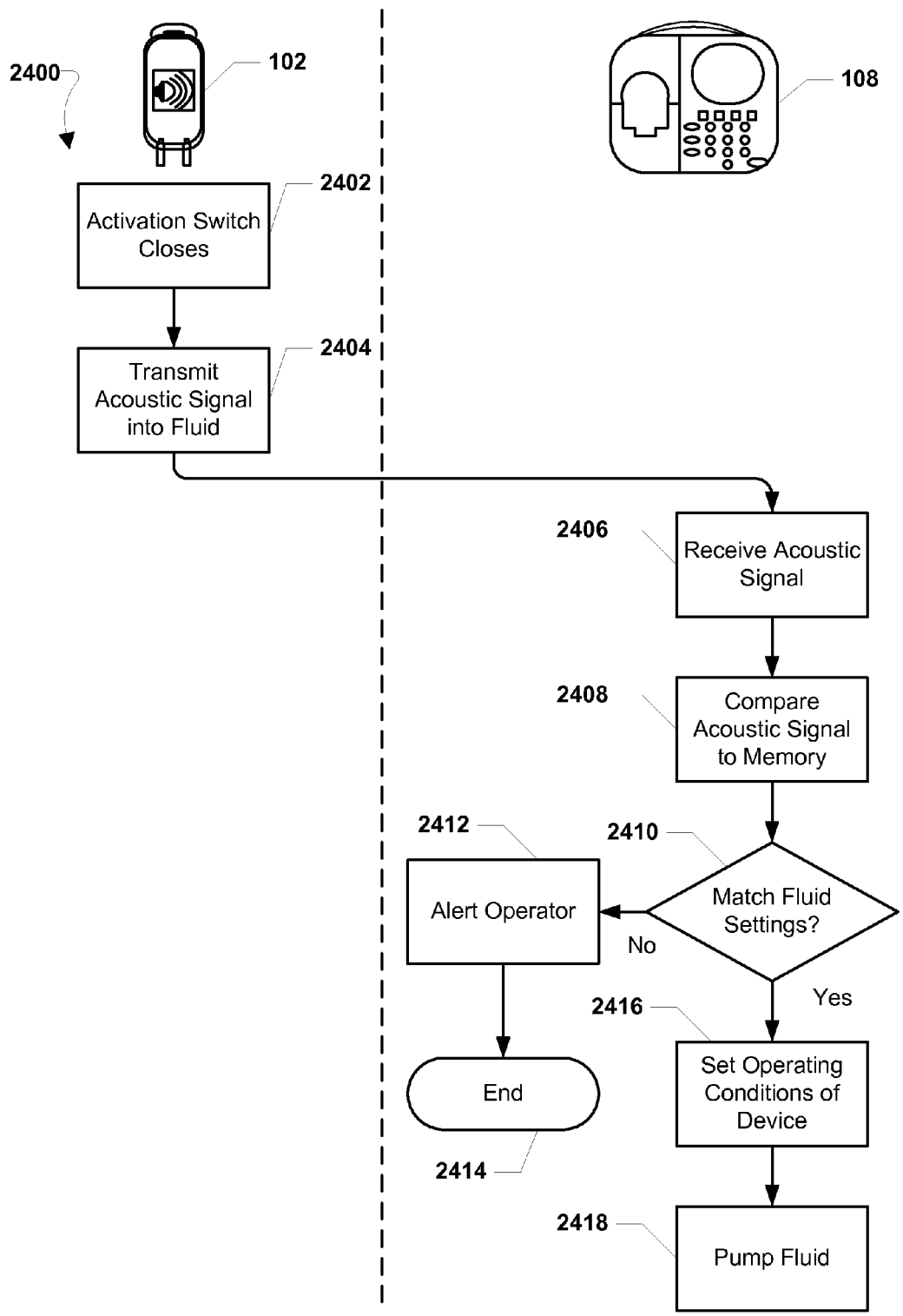
FIG. 24 is a process flow diagram illustrating a first embodiment method for fluid identification using acoustic communication through the fluid.

FIG. 24 illustrates an embodiment method 2400 for communicating fluid identification (or other information) between an IV bag 102 employing an acoustic tag and an IV pump 108 employing an acoustic modem. At block 2402, an activation switch may be closed on the acoustic tag, such as by a user pressing a button, pulling a tag or other action. At block 2404, the acoustic tag begins transmitting an acoustic signal into the fluid within the IV bag 102. At block 2406, the acoustic modem of the IV pump 108 receives the acoustic signal. At block 2408 the IV pump 108 modem modulates the received acoustic signal to obtain information included within the signal or to transform the signal into digital information that it compares to information or signal characteristics stored in a memory. The memory may be within the acoustic modem or a separate memory. As an example, the signal characteristics may include frequency or amplitude characteristics of a particular type or model of acoustic tag. Those frequency or amplitude characteristics may be associated with specific types of fluid containers, fluids or fluid settings stored in the memory.

At determination block 2410, the IV pump 108 may determine whether the identified fluid matches the fluid settings. If the identified fluid doesn't match (i.e., determination block 2410="No"), at block 2412 the IV pump 108 may activate an alarm to alert an operator of the IV pump 108 that the fluid does not match the current fluid setting, and may end pumping operations at block 2414. As part of determination block 2410, the IV pump 108 may also or alternatively compare the identified fluid to a listing of patient allergens or approved medications, so that if the fluid matches a proscribed fluid or medication (i.e., a fluid or medication to which the patient is allergic), the pump may end pumping operations at block 2414. At block 2412, the IV pump 108 may also activate an alarm to alert the operator to the allergy condition. The listing of patient allergens, proscribed medications and/or approved medications may be stored in a hospital database accessible by a controller of the IV pump 108 (e.g., via a wireless communication link) or stored in local memory accessible by the pump controller.

If the fluid matches the fluid settings (i.e., determination block 2410="Yes"), at block 2416 the IV pump 108 may set the operating conditions for the pumping unit to administer the identified fluid, and at block 2418 begin pumping the fluid.

As an example, a table in memory may associate saline with a 100 Hz frequency acoustic signal. If the IV pump 108 has been set by an operator to pump a saline solution, and the acoustic modem detects a 100 Hz frequency signal, the IV pump 108 may proceed with pumping operations. However, if a 100 Hz frequency signal is not detected, the IV pump 108 may cease pumping operations and sound an alarm.

Figure 25:
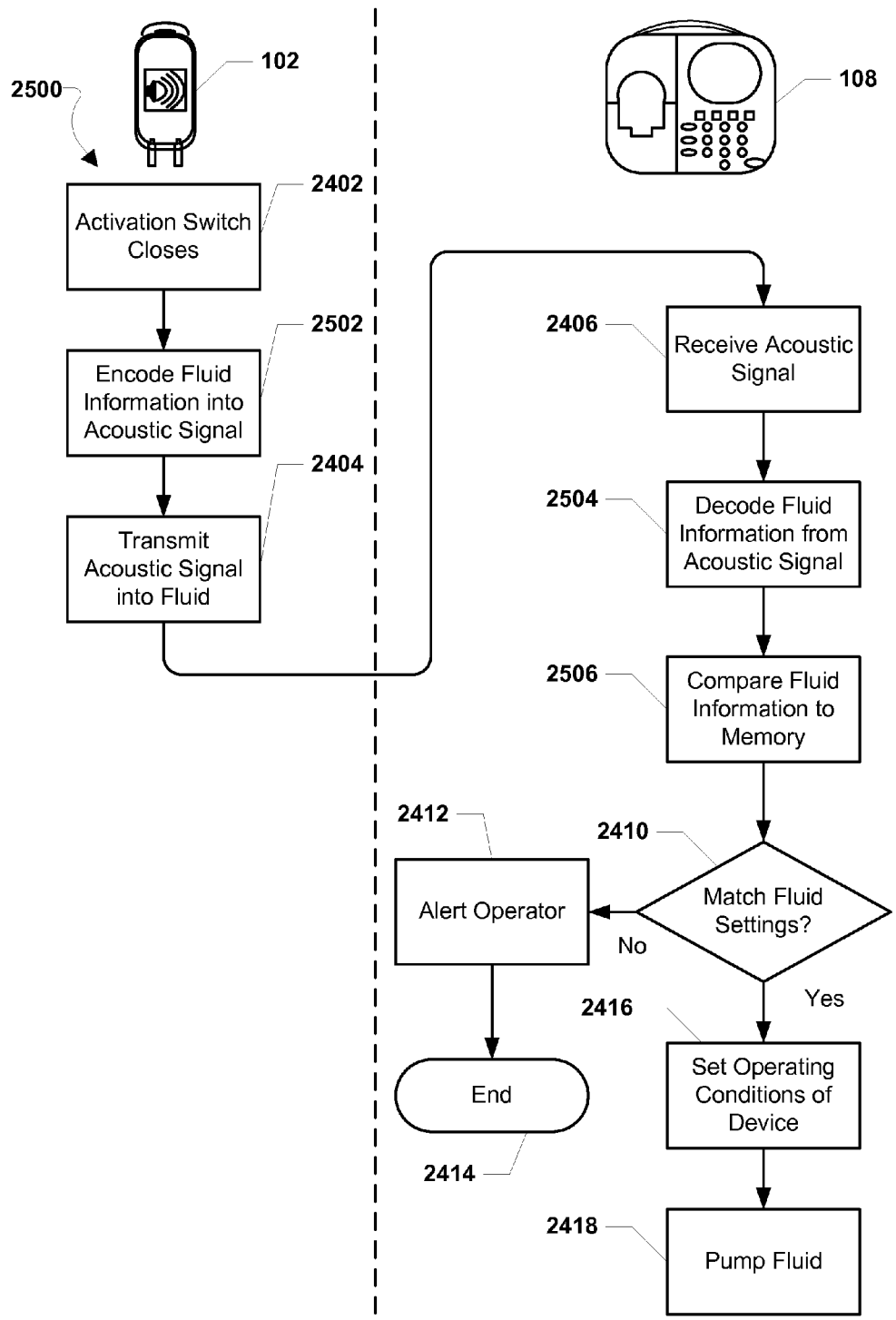
FIG. 25 is another process flow diagram illustrating a second embodiment method for fluid identification using acoustic communication through the fluid.

FIG. 25 illustrates another embodiment method 2500 similar to that described above with relation to FIG. 24, except that at block 2502 the acoustic tag at the IV bag 102 encodes fluid information into the acoustic signal. As an example, the acoustic tag may encode a signal with information directly identifying the fluid contained in the IV bag 102, such as a signal identifying the fluid as saline.

At block 2504, the IV pump 108 demodulates the received acoustic signal to obtain the fluid information encoded within the acoustic signal. In block 2506, the fluid information obtained from the received acoustic signal may be compared to the fluid information stored in memory. The method 2500 may then proceed from block 2410 as described above with reference to FIG. 24.

Figure 26:
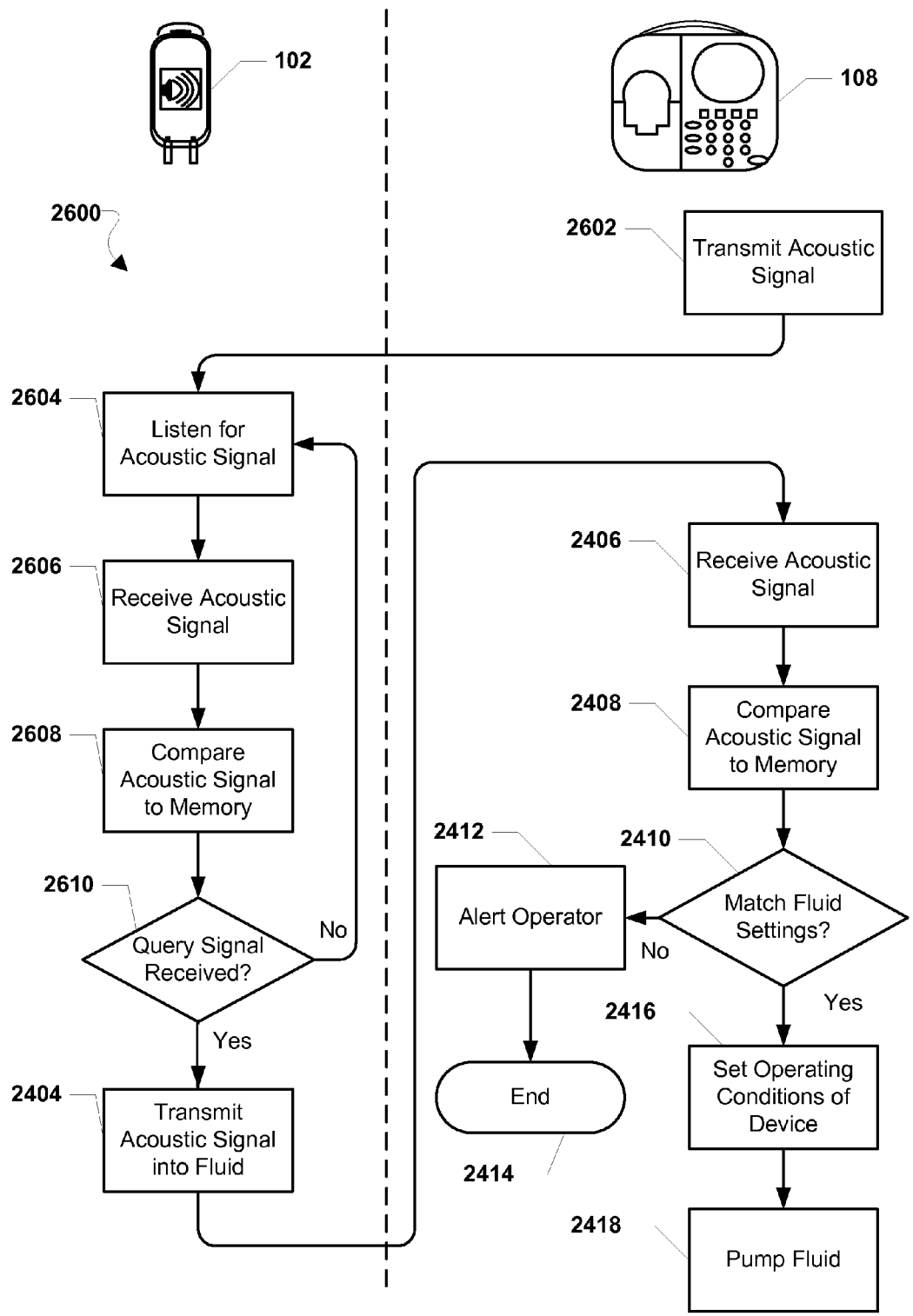
FIG. 26 is another process flow diagram illustrating a third embodiment method for fluid identification using acoustic communication through the fluid.

FIG. 26 illustrates another embodiment method 2600 similar to that described in FIG. 24, except that at block 2602 the IV pump 108 initiates communications with the acoustic tag 102 by transmitting an acoustic signal via the fluid line to the IV bag 102. At block 2604, an acoustic tag at the IV bag 102 listens for an acoustic signal. At block 2606, the acoustic tag receives the acoustic signal. At block 2608, the acoustic tag may compare the received acoustic signal to a memory on the acoustic tag in order to recognize and interpret the received acoustic signal. As an example the acoustic tag may compare the frequency of the received signal to a frequency for query signals stored in the memory. At determination block 2610, the acoustic tag may determine if the received signal is a query signal. If the received signal is not a query signal (i.e., determination block 2610="No"), the acoustic tag returns to block 2604 to continue listening for acoustic signals. When the acoustic tag determines that the signal received is a query signal (i.e., determination block 2610="Yes"), the acoustic tag may proceed at block 2404 as described above with reference to FIG. 24 and method 2400.

Figure 27:
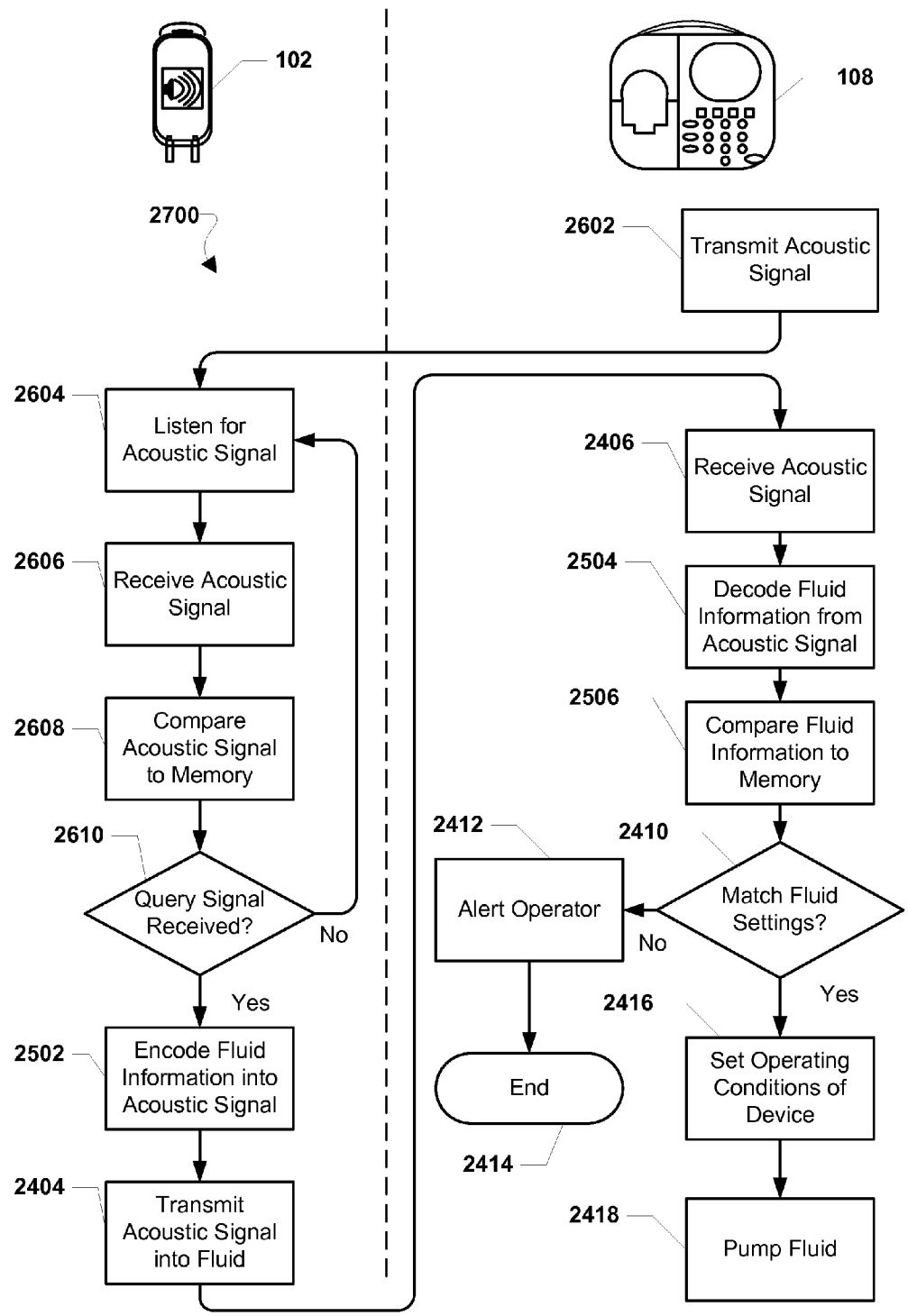
FIG. 27 is another process flow diagram illustrating a fourth embodiment method for fluid identification using acoustic communication through the fluid.

FIG. 27 illustrates another embodiment method 2700 similar to that described in FIG. 26, except that if a query signal is received (i.e., determination block 2610="Yes"), the acoustic tag may proceed to block 2502 as described above with reference to FIG. 25 and method 2500.

Figure 28:
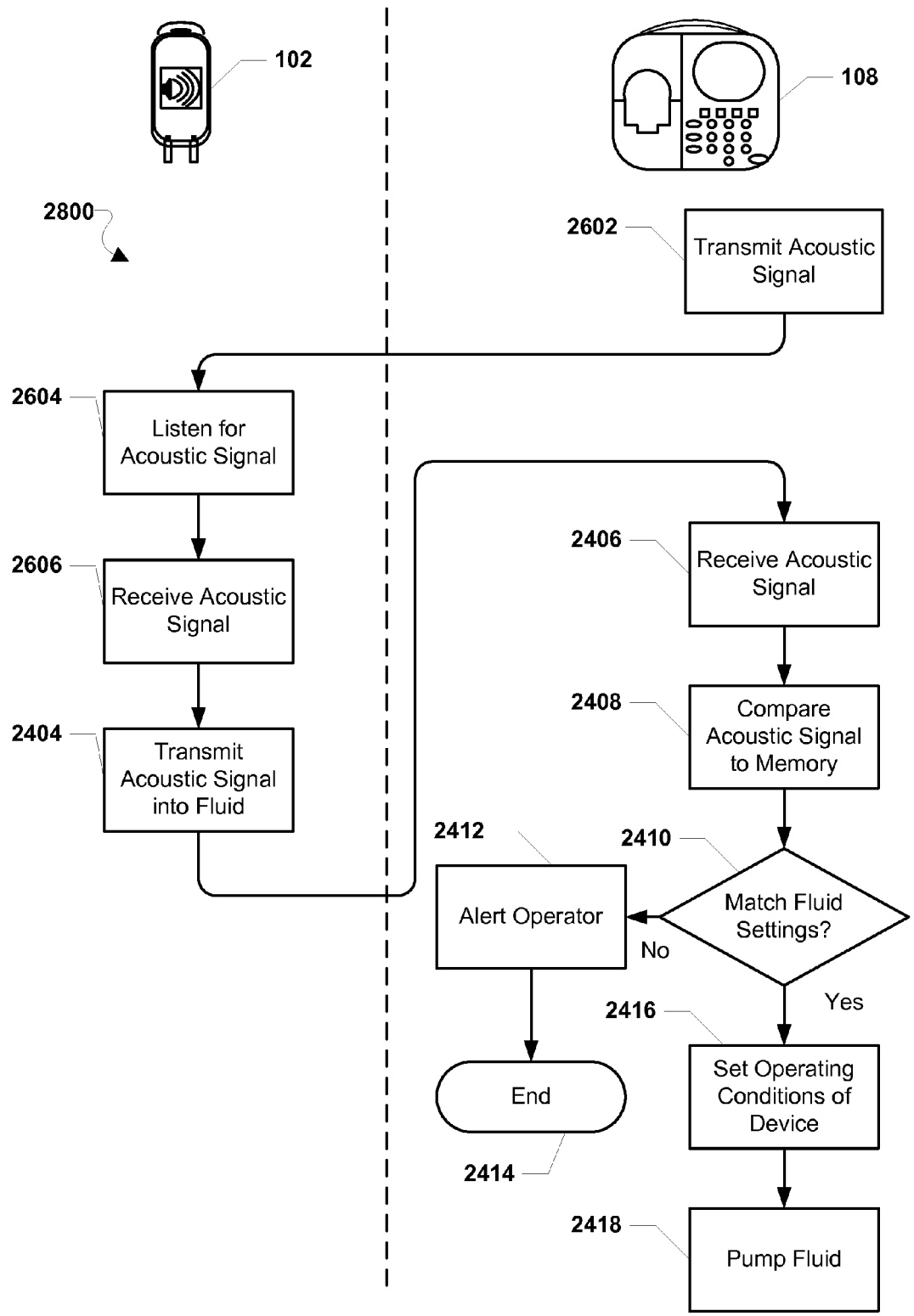
FIG. 28 is another process flow diagram illustrating a fifth embodiment method for fluid identification using acoustic communication through the fluid.

FIG. 28 illustrates another embodiment method 2800 similar to that described above with reference to FIG. 24, except that at block 2602 the IV pump 108 initiates communications by transmitting an acoustic signal via the fluid line to the IV bag 102. At block 2604, an acoustic tag at the IV bag 102 listens for an acoustic signal. When the acoustic signal is received the method 2800 proceeds to block 2404 as described above with reference to FIG. 24 and method 2400. In this manner, method 2800 may be performed using an acoustic tag which does not require a memory.

Figure 29:
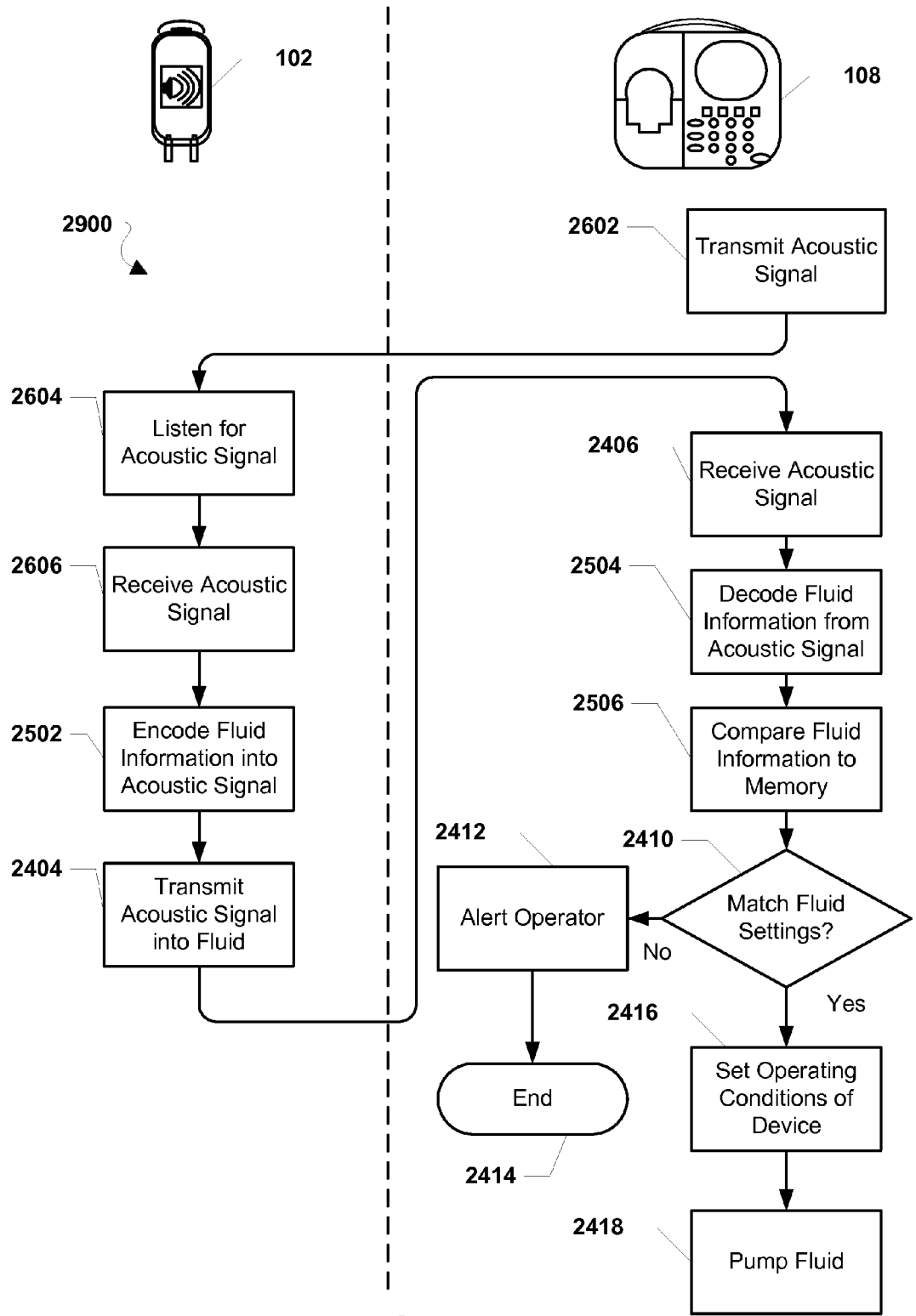
FIG. 29 is another process flow diagram illustrating a sixth embodiment method for fluid identification using acoustic communication through the fluid.

FIG. 29 illustrates another embodiment method 2900 similar to that described above with reference to FIG. 25, except that at block 2602 the IV pump 108 initiates communications at block 2602 by transmitting an acoustic signal via the fluid line to the IV bag 102. At block 2604 an acoustic tag at the IV bag 102 listens for an acoustic signal. When the acoustic signal is received the method 2800 proceeds to block 2502 as previously described with reference to FIG. 25 and method 2500. In this manner, the memory of the acoustic tag used to perform method 2900 may be need less storage capacity than memories in other embodiments because it need not store query signal characteristics.

Figure 30:
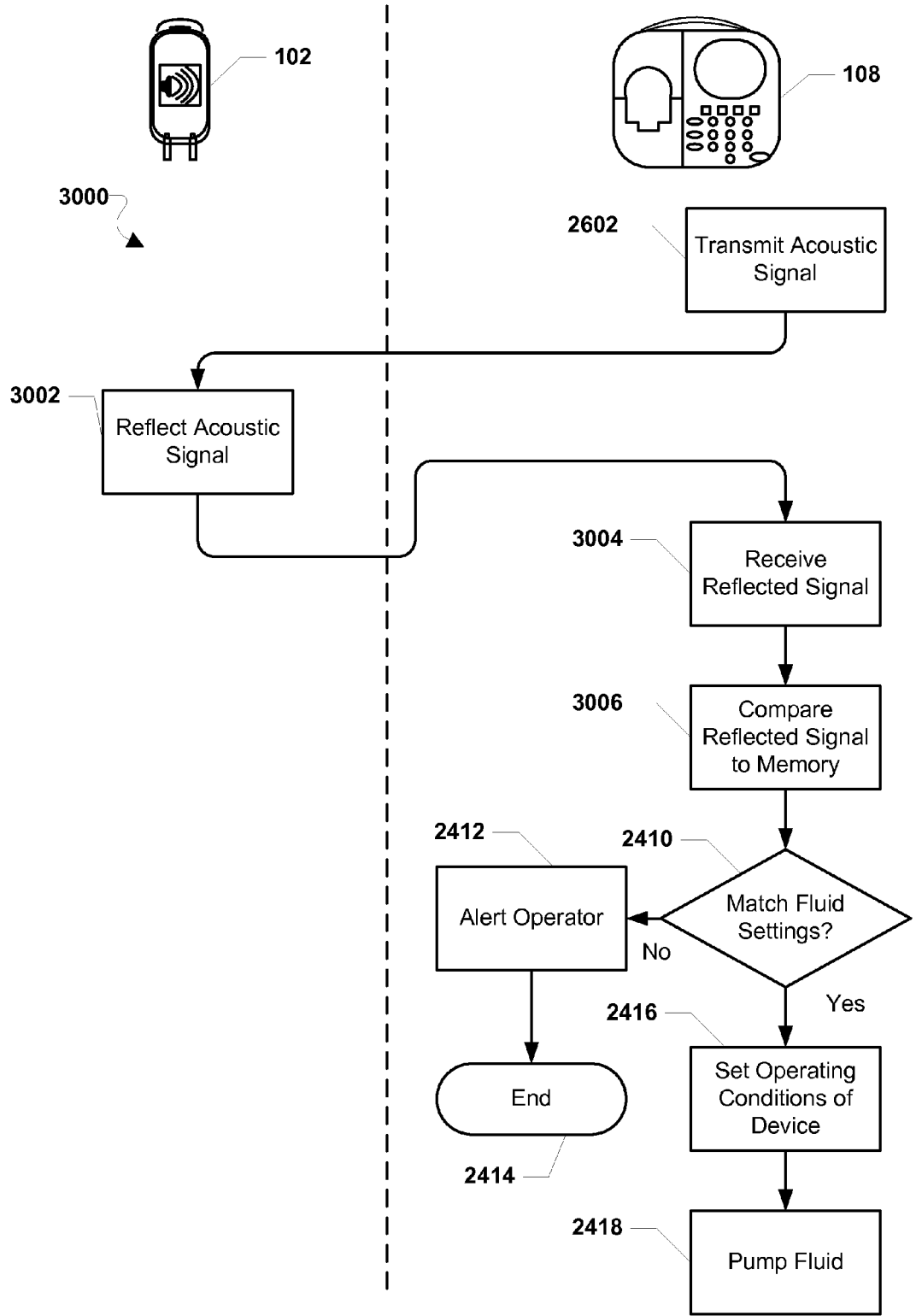
FIG. 30 is another process flow diagram illustrating a seventh embodiment method for fluid identification using acoustic communication through the fluid.

FIG. 30 illustrates another embodiment method 3000 similar to that described above with reference to FIG. 24, but tailored toward passive acoustic tags. At block 2602 the IV pump 108 initiates communications by transmitting an acoustic signal via the fluid line to the IV bag 102. At block 3002 the passive acoustic tag on or in the IV bag 102 reflects the acoustic signal in a recognizable manner. For example, the reflected acoustic signal may be at a different frequency than the originally transmitted acoustic signal. At block 3004, the IV pump 108 may receive the reflected acoustic signal. At block 3006, the IV pump 108 may compare the reflected signal to signal characteristics stored in memory. As an example, the IV pump 108 may compare the reflected signal to a table of tag frequencies associated with fluids in order to identify the fluid in the IV bag 102. The IV pump 108 may then proceed to determination block 2410 as described above with reference to FIG. 24 and method 2400.

Figure 31:
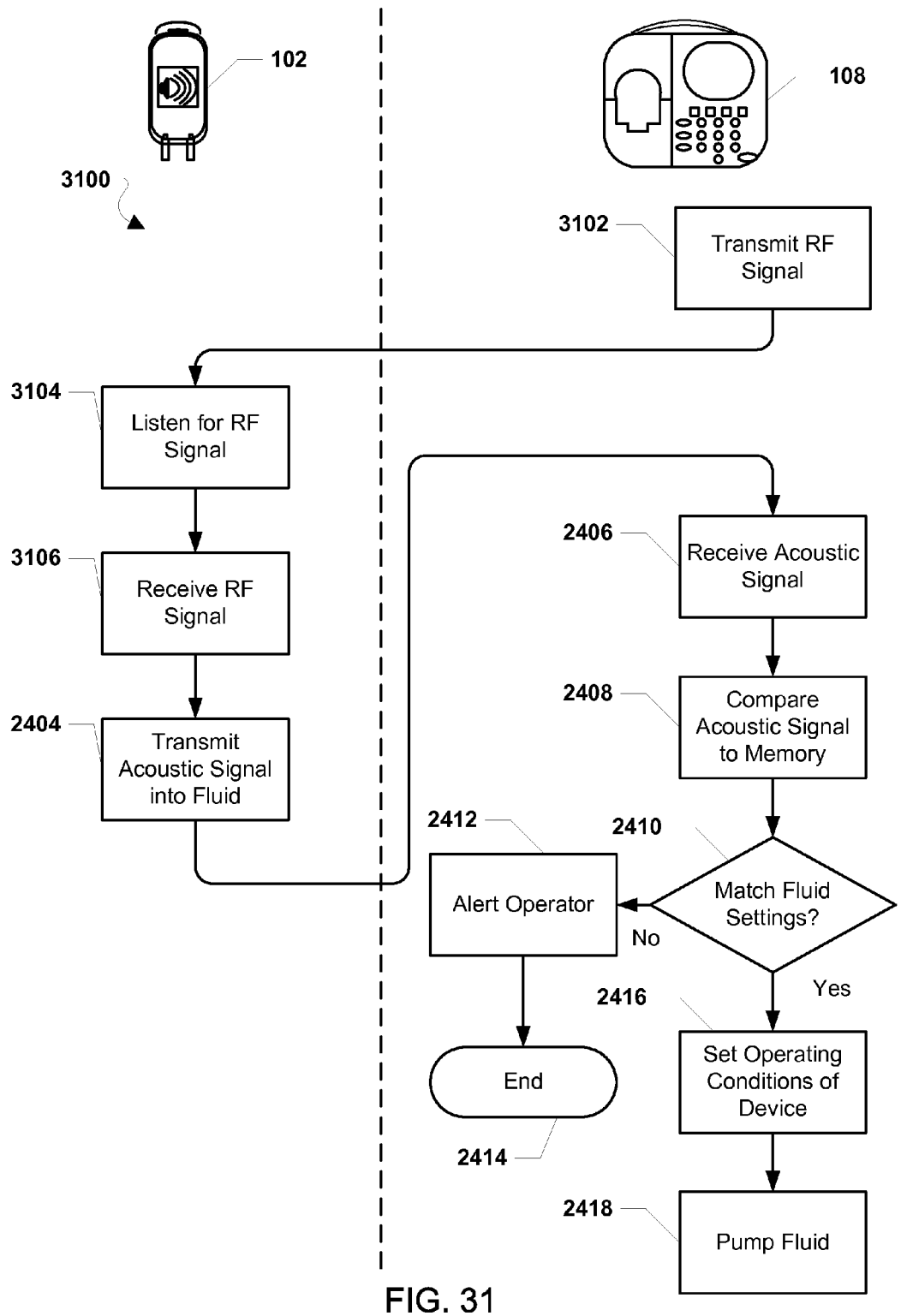
FIG. 31 is another process flow diagram illustrating an eighth embodiment method for fluid identification using acoustic communication through the fluid.

FIG. 31 illustrates another embodiment method 3100 similar to that described above with reference to FIG. 24, except that at block 3102, the IV pump 108 initiates communications by transmitting an RF signal. At block 3104, the acoustic tag listens for the RF signal. At block 3106, the acoustic tag receives the RF signal and proceeds to block 2404 as described above with reference to FIG. 24 and method 2400.

Figure 32:
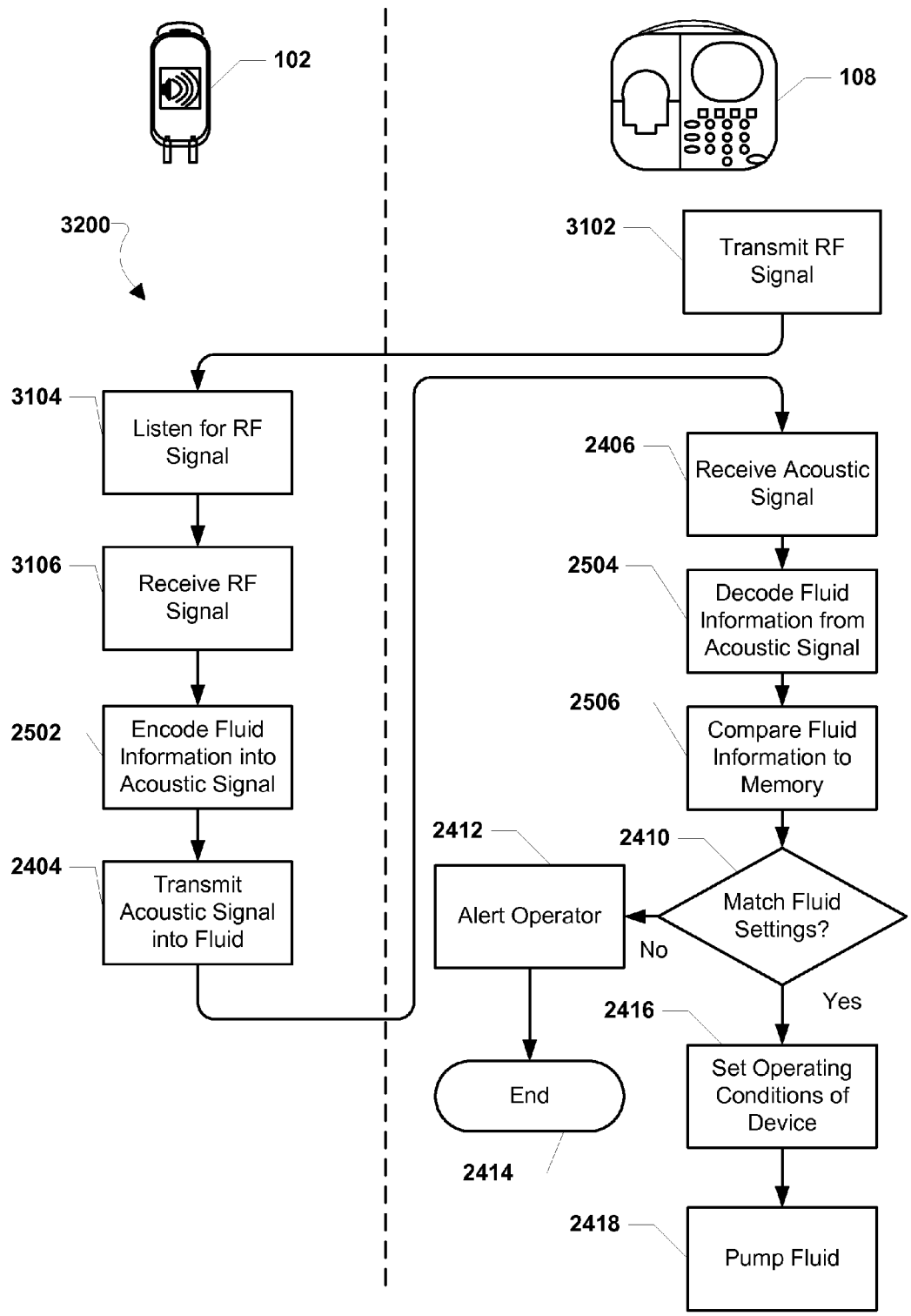
FIG. 32 is another process flow diagram illustrating a ninth embodiment method for fluid identification using acoustic communication through the fluid.

FIG. 32 illustrates another embodiment method 3200 similar to that described above with reference to FIG. 25, except that at block 3102 the IV pump 108 initiates communications by transmitting an RF signal. At block 3104, the acoustic tag listens for the RF signal. At block 3106 the acoustic tag receives the RF signal and proceeds to block 2502 as described above with reference to FIG. 25 and method 2500.

Figure 33:
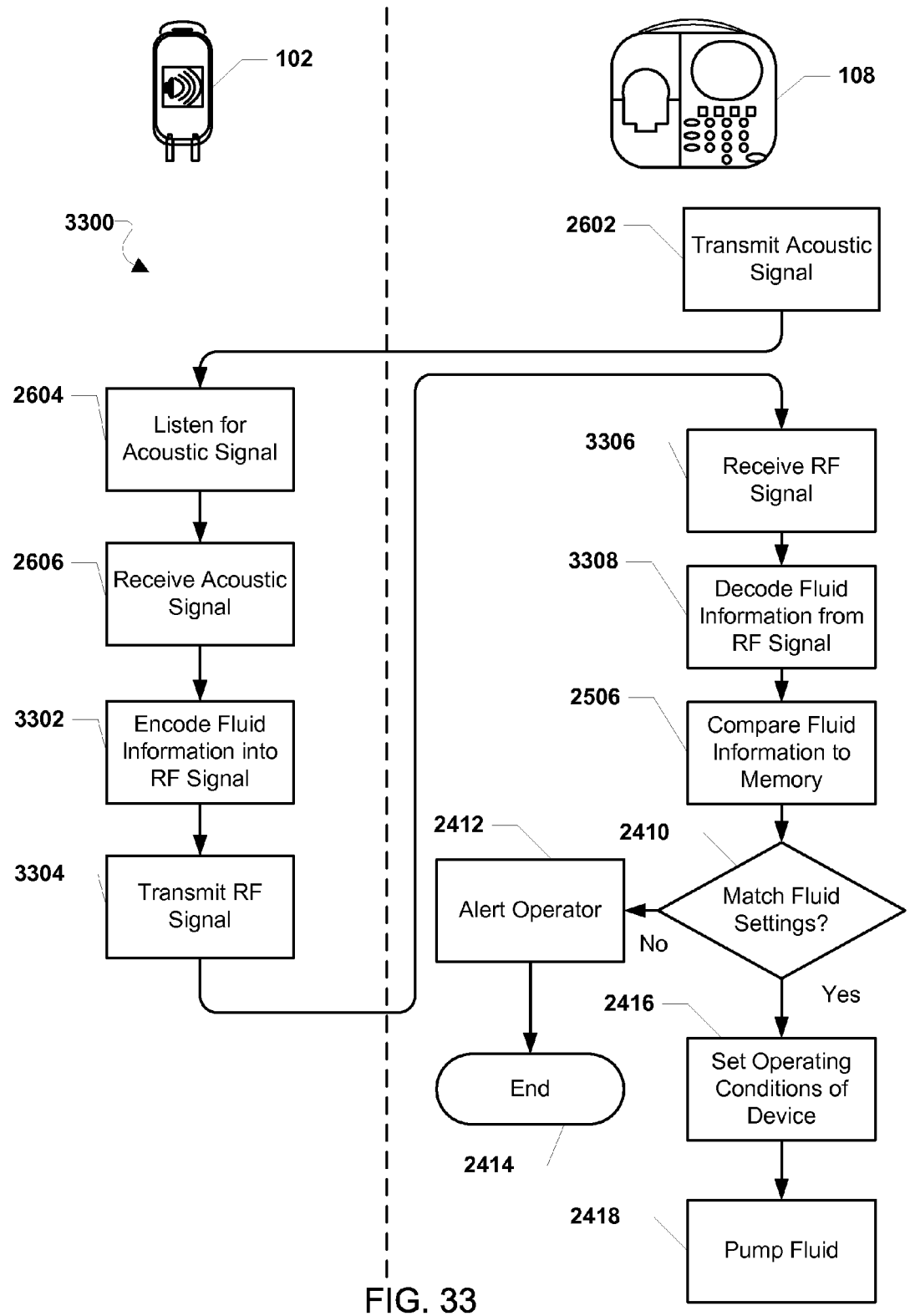
FIG. 33 is another process flow diagram illustrating a tenth embodiment method for fluid identification using acoustic communication through the fluid.

FIG. 33 illustrates another embodiment method 3300 similar to that described in FIG. 25 with the exception that at block 2602 the IV pump 108 initiates communications by transmitting an acoustic signal via the fluid line to the IV bag 102. At block 2604 an acoustic tag at the IV bag 102 listens for an acoustic signal. At block 2606 the acoustic tag receives the acoustic signal. At block 3302 the acoustic tag encodes fluid information into the RF signal. At block 3304 the acoustic tag transmits the RF signal. At block 3306 the RF signal is received at the IV pump. As part of block 3306, the pump controller may determining whether the received RF signal was transmitted in response to the acoustic activation signal. This may be based on timing of the received message, a code embedded in the RF signal, or other mechanism. At block 3308 the IV pump decodes the fluid information from the RF signal and proceeds to block 2506 as previously discussed with reference to FIG. 25. The response to the RF signal in block 3308 may depend upon whether the controller determines that the received RF signal was transmitted in response to the acoustic activation signal.

Figure 34:
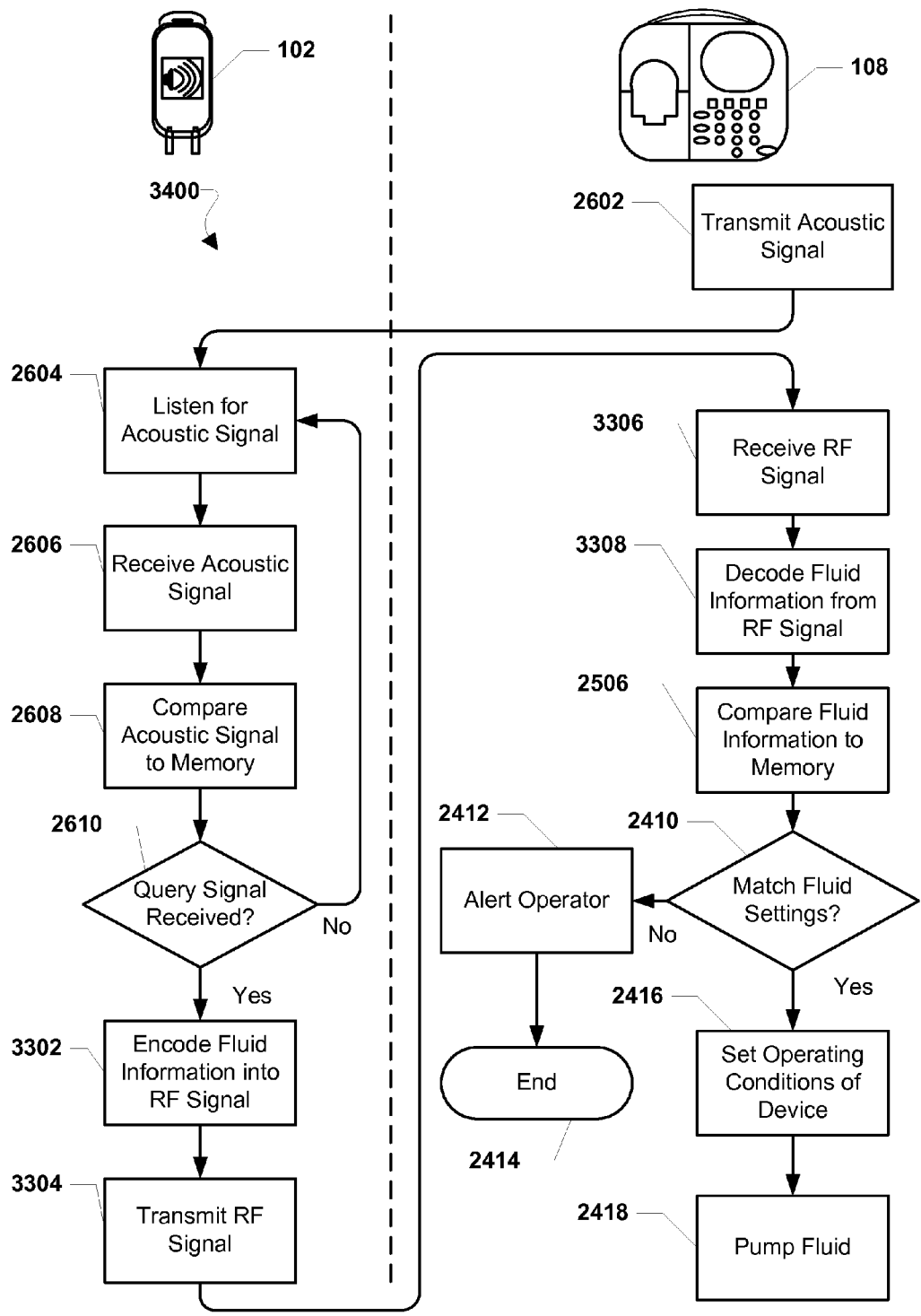
FIG. 34 is another process flow diagram illustrating an eleventh embodiment method for fluid identification using acoustic communication through the fluid.

FIG. 34 illustrates another embodiment method 3400 similar to that described above with reference to FIG. 33, with the addition of a query signal loop. At block 2602, the IV pump 108 may initiate communications by transmitting an acoustic signal via the fluid line to the IV bag 102. At block 2604, an acoustic tag at the IV bag 102 listens for an acoustic signal. At block 2606, the acoustic tag receives the acoustic signal. At block 2608, the acoustic tag compares the received acoustic signal to signal characteristics stored in a memory on the acoustic tag. As an example the acoustic tag may compare the frequency of the received signal to a frequency for query signals stored in the memory. At determination block 2610, the acoustic tag may determine if the received signal is a query signal. If the received signal is not a query signal (i.e., determination block 2610="No"), the acoustic tag may return to block 2604 to continue listening for an acoustic signal. If the signal received is a query signal (i.e., determination block 2610="Yes"), the acoustic tag may then proceed to block 3302 as described above with reference to FIG. 33 and method 3300.

Figure 35:
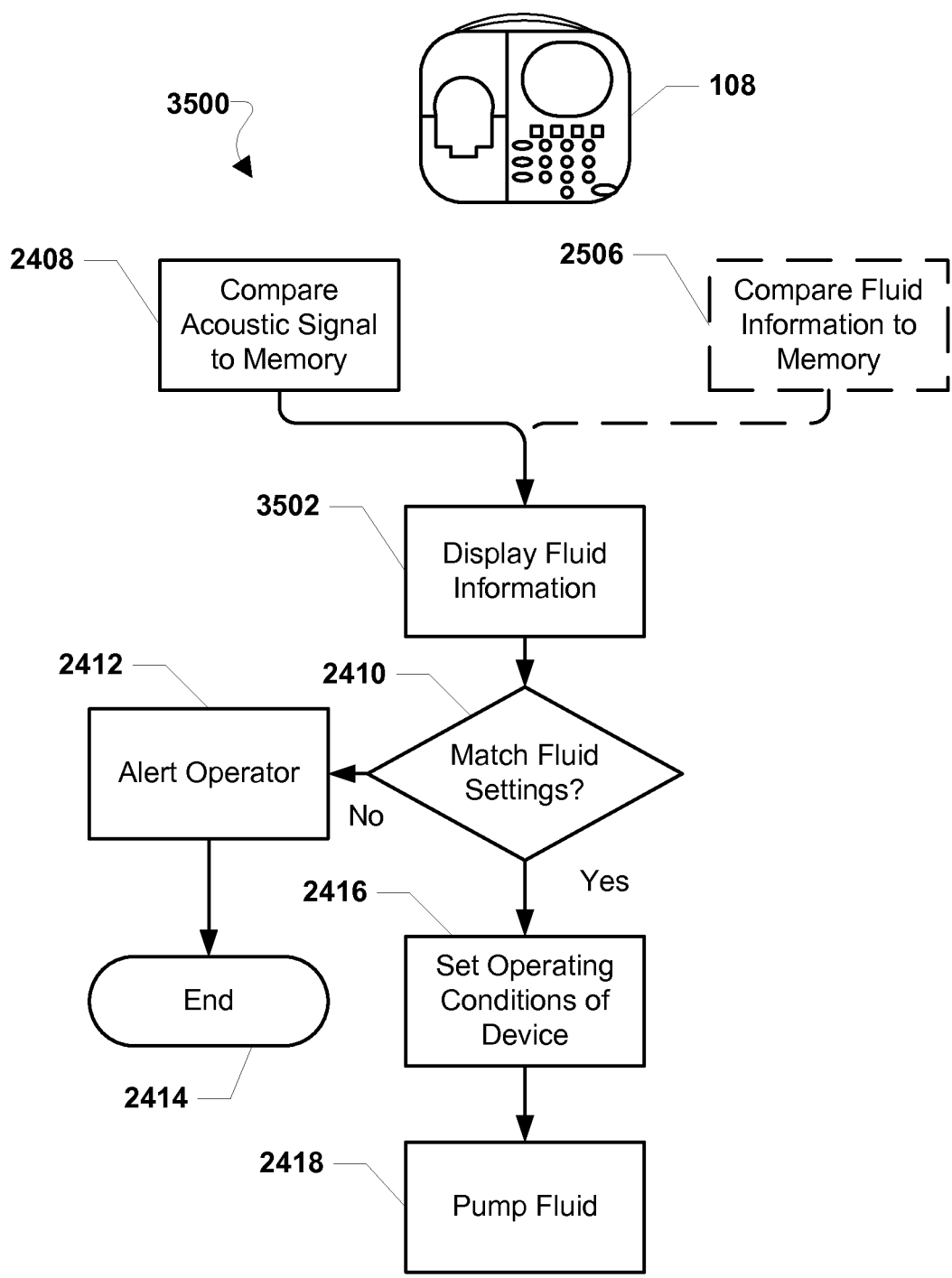
FIG. 35 is a process flow diagram illustrating a first embodiment method for controlling device operation in response to acoustic signals.

FIG. 35 illustrates an embodiment method 3500 for displaying fluid information on the IV pump that is similar to method 2400 described above with reference to FIGS. 24 and 2 method 2500 described above with reference to FIG. 25. After block 2408 in method 2400, or alternatively block 2506 in method 2500, the IV pump 108 proceeds to block 3502, and based on the comparison in either block 2408 or 2506, displays fluid information in a display of the IV pump 108. In this manner, method 3500 may provide further protections for patients because the fluid information is visually displayed on the IV pump. This may alert an operator to conduct manual safety verifications.

Figure 36:
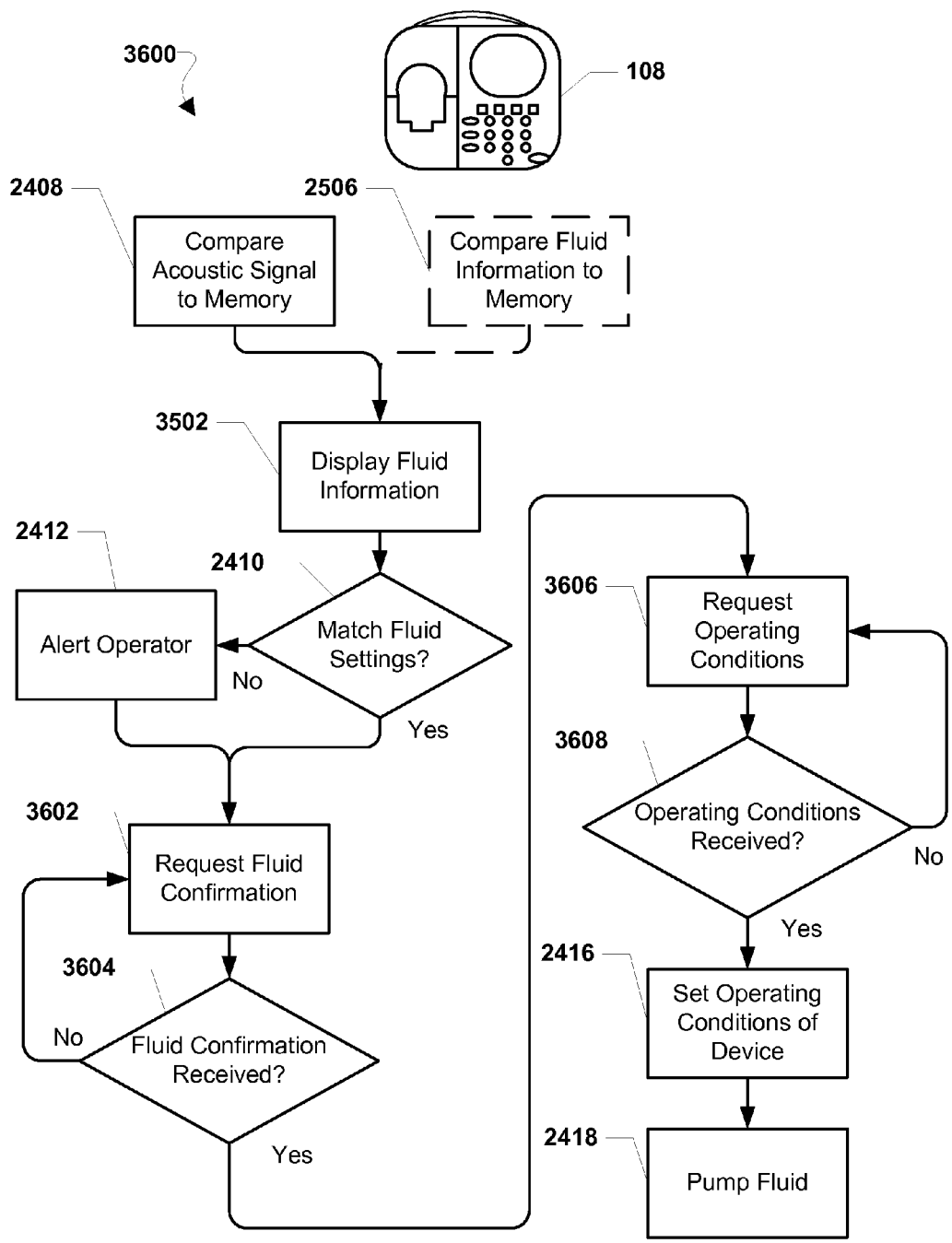
FIG. 36 is another process flow diagram illustrating a second embodiment method for controlling device operation in response to acoustic signals.

FIG. 36 illustrates an embodiment method 3600 that is similar to method 3500 described above with reference to FIG. 35, with the addition of a fluid confirmation request at block 3602. At block 3602, the IV pump 108 may request a confirmation of the fluid to be pumped. For example, the request may be via a display message or flashing light to which the operator may respond. Additionally, the fluid confirmation request at block 3602 replaces the end of pumping operations illustrated in FIG. 35 at block 2414. In this manner, method 3600 may enable the pumping of fluids not associated with current fluid settings. At determination block 3604, the IV pump 108 determines if a fluid confirmation was received. If not received (i.e., determination block 3604="No"), the IV pump 108 proceeds to block 3602 to request fluid confirmation. If the fluid confirmation is received (i.e., determination block 3604="Yes"), at block 3606 the IV pump 108 requests operating conditions. At determination block 3608, the IV pump 108 determines if the operating conditions are received. If the operating conditions are not received (i.e., determination block 3608="No"), the IV pump 108 proceeds to block 3606. If the operating conditions are received (i.e., determination block 3608="Yes"), at block 2416 the received operating conditions may be used to set the operating conditions for the IV pump 108, and at block 2418 the IV pump may begin to pump the fluid.

Figure 37:
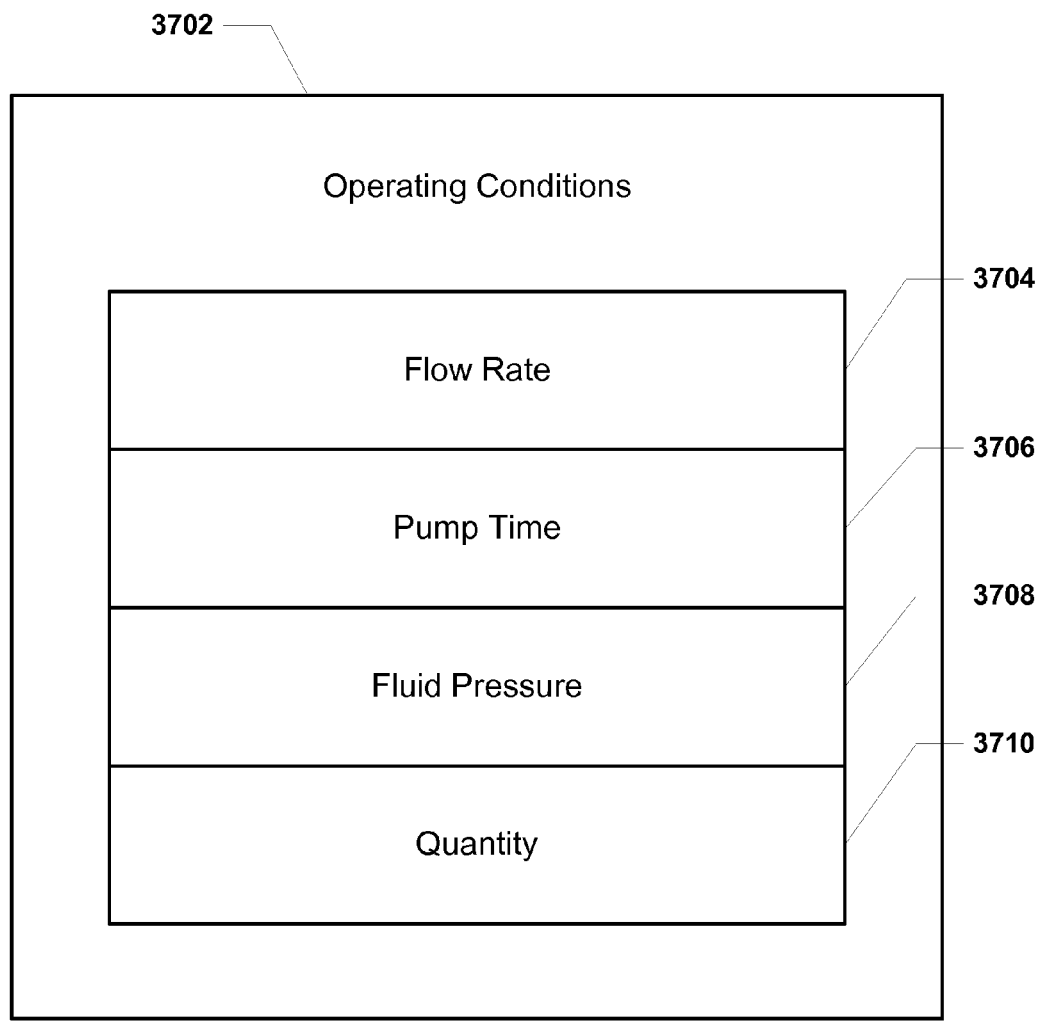
FIG. 37 is a data structure diagram of example device operating conditions.

FIG. 37 is a data structure diagram of potential operating conditions 3702 which may be stored in a memory and/or set for a fluid pumping device. Operating conditions 3702 may include flow rate 3704, pump time 3706, fluid pressure 3708, and quantity 3710.

Figure 38:
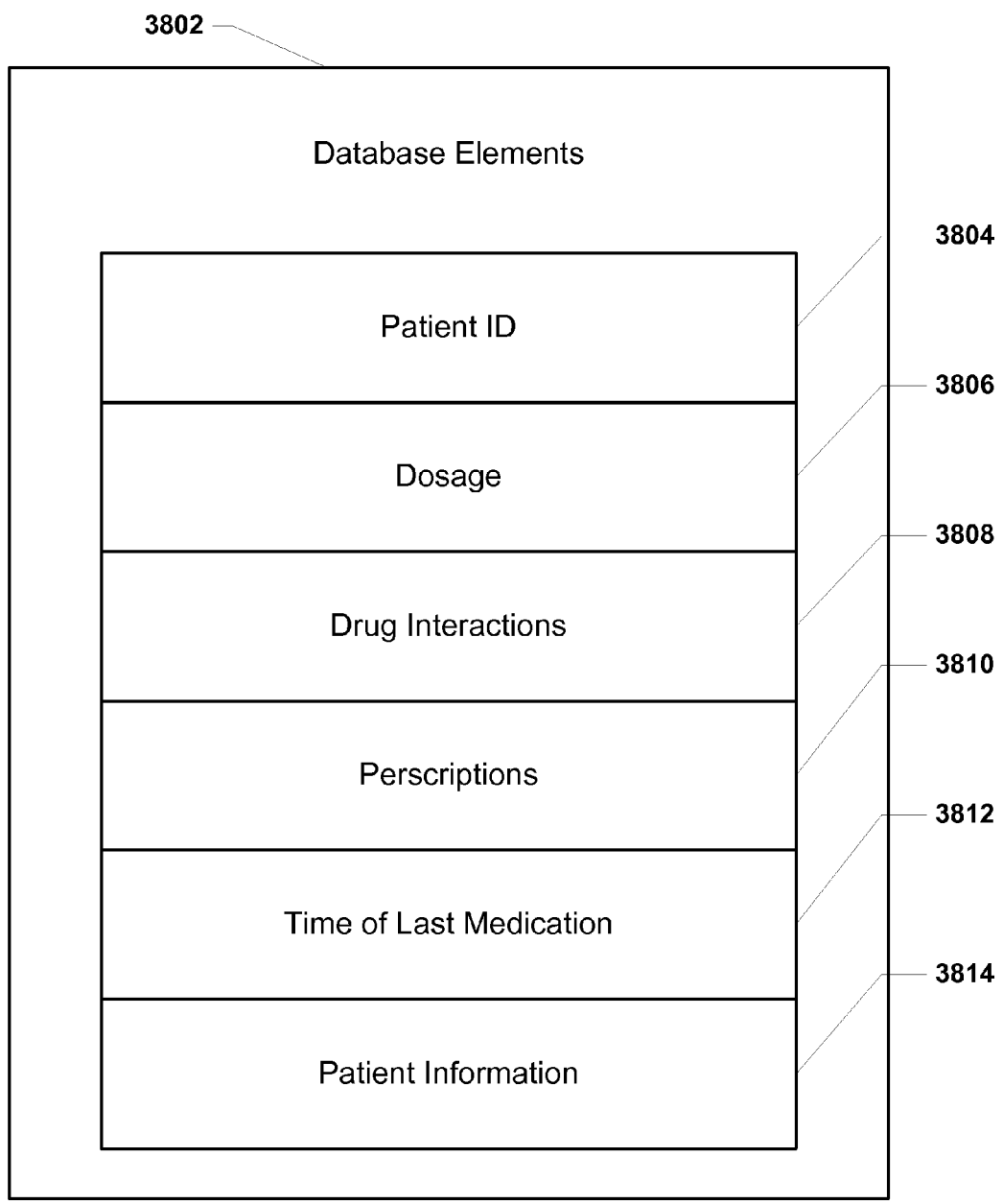
FIG. 38 is a data structure diagram of example elements in a patient information database.

FIG. 38 is a data structure diagram of potential database elements 3802 in a patient information database. Example data base elements 3802 may include patient ID 3804, dosage 3806, drug interactions 3808, prescriptions 3810, time of last medication 3812, and patient information 3814. These database elements may be loaded into a memory of the IV pump, may be stored in an external database available to the IV pump over a network, or maybe loaded into the memory of the acoustic modem. The database elements may additionally define the fluid settings of the IV pump.

In alternative embodiments, the acoustic tags may be used in any application in which it would be useful to communicate information between two devices via a direct acoustic path, such as a fluid connection. More particularly, the various embodiments may be used in any system for dispensing a fluid from fluid container. In general terms, an acoustic tag on, in or within a fluid container can communicate information to a fluid dispenser (e.g., a pump) via the acoustic channel formed by a fluid conduit (e.g., tube or pipe) disposed between the fluid container and the fluid dispenser.

In particular the various embodiments may also be implemented in a variety of industrial (i.e., non-medical) applications. Manufacturing applications may use the acoustic transmission to identify chemicals being added during the manufacturing process. Alternatively, food service outlets may use the embodiments to identify soft drink syrups and other dispensed liquids. For example, the embodiments may be implemented within a beverage dispenser in which the fluid container may be a beverage syrup bag, tank or canister, the fluid conduit may be the tube connected to the beverage syrup bag, and the pump, meter or dispenser may be the beverage dispenser which mixes syrup with carbonated water. In this embodiment, the acoustic modem may be included within the beverage dispenser, and a processor of the acoustic modem and/or of the beverage dispenser may be configured to recognize or process an acoustic signal emitted by the acoustic emitter within the beverage syrup bag that is conducted through fluid within the tube and/or the tube itself to obtain the encoded information, and to commence or suspend beverage fluid flow based upon the encoded information.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The steps of a method or algorithm disclosed herein may be embodied in a processor-executable software module which may reside on a tangible, non-transitory computer-readable storage medium. Tangible, non-transitory computer-readable storage media may be any available media that may be accessed by a computer. By way of example, and not limitation, such non-transitory computer-readable media may comprise RAM, ROM, EEPROM, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable media. Additionally, the operations of a method or algorithm may reside as one or any combination or set of codes and/or instructions on a tangible, non-transitory machine readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method for receiving information from a fluid container in fluid communication with a fluid conduit, the method comprising:
    receiving at a first device on or in the fluid container a first acoustic signal from a second device acoustically coupled to the fluid conduit;
    transducing the received first acoustic signal into an electrical signal;
    recognizing an acoustic activation signal in the transduced electrical signal;
    transmitting from the first device a second acoustic signal into a fluid disposed within the fluid container and the fluid conduit in response to recognizing the acoustic activation signal;
    receiving the second acoustic signal at the second device acoustically coupled to the fluid conduit; and
    taking an action in the second device based on the received second acoustic signal.

2. The method of claim 1, further comprising:
    comparing the received second acoustic signal to a signal characteristic stored in a second device memory to identify the fluid; and
    determining if the fluid matches a fluid setting for the second device;
    wherein taking an action in the second device based on the received acoustic signal comprises alerting an operator if the fluid does not match the fluid setting.

3. The method of claim 1, further comprising:
    comparing the transduced electrical signal to a signal characteristic stored in a memory at the fluid container to determine if the transduced electrical signal includes a query signal; and
    transmitting the second acoustic signal from the first device only when it is determined that the transduced electrical signal includes a query signal.

4. The method of claim 1, further comprising:
harvesting energy from the received first acoustic signal using energy harvested from the received first acoustic signal to generate the second acoustic signal.

5. The method of claim 1, wherein the fluid container is an IV bag, the first device is an acoustic tag coupled on or in the IV bag, and the second device is a medical pump configured to facilitate the administration of the fluid to a patient.

6. The method of claim 1, wherein the fluid container is a beverage syrup bag, the first device is an acoustic tag coupled on or in the beverage syrup bag, and the second device is a beverage dispenser configured to dispense a beverage.

7. The method of claim 1, further comprising:
encoding information into the second acoustic signal transmitted by the first device; and
decoding the information from the second acoustic signal received by the second device.

8. The method of claim 7, further comprising:
comparing the information decoded from the second acoustic signal to information stored in a second device memory to identify the fluid; and
determining if the fluid matches a fluid setting for the second device;
wherein taking an action in the second device based on the received second acoustic signal comprises alerting an operator if the fluid does not match the fluid setting.

9. A method for receiving information from a fluid container in fluid communication with a fluid conduit, the method comprising:
transmitting from a first device an acoustic activation signal into a fluid disposed within the fluid container and the fluid conduit;
receiving the acoustic activation signal in a second device positioned on or in the fluid container;
transducing at the second device the acoustic activation signal into an electrical signal;
recognizing at the second device the acoustic activation signal in the transduced electrical signal;
transmitting a radio frequency (RF) signal from the second device to the first device in response to recognizing the acoustic activation signal, the RF signal encoding information;
receiving the RF signal at the first device;
decoding the information from the received RF signal; and
taking an action in the first device based on the received RF signal.

10. A method for receiving information from a fluid container in fluid communication with a fluid conduit, the method comprising:
transmitting a first acoustic signal from a device acoustically coupled to the fluid conduit;
reflecting the first acoustic signal into the fluid disposed within the fluid container in a manner that changes an attribute of the first acoustic signal thereby creating a second acoustic signal with harmonic properties different than the first acoustic signal;
receiving the second acoustic signal at the device; and
taking an action in the device based on the second acoustic signal.

11. The method of claim 10, further comprising:
comparing the second acoustic signal to a signal characteristic stored in a device memory; and
determining if the fluid matches a fluid setting for the second device based on the comparison of the second acoustic signal to the signal characteristic stored in the second device memory,
wherein taking an action in the device based on the second acoustic signal comprises alerting an operator if the fluid does not match the fluid setting for the second device.

12. The method of claim 10, further comprising:
comparing the second acoustic signal to the first acoustic signal; and
using the harmonic differences between the first acoustic signal and second acoustic signal to determine information about the fluid or fluid container to the second device.

13. The method of claim 10, wherein the changed attribute of the first acoustic signal is a frequency component.

14. An acoustic tag configured to be attached to or positioned within a fluid container, the acoustic tag comprising:
a power source;
a controller coupled to the power source;
a pulse generator coupled to the controller and configured to produce electrical pulses in response to signals from the controller;
a first transducer coupled to the pulse generator, the first transducer configured to transmit an acoustic signal into a fluid disposed in the fluid container in response to electrical pulses produced by the pulse generator and to generate electrical signals in response to received acoustic signals;
a signal modifying circuit configured to modify electrical signals received from the first transducer;
an analog to digital converter coupled to the signal modifying circuit and to the controller and configured to convert modified electrical signals received from the signal modifying circuit into corresponding digital signals provided to the controller; and
wherein the controller is configured with processor-executable instructions to perform operations comprising:
recognizing an acoustic activation signal in digital signals received from the analog to digital converter; and
activating the pulse generator to cause the first transducer to transmit the acoustic signal transmitted into the fluid disposed in the fluid container in response to recognizing an acoustic activation signal.

15. The acoustic tag of claim 14, further comprising:
a switch coupled between the power source and the controller.

16. The acoustic tag of claim 14, wherein the first transducer is further configured to generate electrical signals in response to received acoustic signals, the acoustic tag further comprising a signal modifying circuit configured to receive electrical signals from the first transducer and provide modified signals to the controller, wherein the controller is configured with processor-executable instructions to perform operations comprising:
recognizing an acoustic activation signal in signals received from the signal modifying circuit; and
activating the pulse generator to cause the first transducer to transmit the acoustic signal transmitted into the fluid disposed in the fluid container in response to recognizing an acoustic activation signal.

17. The acoustic tag of claim 14, further comprising:
a second transducer configured to generate electrical signals in response to received acoustic signals;
an signal modifying circuit configured to modify electrical signals received from the second transducer;
an analog to digital converter coupled to the signal modifying circuit and to the controller and configured to convert modified electrical signals received from the signal modifying circuit into corresponding digital signals provided to the controller; and wherein the controller is configured with processor-executable instructions to perform operations comprising:
recognizing an acoustic activation signal in digital signals received from the analog to digital converter; and
activating the pulse generator to cause the first transducer to transmit the acoustic signal transmitted into the fluid disposed in the fluid container in response to recognizing an acoustic activation signal.

18. The acoustic tag of claim 17, wherein the first and second transducers are piezoelectric transducers.

19. The acoustic tag of claim 14, wherein the controller is configured with processor-executable instructions to perform operations comprising:
activating the pulse generator in a manner that encodes information into the acoustic signal transmitted into the fluid disposed in the fluid container.

20. The acoustic tag of claim 14, the acoustic tag further comprising:
an antenna; and
a radio frequency (RF) receiver coupled to the antenna and to the controller;
wherein the controller is configured with processor-executable instructions to perform operations comprising:
receiving an RF signal via the RF receiver; and
activating the pulse generator to cause the first transducer to transmit the acoustic signal transmitted into the fluid disposed in the fluid container in response to receiving the RF signal at the acoustic tag.

21. The acoustic tag of claim 14, wherein the fluid container is one of an intravenous (IV) fluid bag and a beverage syrup bag.

22. An acoustic tag configured to be attached to a fluid container, the acoustic tag comprising:
a power source;
a controller coupled to the power source;
a transducer configured to generate electrical signals in response to received acoustic signals;
an signal modifying circuit configured to modify electrical signals received from the transducer and provide modified signals to the controller;
an antenna; and
a radio frequency (RF) transmitter coupled to the antenna and to the controller;
wherein the controller is configured with processor-executable instructions to perform operations comprising:
recognizing an activation signal in signals received from the analog to digital converter; and
activating the RF transmitter to cause the antenna to transmit an RF signal from the acoustic tag in response to recognizing the activation signal.

23. The acoustic tag of claim 22, wherein the fluid container is one of an intravenous (IV) fluid bag and a beverage syrup bag.

24. An apparatus, comprising:
a first transducer configured to generate electrical signals in response to received acoustic signals;
a controller;
a signal modifying circuit configured to receive electrical signals from the first transducer and provide modified signals to the controller;
wherein the controller is configured with processor-executable instructions to perform operations comprising:
recognizing a first acoustic signal in the signals received from the signal modifying circuit; and
directing a device to take an action in response to recognizing the first acoustic signal;
a pulse generator coupled to the controller and configured to produce electrical pulses in response to signals from the controller; and
a second transducer configured to transmit an acoustic activation signal into a fluid disposed in a fluid conduit in response to electrical pulses produced by the pulse generator.

25. The apparatus of claim 24, wherein the device is a pump configured to be fluidically coupled to a fluid container, and wherein the controller is configured with processor-executable instructions to perform operations further comprising:
identifying a fluid within the fluid container based at least in part on the recognized first acoustic signal; and
determining if the fluid matches a fluid setting of the pump, wherein directing the device to take an action in response to recognizing the first acoustic signal comprises directing the pump to alert an operator if the fluid does not match the fluid setting.

26. The apparatus of claim 24, further comprising:
a pulse generator coupled to the controller and configured to produce electrical pulses in response to signals from the controller; and
wherein the first transducer is further configured to transmit an acoustic activation signal into a fluid disposed in a fluid conduit in response to electrical pulses produced by the pulse generator.

27. The apparatus of claim 24, wherein the first and second transducers are piezoelectric transducers.

28. The apparatus of claim 24, further comprising:
an antenna; and
a radio frequency (RF) transmitter coupled to the antenna and the controller;
wherein the controller is configured with processor-executable instructions to perform operations further comprising:
activating the RF transmitter to cause the antenna to transmit an RF signal.

29. The apparatus of claim 25, wherein the fluid container is one of an intravenous (IV) fluid bag and a beverage syrup bag, and the pump is one of a medical pump configured to facilitate the administration of the fluid to a patient and a beverage dispenser configured to dispense a beverage.

30. A system for dispensing a fluid, comprising:
a fluid container having a fluid disposed therein;
a fluid dispenser device;
a fluid conduit disposed between the fluid container and the fluid dispenser; and
an acoustic tag, on or in the fluid container, comprising:
a power source;
a first controller coupled to the power source;
a first pulse generator coupled to the first controller and configured to produce electrical pulses in response to signals from the first controller;
a first transducer coupled to the first pulse generator, the first transducer configured to transmit a first acoustic signal into a fluid disposed in the fluid container in response to electrical pulses produced by the first pulse generator and to generate electrical signals in response to received acoustic signals,
wherein the fluid dispenser device comprises:
a second controller;
a second transducer configured to receive acoustic signals from the fluid conduit and generate electrical signals in response to received acoustic signals; and
a first signal modifying circuit configured to receive electrical signals from the second transducer and provide modified signals to the second controller, wherein the second controller is configured with processor-executable instructions to perform operations comprising:
  recognizing the first acoustic signal in the signals received from the first signal modifying circuit; and
  causing the fluid dispenser device to take an action in response to recognizing the first acoustic signal, the action taken selected from the group including dispensing fluid, not dispensing fluid, displaying an identity of the fluid, and sounding an alarm,
wherein the acoustic tag further comprises a second signal modifying circuit configured to receive electrical signals from the first transducer and provide modified signals to the first controller, and
wherein the first controller is configured with processor-executable instructions to perform operations further comprising:
  recognizing an acoustic activation signal in signals received from the second signal modifying circuit; and
  activating the first pulse generator to cause the first transducer to transmit the first acoustic signal into the fluid disposed in the fluid container in response to recognizing the acoustic activation signal,
wherein the fluid dispenser device further comprises second pulse generator coupled to the second controller and configured to produce electrical pulses in response to signals from the second controller, and
wherein the second transducer is further configured to transmit the acoustic activation signal into the fluid disposed in the fluid conduit in response to electrical pulses produced by the second pulse generator.

31. The system of claim 30, wherein the second controller is configured with processor-executable instructions to perform operations further comprising:
  identifying the fluid disposed in the fluid container based at least in part on the recognized first acoustic signal; and
  determining if the fluid matches a fluid setting of the device,
  wherein causing the fluid dispenser device to take an action in response to recognizing the first acoustic signal comprises causing the fluid dispenser to sound an alarm to alert an operator if the fluid does not match the fluid setting.

32. The system of claim 30, wherein:
the acoustic tag further comprises:
  a first antenna; and
  a radio frequency (RF) transmitter coupled to the first antenna and the second controller;
the second controller is configured with processor-executable instructions to perform operations further comprising activating the RF transmitter to cause the first antenna to transmit an RF signal from the acoustic modem;
the acoustic tag further comprises:
  a second antenna; and
  a radio frequency (RF) receiver coupled to the second antenna and to the first controller; and
the first controller is configured with processor-executable instructions to perform operations further comprising:
  receiving an RF signal via the RF receiver; and
  activating the first pulse generator to cause the first transducer to transmit the first acoustic signal into the fluid disposed in the fluid container in response to receiving the RF signal at the acoustic tag.

33. The system of claim 30, wherein the first controller is configured with processor-executable instructions to perform operations further comprising:
  activating the first pulse generator in a manner that encodes information into the first acoustic signal transmitted into the fluid disposed in the fluid container.

34. The system of claim 30, wherein the fluid container is one of an intravenous (IV) fluid bag and a beverage syrup bag, and the fluid dispenser device is one of a medical pump configured to facilitate the administration of the fluid to a patient and a beverage dispenser configured to dispense a beverage.

35. A system for dispensing a fluid, comprising:
  a fluid container having a fluid disposed therein;
  a fluid dispenser device;
  a fluid conduit disposed between the fluid container and the fluid dispenser; and
  an acoustic tag, on or in a fluid container, comprising:
    a power source;
    a first controller coupled to the power source;
    a first transducer configured to generate electrical signals in response to received acoustic signals;
    a first signal modifying circuit configured to modify electrical signals received from the first transducer and provide modified signals to the first controller;
    a first antenna; and
    a radio frequency (RF) transmitter coupled to the first antenna and to the first controller,
    wherein the first controller is configured with processor-executable instructions to perform operations comprising:
      recognizing an acoustic activation signal in signals received from the first signal modifying circuit; and
      activating the RF transmitter to cause the first antenna to transmit an RF signal from the acoustic tag in response to recognizing the acoustic activation signal; and
  wherein the fluid dispenser device comprises:
    a second controller;
    a first pulse generator coupled to the second controller and configured to produce electrical pulses in response to signals from the second controller;
    a second transducer configured to transmit the acoustic activation signal into the fluid disposed in the fluid conduit in response to electrical pulses produced by the first pulse generator;
    a second antenna; and
    a radio frequency (RF) receiver coupled to the second antenna and to the second controller,
    wherein the second controller is configured with processor-executable instructions to perform operations comprising:
      receiving the RF signal via the RF receiver; and
      causing the fluid dispenser device to take an action in response to recognizing the first acoustic signal, the action taken selected from the group including dispensing fluid, not dispensing fluid, displaying an identity of the fluid, and sounding an alarm.

36. The system of claim 35, wherein the fluid container is one of an intravenous (IV) fluid bag and a beverage syrup bag, and the fluid dispenser device is one of a medical pump configured to facilitate the administration of the fluid to a patient and a beverage dispenser configured to dispense a beverage.

37. A system, comprising:
   means for receiving at a first device on or in the fluid container a first acoustic signal from a second device acoustically coupled to the fluid conduit;
   means for transducing at the first device the first acoustic signal into an electrical signal;
   means for recognizing at the first device an acoustic activation signal in the transduced electrical signal;
   means for transmitting from the first device a second acoustic signal into a fluid disposed within the fluid container and a fluid conduit in response to recognizing the acoustic activation signal;
   means for receiving the second acoustic signal at the second device acoustically coupled to the fluid conduit; and
   means for taking an action in the second device based on the received second acoustic signal.

38. The system of claim 37, further comprising:
   means for comparing the received second acoustic signal to a signal characteristic stored in a second device memory to identify the fluid; and
   means for determining if the fluid matches a fluid setting for the second device,
   wherein the means for taking an action in the second device based on the received first acoustic signal comprises means for alerting an operator if the fluid does not match the fluid setting.

39. The system of claim 37, further comprising:
   means for comparing the transduced electrical signal to a signal characteristic stored in a memory at the fluid container to determine if the transduced electrical signal includes a query signal; and
   means for transmitting the second acoustic signal from the first device when it is determined that the transduced electrical signal includes a query signal.

40. The system of claim 37, further comprising:
   means for harvesting energy from the received first acoustic signal; and means for using energy harvested from the received first acoustic signal to generate the second acoustic signal.

41. The system of claim 37, wherein the fluid container is an IV bag, the first device is an acoustic tag coupled on or in the IV bag, and the second device is a medical pump configured to facilitate the administration of the fluid to a patient.

42. The system of claim 37, wherein the fluid container is a beverage syrup bag, the first device is an acoustic tag coupled on or in the beverage syrup bag, and the second device is a beverage dispenser configured to dispense a beverage.

43. The system of claim 37, further comprising:
   means for encoding information into the second acoustic signal transmitted by the first device; and
   means for decoding the information from the second acoustic signal received by the second device.

44. The system of claim 43, further comprising:
   means for comparing the information decoded from the second acoustic signal to information stored in a second device memory to identify the fluid; and
   means for determining if the fluid matches a fluid setting for the second device,
   wherein means for taking an action in the second device based on the received second acoustic signal comprises means for alerting an operator if the fluid does not match the fluid setting.

45. A system, comprising:
   means for transmitting from a first device an acoustic activation signal into a fluid disposed within a fluid container and a fluid conduit;
   means for receiving the acoustic activation signal in a second device positioned on or in the fluid container;
   means for transducing at the second device the acoustic activation signal into an electrical signal;
   means for recognizing at the second device an acoustic activation signal in the transduced electrical signal;
   means for transmitting an RF signal encoding information from the second device to the first device in response to recognizing the acoustic activation signal;
   means for receiving the RF signal at the first device; and
   means for taking an action in the first device based on the received RF signal.

46. A system, comprising:
   a fluid container having a fluid disposed therein;
   a fluid conduit fluidically coupled to the fluid container;
   means for transmitting a first acoustic signal from a device acoustically coupled to the fluid within the fluid conduit;
   means for reflecting the first acoustic signal into the fluid disposed within the fluid container in a manner that changes an attribute of the first acoustic signal thereby creating a second acoustic signal with properties different from the first acoustic signal;
   means for receiving the second acoustic signal at the device; and
   means for taking an action based on the second acoustic signal.

47. The system of claim 46, further comprising:
   means for comparing the second acoustic signal to a signal characteristic stored in a device memory; and
   means for determining if the fluid matches a fluid setting for the second device based on the comparison of the second acoustic signal to the signal characteristic stored in the second device memory,
   wherein means for taking an action in the device based on the second acoustic signal comprises means for alerting an operator if the fluid does not match the fluid setting for the second device.

48. The system of claim 46, further comprising:
   means for comparing the second acoustic signal to the first acoustic signal; and
   means for using the differences between the first acoustic signal and second acoustic signal to determine information about the fluid or fluid container.

49. The system of claim 46, wherein the changed attribute of the first acoustic signal is a frequency component.

50. An acoustic tag configured to be attached to or positioned within a fluid container, the acoustic tag comprising:
   means for transducing an acoustic signal received from the fluid container into an electrical signal;
   means for recognizing an activation signal in the transduced electrical signal; and
   means for transmitting an acoustic signal into a fluid disposed in the fluid container in response to recognizing the activation signal.

51. The acoustic tag of claim 50, further comprising:
   means for encoding information into the acoustic signal transmitted into the fluid disposed in the fluid container.

52. The acoustic tag of claim 50, wherein the fluid container is one of an intravenous (IV) fluid bag and a beverage syrup bag.

53. An acoustic tag configured to be attached to or positioned within a fluid container, the acoustic tag comprising:
   means for transducing an acoustic signal received from the fluid container into an electrical signal;
   means for recognizing an acoustic activation signal in the transduced electrical signal; and means for transmitting a radio frequency (RF) signal in response to recognizing the acoustic activation signal.

54. The acoustic tag of claim 53, wherein the fluid container is one of an intravenous (IV) fluid bag and a beverage syrup bag.

55. A non-transitory processor-readable medium having stored thereon processor-executable instructions configured to cause an acoustic tag processor to perform operations comprising:
processing received signals to recognize an activation signal in the received signals; and
transmitting an acoustic signal into a fluid disposed in the fluid container in response to recognizing the activation signal.

56. The non-transitory processor-readable medium of claim 55, wherein the stored processor-executable instructions are configured to cause an acoustic tag processor to perform operations such that:
processing the received signals to recognize an activation signal in the received signals comprises recognizing an acoustic activation signal in the received signals; and
transmitting the acoustic signal into a fluid disposed in the fluid container is performed in response to recognizing the acoustic activation signal.

57. The non-transitory processor-readable medium of claim 55, wherein the stored processor-executable instructions are configured to cause an acoustic tag processor to perform operations further comprising:
encoding information into the acoustic signal transmitted into the fluid disposed in the fluid container.

58. The non-transitory processor-readable medium of claim 55, wherein the stored processor-executable instructions are configured to cause an acoustic tag processor to perform operations such that recognizing an activation signal in received signals comprises recognizing an activation signal in a received radio frequency (RF) signal.

59. A non-transitory processor-readable medium having stored thereon processor-executable instructions configured to cause an acoustic tag processor to perform operations comprising:
transducing an acoustic activation signal received from the fluid medium into an electrical signal;
recognizing the acoustic activation signal in the electrical signal; and
transmitting a radio frequency (RF) signal in response to recognizing the acoustic activation signal.

60. A method for receiving information from a fluid container, the method comprising:
transmitting an acoustic signal into a fluid disposed within the fluid container;
receiving a reflected acoustic signals from the fluid; and
detecting a particular change in an attribute of the received reflected acoustic signal.

61. The method of claim 60, wherein the particular change in an attribute of the received reflected acoustic signal is a change in a frequency component.

62. An acoustic tag, comprising:
an acoustic reflector assembly configured to reflect a first acoustic signal into a fluid disposed within a fluid container in a manner that changes an attribute of the first acoustic signal thereby creating a second acoustic signal with acoustic properties recognizably different from the first acoustic signal.

63. The acoustic tag of claim 62, wherein the acoustic reflective assembly is configured to diminish or suppress an amplitude of a particular frequency in the second acoustic signal.

64. The acoustic tag of claim 63, wherein the acoustic reflective assembly comprises a Helmholtz resonator.

* * * * *